(12) United States Patent
Xu et al.

(10) Patent No.: US 8,334,316 B2
(45) Date of Patent: Dec. 18, 2012

(54) SUBSTITUTED ORGANOSULFUR COMPOUNDS AND METHODS OF USING THEREOF

(75) Inventors: Xiao Xu, San Diego, CA (US); Haoyun An, Carlsbad, CA (US); Xiaobo Wang, San Diego, CA (US)

(73) Assignee: ACEA Biosciences, Inc., San Diego, CA (US)

( * ) Notice: Subject to any disclaimer, the term of this patent is extended or adjusted under 35 U.S.C. 154(b) by 796 days.

(21) Appl. No.: 12/368,206

(22) Filed: Feb. 9, 2009

(65) Prior Publication Data

US 2009/0192146 A1 Jul. 30, 2009

Related U.S. Application Data

(62) Division of application No. 11/110,203, filed on Apr. 20, 2005, now Pat. No. 7,622,507.

(60) Provisional application No. 60/564,151, filed on Apr. 20, 2004.

(51) Int. Cl.

| | | |
|---|---|---|
| A61K 31/343 | (2006.01) |
| A61K 31/381 | (2006.01) |
| A61K 31/40 | (2006.01) |
| A61K 31/4025 | (2006.01) |
| A61K 31/404 | (2006.01) |
| A61K 31/41 | (2006.01) |
| A61K 31/415 | (2006.01) |
| A61K 31/4164 | (2006.01) |
| A61K 31/4184 | (2006.01) |
| A61K 31/4192 | (2006.01) |
| A61K 31/42 | (2006.01) |
| A61K 31/425 | (2006.01) |
| A61K 31/428 | (2006.01) |
| A61K 31/433 | (2006.01) |
| A61K 31/44 | (2006.01) |
| A61K 31/4427 | (2006.01) |
| A61K 31/47 | (2006.01) |
| A61K 31/495 | (2006.01) |
| A61K 31/497 | (2006.01) |
| A61K 31/50 | (2006.01) |
| A61K 31/505 | (2006.01) |
| A61K 31/53 | (2006.01) |
| C07D 279/08 | (2006.01) |
| C07D 277/02 | (2006.01) |
| C07D 277/62 | (2006.01) |
| C07D 275/02 | (2006.01) |
| C07D 285/02 | (2006.01) |
| C07D 271/02 | (2006.01) |
| C07D 263/02 | (2006.01) |
| C07D 261/02 | (2006.01) |
| C07D 251/02 | (2006.01) |
| C07D 249/02 | (2006.01) |
| C07D 241/02 | (2006.01) |
| C07D 241/46 | (2006.01) |
| C07D 239/02 | (2006.01) |
| C07D 237/02 | (2006.01) |
| C07D 237/28 | (2006.01) |
| C07D 237/30 | (2006.01) |
| C07D 235/04 | (2006.01) |
| C07D 233/54 | (2006.01) |
| C07D 231/02 | (2006.01) |
| C07D 219/00 | (2006.01) |
| C07D 217/00 | (2006.01) |
| C07D 215/00 | (2006.01) |
| C07D 213/02 | (2006.01) |
| C07D 209/04 | (2006.01) |
| C07D 207/30 | (2006.01) |

(52) U.S. Cl. .......... 514/438; 544/49; 544/180; 544/237; 544/238; 544/242; 544/257; 544/336; 544/353; 546/138; 546/139; 546/152; 548/127; 548/131; 548/146; 548/215; 548/255; 548/300.1; 548/364.1; 548/400; 548/469; 549/29; 549/49; 549/462; 514/226.8; 514/241; 514/247; 514/248; 514/252.01; 514/252.1; 514/256; 514/306; 514/307; 514/311; 514/362; 514/363; 514/365; 514/372; 514/374; 514/383; 514/385; 514/396; 514/412; 514/434; 514/439; 514/469

(58) Field of Classification Search .................. 544/238, 544/242, 49, 180, 237, 257, 336, 353; 514/252.1, 514/256, 226.8, 242, 247, 248, 252.01, 306, 514/307, 311, 336, 362, 363, 365, 372, 374, 514/383, 385, 396, 412, 434, 438, 439, 469; 546/138, 139, 152; 548/127, 131, 146, 215, 548/255, 300.1, 364.1, 400, 469; 549/29, 549/49, 462

See application file for complete search history.

(56) References Cited

U.S. PATENT DOCUMENTS 5,464,861 A 11/1995 Dobrusin et al.
(Continued)

FOREIGN PATENT DOCUMENTS

EP 0 720 983 7/1996
(Continued)

OTHER PUBLICATIONS

Pourshahbaz et al, Tetrahedron Letters (2009), vol. 50 (44), pp. 5987-5989.*

(Continued)

*Primary Examiner* — Kamal Saeed
*Assistant Examiner* — Janet L Coppins
(74) *Attorney, Agent, or Firm* — Morrison & Foerster LLP

(57) ABSTRACT

The present invention provides substituted di-, tri-, tetra- and penta-sulfide compounds and compositions, and methods of using the same for the treatment and/or prevention of a cell proliferative disorder. The present invention also provides methods for preparing trisulfide compounds and compositions.

20 Claims, 48 Drawing Sheets

U.S. PATENT DOCUMENTS

| | | | |
|---|---|---|---|
| 6,552,060 | B1 | 4/2003 | Kirkpatrick |
| 6,583,157 | B2 | 6/2003 | McGee et al. |
| 6,683,200 | B2 | 1/2004 | Mita et al. |
| 2002/0198410 | A1 | 12/2002 | Sinha et al. |
| 2003/0176512 | A1 | 9/2003 | Kirkpatrick |
| 2004/0152067 | A1 | 8/2004 | Wang et al. |
| 2005/0112544 | A1 | 5/2005 | Xu et al. |
| 2005/0153425 | A1 | 7/2005 | Xu et al. |

FOREIGN PATENT DOCUMENTS

| | | |
|---|---|---|
| EP | 1 172 358 | 1/2002 |
| FR | 2629817 | 4/1988 |
| JP | 5-078253 | 3/1993 |
| JP | 8-253454 | 10/1996 |
| JP | 11-130746 | 5/1999 |
| JP | 2000-351761 | 12/2000 |
| JP | 2002-193796 | 7/2002 |
| JP | 2003-155489 | 5/2003 |
| WO | WO-2004/010102 | 1/2004 |
| WO | WO-2004/010103 | 1/2004 |
| WO | WO-2005/047482 | 5/2005 |

OTHER PUBLICATIONS

Zhang et al, J. Ag. & Food Chem (1991), vol. 39 (6), pp. 1145-1148.*
Database CAPLUS, accession No. 1988:590002 (1988).
Do et al., Bulletin de la Societe Chimique de France (1996) 3:273-282.
Feher et al., Zeitschrift fur Naturforschung (1968) 23(8):1030-1033.
Genesty et al., Acta Chemica Scandinavica (1999) 53(10):952-954.
Hayashi et al., Chemical and Pharmaceutical Bulletin (1969) 17(5):954-958.
Luttringhaus et al., Liebigs Annalen der Chemie (1948) 560:201-214.
Milligan et al., Journal of the Chemical Society (1963) 7:3608-3614.
Monge et al., Journal of Heterocyclic Chemistry (1988) 25(1):23-28.
Ramesha et al., Journal of Organic Chemistry (1994) 59(6):1354-1357.
Ryu et al., Bioorganic and Medicinal Chemistry (2004) 12(5):859-864.
Singh et al., Journal of Organic Chemistry (1988) 53(11):2608-2612.
Sirikawa et al., Chemical and Pharmaceutical Bulletin (1970) 18(2):235-242.
Supplementary European Search Report for EP 05779301.0, mailed Mar. 2, 2010, 7 pages.
Banerji and Kalena, Tetrahedron Letters (1980) 21:3003-3004.
Grassetti et al., Journal of Medicinal Chemistry (1965) 8(6):753-756.
Notice of Reasons for Rejection (translation) for JP 2007-509600, mailed Jan. 21, 2011, 7 pages.
Ayodele et al., Phosphorous, Sulfur and Silicon (2002) 177:261-275.
Banerji et al., Tetrahedron Letters (1980) 21:3003-3004.
CAPLUS AN:1966:67469; abstract of Aghoramurthy, Tetrahedron (1966) 22(2):415-417.
CAPLUS AN:2003:857026; abstract of Williams et al., Recent Research Developments in Phyochemistry (2002) 6:13-68.
Derbesy et al., Tetrahedron Letters (1994) 35:5381-5384.
Farb et al., Circulation (1999) 99:44-52.
Furniss et al., Vogel's Textbook of Practical Organic Chemistry, Longman Group Limited, London, (1978) pp. 582-583.
Harpp and Granata, Tetrahedron Letters (1976) 35:3001-3004.
Harpp et al., Org. Chem. (1971) 36:322-326.
Harpp et al., Org. Chem. (1979) 44:4135-4140.
International Search Report for PCT/US05/13474, mailed in Nov. 9, 2006, 2 pages.
Mata-Greenwood et al., Anticancer Res. (2001) 21:763-1770.
Morice et al., New England Journal of Medicine (2002) 346:1773-1780.
Moses et al., New England Journal of Medicine (2003) 349:1315-1323.
Panda et al., PNAS USA (1997) 94:10560-10564.
Rosner et al., Biochim. Biophy. Acta (2001) 1540:166-177.
Sinha et al., Organometallics (2001) 20:157-162.
Stone et al., New England Journal of Medicine (2004) 350:221-231.
Weung et al., Biochim. Biophys. Res. Comm. (1997) 263:398-404.
Williams et al., Chemosphere (2003) 51:701-706.
Williams et al., Phytother. Res. (1997) 11:251-253.
Witte et al., Cancer Metastasis Rev. (1998) 17:155-161.
Written Opinion for PCT/US05/13474, mailed on Nov. 9, 2006, 4 pages.
Yeung et al., Biochim Biophys Res Comm (1997) 263:398-404.
Blank et al., "Degradation of the Coffee Flavor Compound Furfuryl Mercaptan in Model Fenton-type Reaction Systems," J. Agric. Food Chem. (2002) 50:2356-2364.
Notice of Final Rejection, including English-language translation, for JP 2007-509600, mailed Sep. 26, 2011, 11 pages.
Restriction Requirement for U.S. Appl. No. 11/110,203, mailed Feb. 8, 2007, 11 pages.
Response to Restriction Requirement for U.S. Appl. No. 11/110,203, filed Mar. 15, 2007, 11 pages.
Office Action for U.S. Appl. No. 11/110,203, mailed Jul. 2, 2007, 17 pages.
Response to Office Action for U.S. Appl. No. 11/110,203, filed Dec. 3, 2007, 19 pages.
Final Office Action for U.S. Appl. No. 11/110,203, mailed Mar. 17, 2008, 11 pages.
Response to Final Office Action for U.S. Appl. No. 11/110,203, filed Apr. 18, 2008, 10 pages.
Notice of Appeal for U.S. Appl. No. 11/110,203, filed Sep. 17, 2008, 1 page.
Notice of Allowance for U.S. Appl. No. 11/110,203, mailed Nov. 18, 2008, 8 pages.
Request for Continued Examination for U.S. Appl. No. 11/110,203, filed Jul. 17, 2009, 13 pages.
Supplemental Amendment for U.S. Appl. No. 11/110,203, filed Jul. 28, 2009, 10 pages.
Notice of Allowance (Second) for U.S. Appl. No. 11/110,203, mailed Oct. 1, 2009, 7 pages.

* cited by examiner

| Paclitaxel, 1 uM | Paclitaxel, 3 uM | Paclitaxel, 9 uM |

| Paclitaxel, 1 uM | Paclitaxel, 3 uM | Paclitaxel, 9 uM |
|---|---|---|
|  |  |  |
|  |  |  |

| Vinblastine, 1 uM | Vinblastine, 3 uM | Vinblastine, 9 uM |
|---|---|---|
|  |  |  |
|  |  |  |

Vinblastine, 1 uM    Vinblastine, 3 uM    Vinblastine, 9 uM

DBTS, 2 uM      DBTS, 6 uM      DBTS, 18 uM dead      dead dead      dead

ACEA100108, 1 uM  ACEA100108, 3 uM  ACEA100108, 9 uM

ACEA100108, 1 uM   ACEA100108, 3 uM   ACEA100108, 9 uM

ACEA100116, 1 uM    ACEA100116, 3 uM    ACEA100116, 9 uM

ACEA100116, 1 uM    ACEA100116, 3 uM    ACEA100116, 9 uM

Mostly dead    Mostly dead

Mostly dead    Mostly dead 5,000x 80,000x 150,000x 100,000x 150,000x

SUBSTITUTED ORGANOSULFUR COMPOUNDS AND METHODS OF USING THEREOF

CROSS-REFERENCE TO RELATED APPLICATION

This application is a DIVISIONAL of U.S. patent application Ser. No. 11/110,203, filed Apr. 20, 2005, which claims the benefit of priority under 35 U.S.C. §119(e) of U.S. Provisional Application No. 60/564,151, filed Apr. 20, 2004: the contents of each of these applications are incorporated herein by reference in their entirety.

TECHNICAL FIELD

The invention relates to organosulfur compounds and methods of using thereof.

BACKGROUND ART

Cancer remains one of the most important unmet medical challenges to mankind. A number of options for treating tumors are available, including surgery, radiation, chemotherapy, or any combination of these approaches. Among these, chemotherapy is widely used for all types of cancers, in particular for those inoperable or with metastatic characteristics. Despite a variety of chemotherapeutic compounds being used in clinics, chemotherapy is generally not curative, but only delays disease progression. Commonly, tumors and their metastasis become refractory to chemotherapy, as the tumor cells develop the ability of multidrug resistance. In some cases, the tumors are inherently resistant to some classes of chemotherapeutic agents. In other cases, the acquired resistance against chemotherapeutic agents is developed during the chemotherapeutic intervention. Thus, there remain significant limitations to the efficacy of available chemotherapeutic compounds in treating different classes of tumors. Furthermore, many cytotoxic and cytostatic agents used for chemotherapeutic treatment of tumors have severe side effects, resulting in termination of the chemotherapy in some patients. Thus, there remains a need for new chemotherapeutic agents.

Dibenzyl trisulfide (DBTS) is a biologically active polysulfide secondary metabolite that was isolated from the sub-tropical shrub, *Petiveria alliacea* L. (Phytolaccaceae). It has been reported that DBTS has immunomodulatory activities ("Immunomodulatory activities of *Petiveria alliacea*.", by Williams, L. A. D., Gardner, T. L., Fletcher, C. K., Naravane, A., Gibbs, N. and Fleischhacker, R. *Phytother. Res.*, 1997, 11, 251-253; "A sulfonic anhydride derivative from dibenzyl trisulphide with agro-chemical activities", by Williams, L. A. D., Vasquez, E., Klaiber, I., Kraus, W. and Rosner, H. *Chemosphere*, 2003, 51, 701-706). In investigating the cellular and molecular mechanisms of DBTS for its immunomodulatory activity, Rosner and co-workers reported that DBTS preferentially binds to an aromatic region of bovine serum albumin and attenuates the dephosphorylation of tyrosyl residues of MAP kinase (erk1/erk2) in SH-SY5Y neuroblastoma cells (in "Disassembly of microtubules and inhibition of neurite outgrowth, neuroblastoma cell proliferation, and MAP kinase tyrosine dephosphorylation by dibenzyl trisulphide", by Rosner, H., Williams, L. A. D., Jung, A. and Kraus, W. *Biochim. Biophy. Acta*, 2001, 1540, 166-177). In addition, they reported that DBTS causes a reversible disassembly of microtubules and did not affect actin dynamics in SH-SY5Y neuroblastoma cells and in Wistar 38 human lung fibroblasts. Furthermore, they reported that DBTS also inhibits neuroblastoma cell proliferation and neurite outgrowth from spinal cord explants.

In a different study, Mata-Greenwood and co-workers tested the antiproliferative and differentiating activity of a large set of extracts derived from various plants ("Discovery of novel inducers of cellular differentiation using HL-60 promyeolocytic cells", by Mata-Greenwood, E., Ito A., Westernburg, H., Cui, B., Mehta, R. G., Kinghorn, A. D. and Pezzuto, J. M. *Anticancer Res.* 2001, 21, 1763-1770). They reported that the lipophilic extract of the roots of *Petiveria alliacea* L., and the active fraction from the lipophilic extract showed antiproliferative and differentiating activity in HL-60 promyelocytic cells. From the active fraction of the lipophilic extract, they isolated two active organosulfur compounds, i.e., 2-[(phenylmethyl)dithio]ethanol and dibenzyl trisulfide. They reported that these two organosulfur compounds induced monocyte-like differentiation and strong cytotoxicity. Furthermore, they reported that none of these two isolates demonstrated antiproliferative activity in HL-60 cells.

DISCLOSURE OF THE INVENTION

The present invention relates to organosulfur compounds, pharmaceutical compositions, and methods of using thereof. More particularly, the present invention relates to substituted di-, tri-, tetra- and penta-sulfide compounds, including pharmaceutically acceptable salts and partially oxidized sulfone derivatives thereof. Compounds as described herein exhibit anti-tumor, anticancer, anti-inflammation, anti-infectious, and/or antiproliferation activity. The present invention also relates to methods of making and formulating organosulfur compounds.

In one embodiment, the invention provides compounds having formula

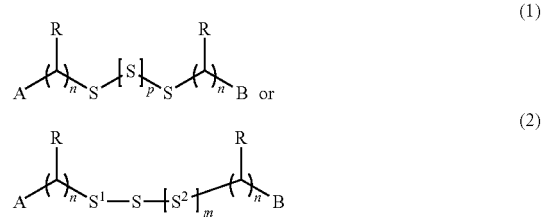

wherein A and B are the same or different, and are independently an optionally substituted aryl, heteroaryl, or a 5-14 membered ring which may be monocyclic or multicyclic and optionally containing a heteroatom;

each S is optionally in the form of an oxide;

$S^1$ and $S^2$ are independently S, SO or $SO_2$;

each R is H, halogen, carboxyl, cyano, amino, amido, an amino acid, an inorganic substituent, $SR^1$, $OR^1$ or $R^1$, wherein each $R^1$ is alkyl, alkenyl, alkynyl, aryl, heteroaryl, a carbocyclic ring or a heterocyclic ring, each of which is optionally substituted and may contain a heteroatom;

m, n and p are independently 0-3;

or a compound having formula (3) or (4):

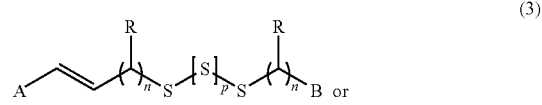

(4)

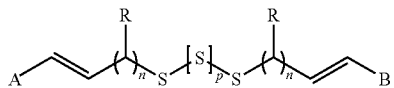

wherein A, B, R, S, n and p are as defined above;
or a compound having formula (5):

(5)

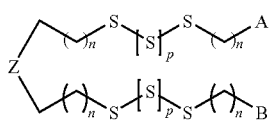

wherein A, B, S, n and p are as defined above; and
Z is $(CR^1{}_2)_q$ or $(CR^1{=}CR^1)_q{}^*$ wherein q is 0-3 and the * represents that C=C may be replaced with alkynyl, O, S, NR; or Z is an optionally substituted aryl, heteroaryl or heterocyclic ring;
wherein A and B together may form a cyclic ring system;
and a pharmaceutically acceptable salt, ester, prodrug or metabolite thereof;
provided said compound is not dibenzyltrisulfide, di(p-chlorobenzyl)trisulfide, (p-chlorobenzyl)benzyltrisulfide, di(p-nitrobenzyl)trisulfide, di(3-phenyl-2-propenyl)-trisulfide, diphenyltrisulfide, or di(p-t-butylphenyl)trisulfide.

In the above formula 1-5, each Z may be

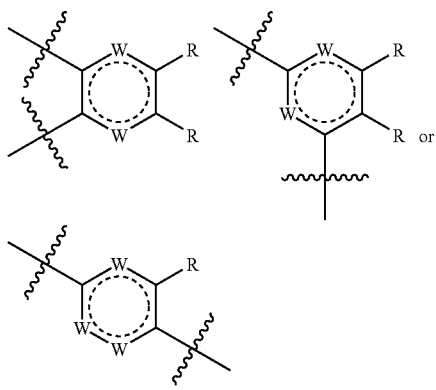

wherein each W is independently a bond, CR, N, NR, S, or O;
each R is as defined above.

In the above formula 1-5, each R may be H, halo, $OR^1$, $SR^1$, $CO_2R^1$, $CONR^1{}_2$, C=O, CN, $CF_3$, $OCF_3$, $NO_2$, $NR_1R_1$, $OCOR_1$; or R is $C_{1-10}$ alkyl, $C_{3-10}$ cyclic alkyl, $C_{2-10}$ alkenyl, $C_{2-10}$ alkynyl, an aryl, heteroaryl, a carbocyclic ring or a heterocyclic ring, each of which may contain a heteroatom.

In the above formula 1-5, each A and B may be benzene, pyridine, pyridazine, pyrimidine, pyrazine, triazine, isoxazole, isothiazole, oxadiazole, [1,2,4]oxadiazole, triazole, thiadiazole, pyrazole, imidazole, thiazole, oxazole, benzoxazole, pyrrole, furan, thiophene indolizine, indole, isoindole, indoline, benzofuran, benzothiophene, indazole, benzimidazole, benzthiazole, purine, quinoxaline, quinoline, isoquinoline, cinnoline, phthalazine, quinazoline, quinoxaline, naphthyridine, pteridine, acridine, phenazine, phenothiazine, indene, naphthalene, benzoxadiazol, or benzo[1,2,5]-oxadiazole.

In another aspect, each A and B are independently

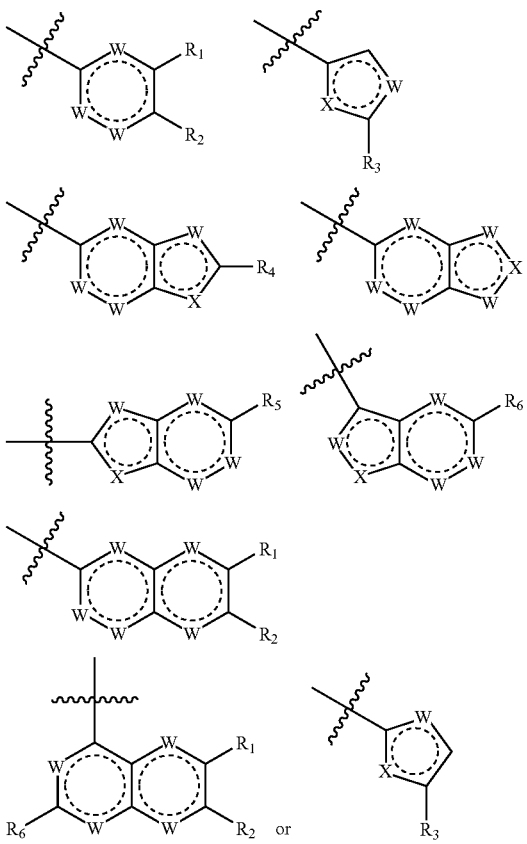

where X and W are independently S, O, $NR_7$, $CR_7$;
or one W in a 6-membered monocyclic or bicyclic ring may be a bond; and
each $R_1$, $R_2$, $R_3$, $R_4$, $R_5$, $R_6$, $R_7$ is H, halogen, carboxyl, cyano, amino, amino acid, amido, an inorganic substituent, $SR^1$, $OR^1$ or $R^1$, wherein each $R^1$ is alkyl, alkenyl, alkynyl, aryl, heteroaryl, a carbocyclic ring or a heterocyclic ring, each of which is optionally substituted and may contain a heteroatom. For example, each $R_1$, $R_2$, $R_3$, $R_4$, $R_5$, $R_6$, $R_7$ may be H, halo, $OR^1$, $SR^1$, $CO_2R^1$, $CONR^1{}_2$, C=O, CN, $CF_3$, $OCF_3$, $NO_2$, $NR_1R_1$, $OCOR_1$; or each $R_1$, $R_2$, $R_3$, $R_4$, $R_5$, $R_6$, $R_7$ is $C_{1-10}$ alkyl, $C_{3-10}$ cyclic alkyl, $C_{2-10}$ alkenyl, $C_{2-10}$ alkynyl, an aryl, heteroaryl, a carbocyclic ring or a heterocyclic ring, each of which may contain a heteroatom.

Examples of aryl, heteroaryl, or heterocyclic ring include but are not limited to piperazine, piperidine, morpholine, thiomorpholine, phenyl, furanyl, thiophenyl, pyridinyl, pyrimidinyl, pyrazinyl, triazinyl, quinoxalinyl, thiazolyl, oxazolyl, imidazolyl, quinolinyl, naphthalenyl, pyridazinyl, pyrazolopyrimidinyl, benzoimidazolyl, benzothiazolyl, benzene-thiophene, pyrazolyl, pyrrolyl, indolyl, isoindolyl, quinolizinyl, quinolinyl, isoquinolinyl, or quinazolinyl, each of which is optionally substituted with a heteroatom selected from O, N, S and halo; or substituted with $C_{1-10}$ alkyl, $C_{3-10}$ cyclic alkyl, $C_{2-10}$ alkenyl, $C_{2-10}$ alkynyl, aryl, or heterocycle, each optionally containing a heteroatom.

In the above formula 1-5, each S may be a mono-oxide or a di-oxide.

In another aspect, the compound has the formula (6)

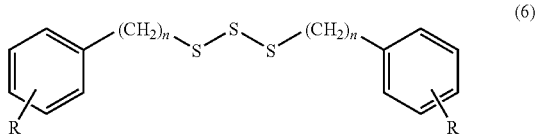

and each n is 1-3; and
R is H, halo, alkyl or halogenated alkyl.

In yet another aspect, the compound has the formula (7)

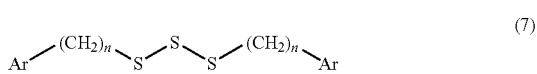

wherein Ar is an optionally substituted thiophene, benzothiophene, pyridine or pyrazine.

Examples of compounds having formula 1-5 include but are not limited to di(fluorobenzyl)trisulfide, di(o-chlorobenzyl)trisulfide, di(methylbenzyl)trisulfide, di(trifluoromethylbenzyl)trisulfide, di(2-phenylethyl)trisulfide, di(2-thiophen-yl-methyl)trisulfide, di(4-pyridin-yl-ethyl)trisulfide, di(2-pyrimidin-yl-ethyl)trisulfide, or di(3-benzothiophen-yl-methyl)trisulfide. In particular examples, the compound is di(p-fluorobenzyl)trisulfide, di(m-methylbenzyl)trisulfide, or di-(p-methylbenzyl)trisulfide.

In another embodiment, the present invention provides methods for making a composition comprising a compound having formula 1-5 as described above, and also provides compositions prepared according to such methods. In one aspect, the present invention provides a method comprising: a) dissolving a compound of claim 1 in a water-soluble organic solvent, a non-ionic solvent, a water-soluble lipid, a cyclodextrin, a vitamin, a fatty acid, a fatty acid ester, a phospholipid, or a combination thereof, to provide a solution; and b) adding saline or a buffer containing 1-10% carbohydrate solution. The organic solvent may be polyethylene glycol (PEG), an alcohol, N-methyl-2-pyrrolidone, N,N-dimethylformamide, N,N-dimethylacetamide, dimethyl sulfoxide, or a combination thereof.

In the above process, the non-ionic surfactant may be polyoxyethyleneglyceroltriricinoleat 35, PEG-succinate, polysorbate 20, polysorbate 80, polyethylene glycol 660 12-hydroxystearate, sorbitan monooleate, poloxamer, ethoxylated persic oil, capryl-caproyl macrogol-8-glyceride, glycerol ester, PEG 6 caprylic glyceride, glycerin, glycol-polysorbate, or a combination thereof. Particular examples of non-ionic surfactants are polyethylene glycol modified CREMOPHOR® (polyoxyethyleneglyceroltriricinoleat 35), CREMOPHOR® EL, hydrogenated CREMOPHOR® RH40, hydrogenated CREMOPHOR® RH60, SOLUTOL® HS (polyethylene glycol 660 12-hydroxystearate), LABRAFIL® (ethoxylated persic oil), LABRASOL® (capryl-caproyl macrogol-8-glyceride), GELUCIRE® (glycerol ester), and SOFTIGEN® (PEG 6 caprylic glyceride).

In the above process, the lipid may be a vegetable oil, a triglyceride, a plant oil, or a combination thereof. For example, the lipid may be castor oil, polyoxyl castor oil, corn oil, olive oil, cottonseed oil, peanut oil, peppermint oil, safflower oil, sesame oil, soybean oil, hydrogenated vegetable oil, hydrogenated soybean oil, a triglyceride of coconut oil, palm seed oil, and hydrogenated forms thereof, or a combination thereof.

In the above process, the vitamin may be tocopherol; and the fatty acid and fatty acid ester may be oleic acid, a monoglyceride, diglyceride, a mono- or di-fatty acid ester of PEG, or a combination thereof.

In the above process, the cyclodextrin may be alpha-cyclodextrin, beta-cyclodextrin, hydroxypropyl-beta-cyclodextrin, or sulfobutyl ether-beta-cyclodextrin. The phospholipid may be soy phosphatidylcholine, or distearoyl phosphatidylglycerol, and hydrogenated forms thereof, or a combination thereof. Furthermore, the carbohydrate in the above process may comprise dextrose.

In yet another embodiment, the present invention provides methods for preparing a compound of formula 1-2 as described above, comprising: a) contacting N-trimethylsilyl imidazole with sulfur dichloride in a halogenated solvent to provide diimidazolylsulfide; and b) contacting said diimidazolylsulfide with mercaptan. In one example, the halogenated solvent is dichloromethane.

In one aspect, N-trimethylsilyl imidazole in hexane is contacted with sulfur dichloride in dichloromethane. In another aspect, sulfur dichloride as a neat compound is contacted with N-trimethylsilyl imidazole in hexane and dichloromethane. In yet another aspect, the methods further comprise recrystallizing the trisulfide. In one example, the trisulfide is recrystallized in n-hexanes, hexanes, heptane, petroleum ether or a combination thereof.

In another embodiment, the present invention provides a pharmaceutical composition comprising a compound having formula 1-5 as described above, and a pharmaceutically acceptable excipient. Such compounds and pharmaceutical compositions thereof may be used for ameliorating or treating neuroblastoma. Thus, the present invention also provides methods for ameliorating or treating neuroblastoma, comprising administering to a system or a subject in need thereof an effective amount of a compound having formula 1-5 or a pharmaceutical composition thereof and optionally with an antiproliferative agent, whereby said neuroblastoma is ameliorated or treated.

The present invention also provides methods for ameliorating or treating a condition comprising administering to a subject or a system in need thereof any compound having formula 1-5 or a pharmaceutical composition thereof, wherein said compound may be dibenzyltrisulfide, di(p-chlorobenzyl)trisulfide, (p-chlorobenzyl)benzyltrisulfide, di(p-nitrobenzyl)trisulfide, di(3-phenyl-2-propenyl)-trisulfide, diphenyltrisulfide, or di(p-t-butylphenyl)trisulfide. The subject may be a human or an animal such as a mammal. The system may be a cell or tissue, or other systems where compounds may be administered in vitro.

In one embodiment, the present invention provides methods for treating or ameliorating a cell proliferative disorder other than neuroblastoma, comprising administering to a system or a subject in need thereof an effective amount of any compound having formula 1-5 or a pharmaceutical composition thereof and optionally with an antiproliferative agent, whereby said cell proliferative disorder in said system or subject is ameliorated or treated. The present invention also provides methods for reducing or inhibiting cell proliferation or for inducing cell death. The present invention further provides methods for inducing apoptosis. In particular examples, the compound used in the methods of the present invention is dibenzyltrisulfide, di(p-fluorobenzyl)trisulfide, di(p-methylbenzyl)trisulfide or di(m-methylbenzyl)trisulfide, and optionally with an antiproliferative agent.

In one aspect, cell proliferation is reduced, or said cell death is induced. The cell proliferative disorder may be a tumor or a cancer including but not limited to leukemia, lymphoma, lung cancer, colon cancer, CNS cancer, melanoma, ovarian cancer, renal cancer, prostate cancer, breast cancer, head-neck cancer, pancreatic cancer, or renal cancer. In another aspect, cell apoptosis is induced. In another aspect, tubulin assembly or disassembly is disrupted, or G2/M progression of the cell cycle, cell mitosis, or a combination thereof, is inhibited. In yet another aspect, endothelial cell proliferation, angiogenesis, or a combination thereof, is inhibited.

In another embodiment, the present invention provides methods for ameliorating or treating restenosis, comprising administering to a subject in need thereof an effective amount of any compound having formula 1-5 or a pharmaceutical composition thereof, whereby restenosis in said subject is ameliorated or treated. The restenosis may be associated with neointimal hyperplasia. The compounds may be administered via oral or parental administration, or via a stent. In yet another embodiment, the present invention provides a pharmaceutical composition for the treatment of a cell proliferative disorder, comprising any compound having formula 1-5, and a pharmaceutically acceptable excipient.

MODES OF CARRYING OUT THE INVENTION

Figure 1A:
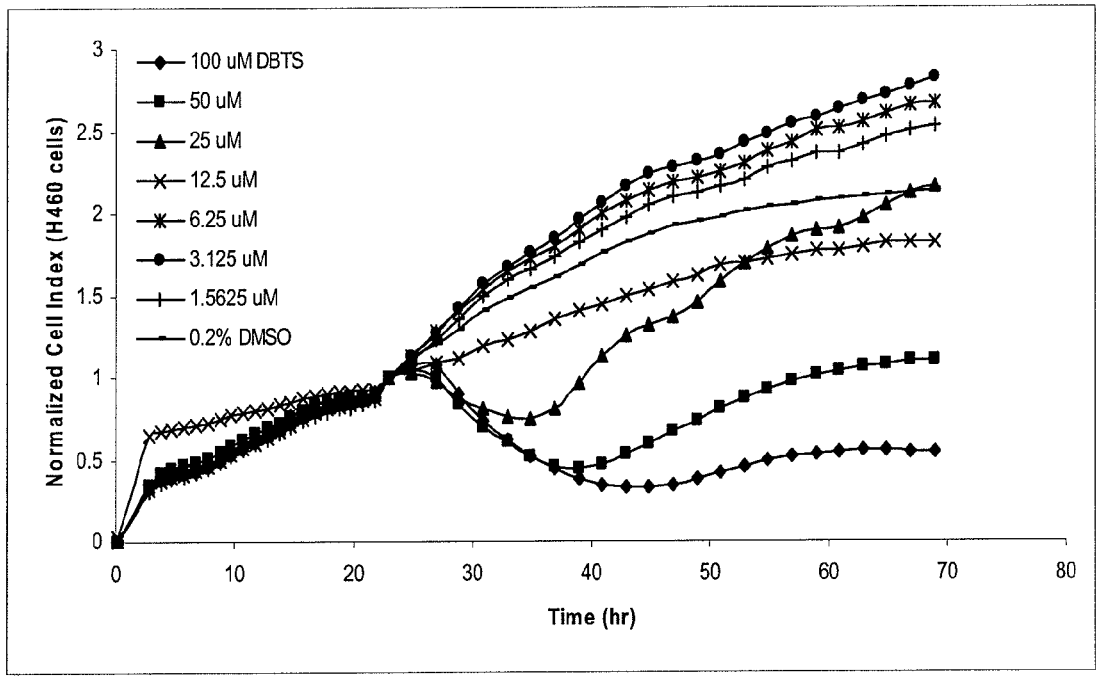
FIGS. 1A-C show the responses of H460 cells (non-small cell lung cancer line) to different concentrations of DBTS, colcemid, and paclitaxel, respectively, as determined on Real-Time Electronic Sensing System (RT-CES system).

For clarity of disclosure, and not by way of limitation, the detailed description of the invention is divided into the subsections that follow.

A. Definition

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition incorporated herein by reference.

As used herein, "a" or "an" means "at least one" or "one or more".

The term "alkyl" as used herein refers to saturated hydrocarbon groups in a straight, branched, or cyclic configuration and particularly contemplated alkyl groups include lower alkyl groups (i.e., those having ten or less carbon atoms). Exemplary alkyl groups are methyl, ethyl, propyl, isopropyl, butyl, sec-butyl, tertiary butyl, pentyl, isopentyl, hexyl, etc. The term "alkenyl" as used herein refers to an alkyl as defined above and having at least one double bond. Thus, particularly contemplated alkenyl groups include straight, branched, or cyclic alkenyl groups having two to ten carbon atoms (e.g., ethenyl, propenyl, butenyl, pentenyl, etc.). Similarly, the term "alkynyl" as used herein refers to an alkyl or alkenyl as defined above and having at least one triple bond. Especially contemplated alkynyls include straight, branched, or cyclic alkynes having two to ten total carbon atoms (e.g., ethynyl, propynyl, butynyl, etc.).

The term "cycloalkyl" as used herein refers to a cyclic alkane (i.e., in which a chain of carbon atoms of a hydrocarbon forms a ring), preferably including three to eight carbon atoms. Thus, exemplary cycloalkanes include cyclopropyl, cyclobutyl, cyclopentyl, cyclohexyl, cycloheptyl, and cyclooctyl. Cycloalkyls also include one or two double bonds, which form the "cycloalkenyl" groups. Cycloalkyl groups are also further substituted by alkyl, alkenyl, alkynyl, halo and other general groups.

The term "aryl" or "aromatic moiety" as used herein refers to an aromatic ring system, which may further include one or more non-carbon atoms. Thus, contemplated aryl groups include (e.g., phenyl, naphthyl, etc.) and pyridyl. Further contemplated aryl groups may be fused (i.e., covalently bound with 2 atoms on the first aromatic ring) with one or two 5- or 6-membered aryl or heterocyclic group, and are thus termed "fused aryl" or "fused aromatic".

As also used herein, the terms "heterocycle", "cycloheteroalkyl", and "heterocyclic moieties" are used interchangeably herein and refer to any compound in which a plurality of atoms form a ring via a plurality of covalent bonds, wherein the ring includes at least one atom other than a carbon atom. Particularly contemplated heterocyclic bases include 5- and 6-membered rings with nitrogen, sulfur, or oxygen as the non-carbon atom (e.g., imidazole, pyrrole, triazole, dihydro pyrimidine, indole, pyridine, thiazole, tetrazole etc.). Further contemplated heterocycles may be fused (i.e., covalently bound with two atoms on the first heterocyclic ring) to one or two ring or heterocycle, and are thus termed "fused heterocycle" or "fused heterocyclic base" or "fused heterocyclic moieties" as used herein.

The term "alkoxy" as used herein refers to straight or branched alkyl connecting to an oxygen atom called alkoxides, wherein the hydrocarbon portion may have any number of carbon atoms, may further include a double or triple bond and may include one or two oxygen, sulfur or nitrogen atoms in the alkyl chains. For example, suitable alkoxy groups include methoxy, ethoxy, propyloxy, isopropoxy, methoxyethoxy, etc. Similarly, the term "alkylthio" refers to straight or branched chain alkylsulfides, wherein the hydrocarbon portion may have any number of carbon atoms, may further include a double or triple bond and may include one or two oxygen, sulfur or nitrogen atoms in the alkyl chains. For example, contemplated alkylthio groups include methylthio, ethylthio, isopropylthio, methoxyethylthio, etc.

Likewise, the term "alkylamino" refers to straight or branched alkylamines, wherein the amino nitrogen "N" can be substituted by one or two alkyls and the hydrocarbon portion may have any number of carbon atoms and may further include a double or triple bond. Furthermore, the hydrogen of the alkylamino may be substituted with another alkyl group. Therefore, exemplary alkylamino groups include methylamino, dimethylamino, ethylamino, diethylamino, etc.

The term "aryloxy" as used herein refers to an aryl group connecting to an oxygen atom, wherein the aryl group may be further substituted. For example suitable aryloxy groups include phenyloxy, etc. Similarly, the term "arylthio" as used herein refers to an aryl group connecting to a sulfur atom, wherein the aryl group may be further substituted. For example suitable arylthio groups include phenylthio, etc.

The term "halogen" as used herein refers to fluorine, chlorine, bromine and iodine.

The term "amino acid" as used herein refers to substituted natural and unnatural amino acid with D- or L-configuration or the mixture in which amino and acid groups are used to derivatize the contemplated compounds.

It should further be recognized that all of the above-defined groups may further be substituted with one or more substituents, which may in turn be substituted as well. For example, an "alkyl" as used herein encompasses alkyls substituted with a heteroatom.

The term "substituted" as used herein refers to a replacement of an atom or chemical group (e.g., H, $NH_2$, or OH) with a functional group, and particularly contemplated functional groups include nucleophilic groups (e.g., $-NH_2$, $-OH$, $-SH$, $-NC$, etc.), electrophilic groups (e.g., C(O)OR, C(X)OH, etc.), polar groups (e.g., $-OH$), non-polar groups (e.g., heterocycle, aryl, alkyl, alkenyl, alkynyl, etc.), ionic groups (e.g., $-NH_3^+$), and halogens (e.g., $-F$, $-Cl$), NHCOR, $NHCONH_2$, $OCH_2COOH$, $OCH_2CONH_2$, $OCH_2CONHR$, $NHCH_2COOH$, $NHCH_2CONH_2$, $NHSO_2R$, $OCH_2$-heterocycles, $PO_3H$, $SO_3H$, amino acids, and various combinations known in the art. Moreover, the term "substituted" also includes multiple degrees of substitution, and where multiple substituents are disclosed or claimed, the substituted compound can be independently substituted by one or more of the disclosed or claimed substituent moieties.

The term "organo sulfur derivative" as used herein refers to an organic compound containing two or more "S" atoms. The term "disulfide", "trisulfide", "tetrasulfide" or pentasulfide" as used herein refers to a moiety where two, three, four, or five sulfur atoms connect in a linear chain (—S—S—S—), where one or two or three of them may be further oxidized into S=O or $SO_2$, and where the di-, tri-, tetra- and penta-sulfide derivatives are substituted with two functional, aryl, alkenyl, heterocyclic groups or substituents at the two ends of the di-, tri-, tetra- and penta-sulfide (R—S—(S)$_{0-3}$—S—R). Two or more trisulfide (—S—S—S—) moieties may be connected together by an aromatic or linear chain, which also refers to "trisulfide" or organo sulfide. One or two trisulfide or organo sulfide moieties may be connected together to form cyclic ring systems.

B. Substituted Organo Sulfur Derivatives and Pharmaceutical Compositions Thereof The present invention compounds having formula

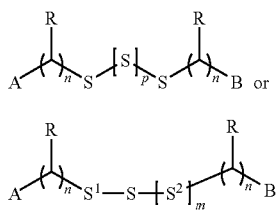
(1)

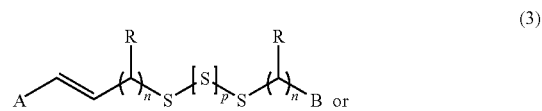
(2)

wherein A and B are the same or different, and are independently an optionally substituted aryl, heteroaryl, or a 5-14 membered ring which may be monocyclic or multicyclic and optionally containing a heteroatom;

each S is optionally in the form of an oxide;

$S^1$ and S2 are independently S, SO or $SO_2$;

each R is H, halogen, carboxyl, cyano, amino, amido, an amino acid, an inorganic substituent, $SR^1$, $OR^1$ or $R^1$, wherein each $R^1$ is alkyl, alkenyl, alkynyl, aryl, heteroaryl, a carbocyclic ring or a heterocyclic ring, each of which is optionally substituted and may contain a heteroatom;

m, n and p are independently 0-3;

or a compound having formula (3) or (4):

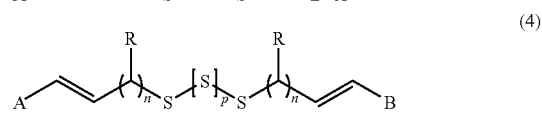
(3)

(4)

wherein A, B, R, S, n and p are as defined above;

or a compound having formula (5):

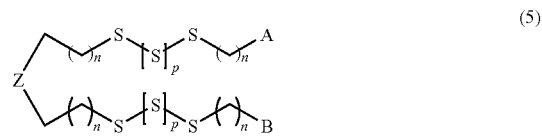
(5)

wherein A, B, S, n and p are as defined above; and

Z is $(CR^1_2)_q$ or $(CR^1=CR^1)_q$* wherein q is 0-3 and the * represents that C=C may be replaced with alkynyl, O, S, NR; or Z is an optionally substituted aryl, heteroaryl or heterocyclic ring;

wherein A and B together may form a cyclic ring system;

and a pharmaceutically acceptable salt, ester, prodrug or metabolite thereof;

provided said compound is not dibenzyltrisulfide, di(p-chlorobenzyl)trisulfide, (p-chlorobenzyl)benzyltrisulfide, di(p-nitrobenzyl)trisulfide, di(3-phenyl-2-propenyl)-trisulfide, diphenyltrisulfide, or di(p-t-butylphenyl)trisulfide.

In other embodiments, each R in the above formula 1-5 may be a non-interfering substituent. In general, a "noninterfering substituent" is a substituent whose presence does not destroy the ability of a compound to behave as a therapeutic agent. For example, a non-interfering substituent may improve potency and PK properties. In another example, the non-interfering substituent may reduce toxicity. Suitable noninterfering substituents include halo, nitro, carboxyl, alkyl, alkenyl, alkynyl, aryl, arylalkyl, arylalkenyl, alkoxy, alkylthio, arylalkynyl, heterocycles, amino acids, each of which may further be substituted with one or more non-interfering substituents. Noninterfering substituents may also include COOR, SR, OR, wherein R is also a non-interfering substituent, as defined above.

In the above formula 1-5, A and B may independently be

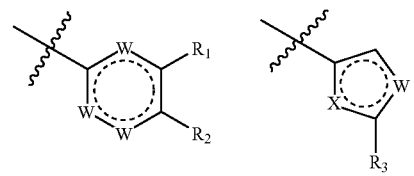

-continued

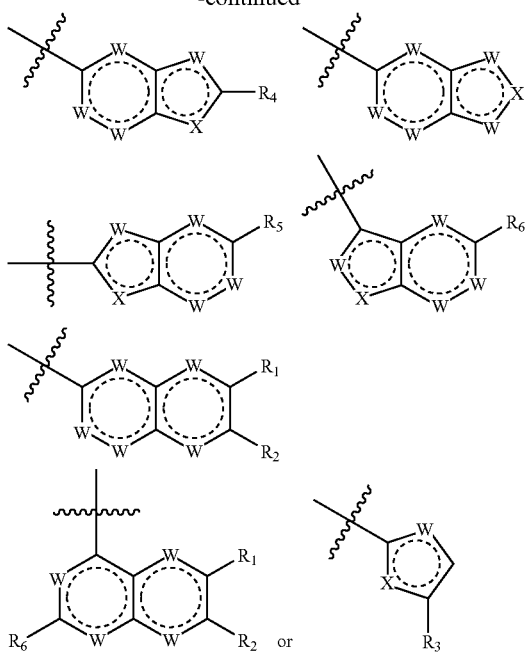

where X and W are independently S, O, NR$_7$, CR$_7$;

or one W in a 6-membered monocyclic or bicyclic ring may be a bond; and each R$_1$, R$_2$, R$_3$, R$_4$, R$_5$, R$_6$, R$_7$ is as previously defined.

In other embodiments, each R$_1$, R$_2$, R$_3$, R$_4$, R$_5$, R$_6$, R$_7$ may be a polar or non-polar substituent. In other examples, each R$_1$, R$_2$, R$_3$, R$_4$, R$_5$, R$_6$, R$_7$ may be a nucleophilic or electrophilic non-interfering substituent.

The present invention also encompasses compounds having formula 1-5, as well as their salts and prodrugs. Such salts, for example, may be formed from a positively charged substitute group (e.g. an amino group on A and/or B) on a compound and a pharmaceutically suitable anion. Suitable anions include, but not limited to, chloride, bromide, iodide, sulfate, nitrate, phosphate, citrate, methanesulfonate, trifluoroacetate, maleate, and acetate. Pharmaceutically acceptable salts may also be formed from a negatively charged substituted group (e.g., carboxylate group on A and/or B) on a compound and a cation. Non-limiting examples of suitable cations are sodium ion, potassium ion, magnesium ion, calcium ion, and a organic ammonium ion such as tetramethylammonium ion, tetrabutylammonium ion, and other organic cations.

The trisulfides may be synthesized following procedures as illustrated in Scheme 1. For example, the aromatic or heterocyclic methylene halides (X═I or Br or Cl) are reacted with thiourea. The resulted isothiouronium halides are treated with sodium hydroxide to provide the corresponding thiol derivatives (Furniss, B. S.; Hannaford, A. J.; Rogers, V.; Smith, P. W. G.; Tatchell, A. R. *Vogel's Textbook of Practical Organic Chemistry*, Longman Group Limited, London, 1978, pp 582-583).

Scheme 1. Synthetic methods for the symmetric and unsymmetric trisulfides

Synthesis of thiol derivatives

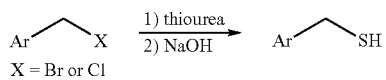

Method A: Synthesis of symmetric trisulfides

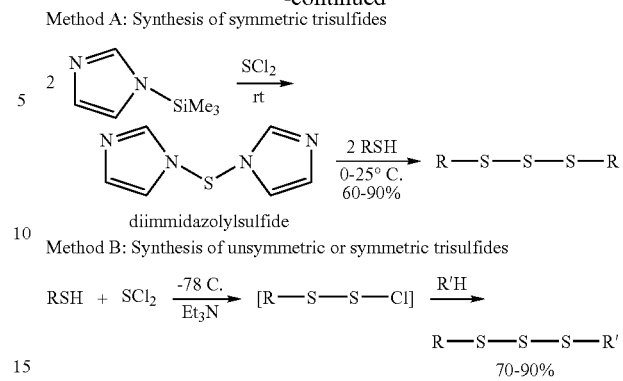

Method B: Synthesis of unsymmetric or symmetric trisulfides $$RSH + SCl_2 \xrightarrow[Et_3N]{-78\ C.} [R-S-S-Cl] \xrightarrow{R'H}$$

$$R-S-S-S-R'$$
70-90%

The symmetric trisulfide derivatives may be synthesized using Method A. In Method A, N-trimethylsilylimidazole is reacted with sulfur dichloride. The resulting diimidazolylsulfide is then reacted with thiol to give the corresponding trisulfides. Method B can be used to synthesize symmetric and asymmetric trisulfides. In Method B, the first thiol is reacted with sulfur dichloride quantitatively at low temperature. The resulting intermediate thiosulfenyl chloride is then reacted with the second thiol to provide the desired asymmetric or symmetric trisulfide, depending on the thiol used in the second step.

The representative aromatic methylene thiols 1-6 (Scheme 2) may be synthesized using the similar procedure as described in Vogel's Practical Organic Chemistry, pp 582-583. In addition, symmetric trisulfide derivatives 7-32 (Scheme 2) were synthesized by Method A similar to the reported procedure (Banerji, A.; Kalena, G. P. *Tetrahedron Letters* 1980, 21, 3003-3004). For example, sulfur dichloride (14 mmol) in anhydrous hexanes or dichloromethane was added to a stirred solution of N-trimethylsilylimidazole (28 mmol) in hexanes at room temperature. After stirring for 30 minutes, the reaction mixture was cooled to 0° C., and a solution of designated thiol (28 mmol) in anhydrous hexanes was added dropwise for a period of 30 minutes. The reaction mixture was stirred for 30 minutes, and the precipitated imidazole by-product was filtered off. The filtrate was washed with water and brine, and dried over anhydrous sodium sulfate. The solvent was evaporated, and the residue is purified by flash chromatography on a silica gel column using hexanes-ethyl acetate 100:1 to 20:1 as eluents to provide desired trisulfides 7-32 in 60-90% yields. The aromatic trisulfides 33-39 were synthesized by the similar procedure in 30-70% yields.

Di(p-fluorobenzyl)trisulfide (8). Trisulfide 8 was synthesized in 77% yield. The white crystalline was obtained by chromatographic purification followed by recrystallization from hexanes. Silica gel TLC R$_f$=0.46 (40:1 hexanes-ethyl acetate). $^1$H NMR (499.1 MHz, CDCl$_3$) δ 4.00 (s, 4H), 7.01 (t, 4H, J=8.8 Hz), 7.27 (dd, 4H, J=8.8, 5.4 Hz); $^{13}$C NMR (125.7 MHz, CDCl$_3$) δ 42.4, 115.6, 115.8, 131.2, 131.3, 132.4, 162.5 (C—F, J=250 Hz); $^{19}$F NMR (376.5 MHz, CDCl$_3$) δ −114.2; ES MS m/z 337/338 (M+Na)$^+$; Anal. Calcd. for C$_{14}$H$_{12}$F$_2$S$_3$: C, 53.48; H, 3.85; S, 30.59. Found: C, 53.16; H, 4.22; S, 30.24.

Di(p-chlorobenzyl)trisulfide (9). Trisulfide 9 was synthesized in 90% yield. The white crystalline was obtained by chromatographic purification followed by recrystallization from hexanes. Silica gel TLC R$_f$=0.45 (40:1 hexanes-ethyl acetate). $^1$H NMR (499.1 MHz, CDCl$_3$) δ 3.98 (s, 4H), 7.22 (d, 4H, J=8.4 Hz), 7.29 (d, 4H, J=8.4 Hz).

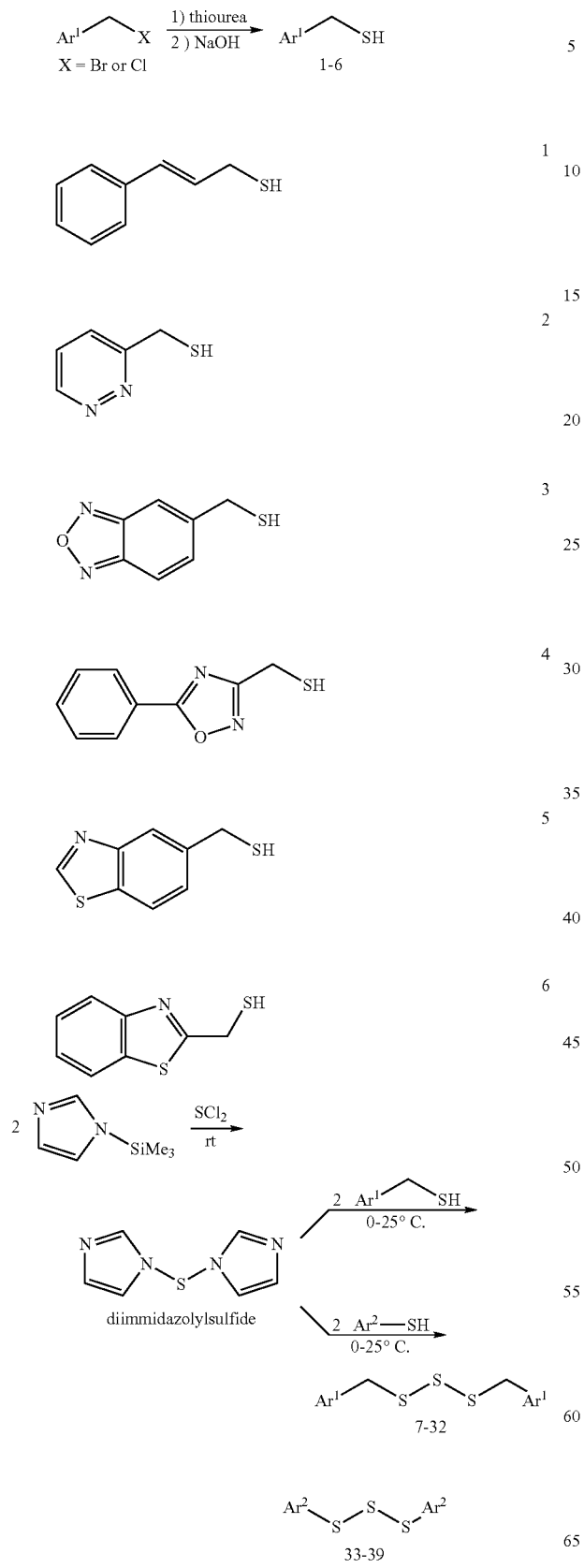
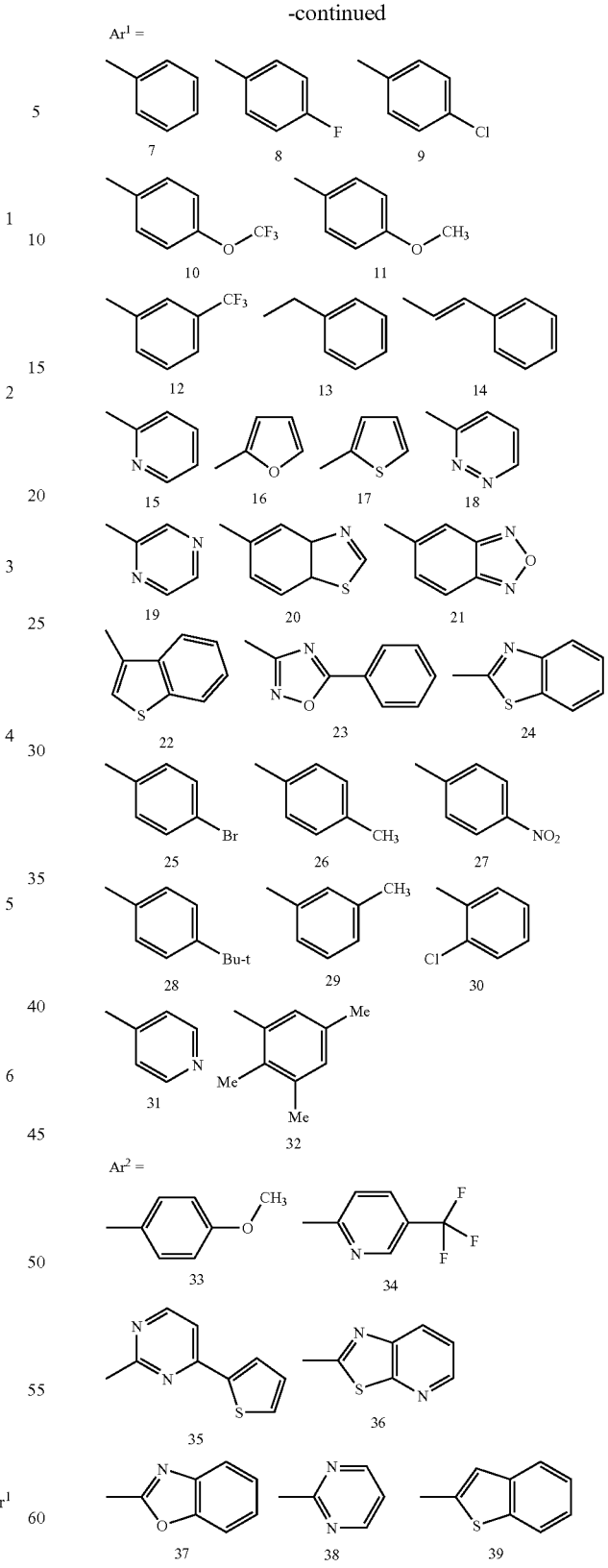
Di(m-trifluoromethylbenzyl)trisulfide (12). Trisulfide 12 was synthesized in 99% yield. The white crystalline was obtained by chromatographic purification followed by recrystallization from hexanes. Silica gel TLC $R_f$=0.33 (40:1 hexanes-ethyl acetate). $^1$H NMR (499.1 MHz, CDCl$_3$) δ 4.04 (s, 4H), 7.41-7.49 (m, 4H), 7.51-7.58 (m, 4H).

Di(benzo[B]thiophen-3-yl-methane)trisulfide (22). Trisulfide 22 was synthesized in 45% yield. The white solid was obtained by chromatographic purification. Silica gel TLC R$_f$=0.45 (40:1 hexanes-ethyl acetate). $^1$H NMR (499.1 MHz, CDCl$_3$) δ 3.74 (s, 4H), 7.01 (s, 2H), 7.34-7.45 (m, 4H), 7.75 (d, 2H, J=7.4 Hz), 7.85 (dd, 2H, J=7.8, 1.1 Hz). ES MS m/z 391 (M+H)$^+$, 413 (M+Na)$^+$.

Di(p-bromobenzyl)trisulfide (25). Trisulfide 25 was synthesized in 84% yield. The white crystalline was obtained by chromatographic purification followed by recrystallization from hexanes. Silica gel TLC R$_f$=0.55 (40:1 hexanes-ethyl acetate). $^1$H NMR (499.1 MHz, CDCl$_3$) δ 3.96 (s, 4H), 7.17 (d, 4H, J=8.3 Hz), 7.45 (d, 4H, J=8.3 Hz).

Di(p-methylbenzyl)trisulfide (26). Trisulfide 26 was synthesized in 99% yield. The white crystalline was obtained by chromatographic purification followed by recrystallization from hexanes. Silica gel TLC R$_f$=0.66 (40:1 hexanes-ethyl acetate). $^1$H NMR (499.1 MHz, CDCl$_3$) δ 2.33 (s, 6H), 4.01 (s, 4H), 7.14 (d, 4H, J=8.0 Hz), 7.21 (d, 4H, J=8.0 Hz).

Di(p-t-butylbenzyl)trisulfide (28). Trisulfide 28 was synthesized in 96% yield. The white crystalline was obtained by chromatographic purification followed by recrystallization from hexanes. Silica gel TLC R$_f$=0.50 (40:1 hexanes-ethyl acetate). $^1$H NMR (499.1 MHz, CDCl$_3$) δ 1.30 (s, 18H), 4.02 (s, 4H), 7.25 (d, 4H, J=8.3 Hz), 7.35 (d, 4H, J=8.3 Hz).

Di(o-chlorobenzyl)trisulfide (30). Trisulfide 30 was synthesized in 77% yield. The white crystalline was obtained by chromatographic purification followed by recrystallization from hexanes. Silica gel TLC R$_f$=0.44 (40:1 hexanes-ethyl acetate). $^1$H NMR (499.1 MHz, CDCl$_3$) δ 4.17 (s, 4H), 7.23-7.28 (m, 4H), 7.35-7.43 (m, 4H).

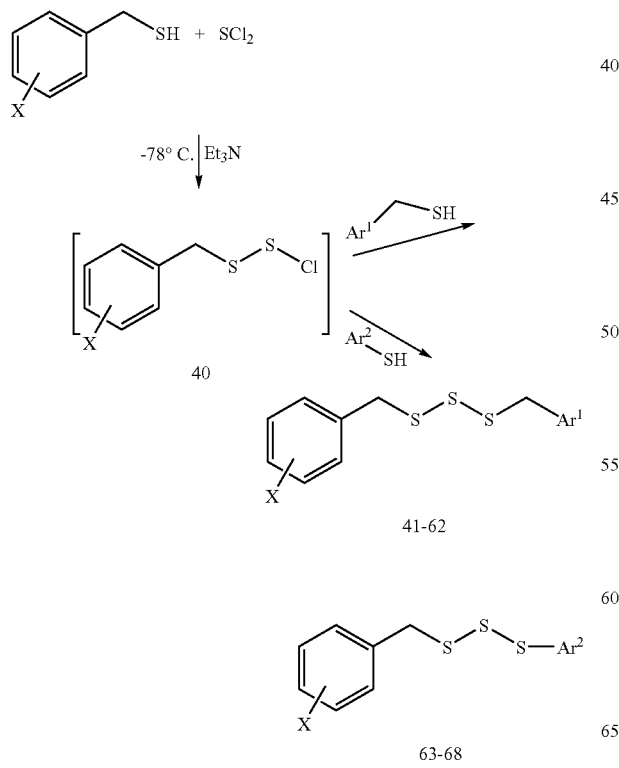

Scheme 3. Synthetic the symmetric trisulfides by Method B

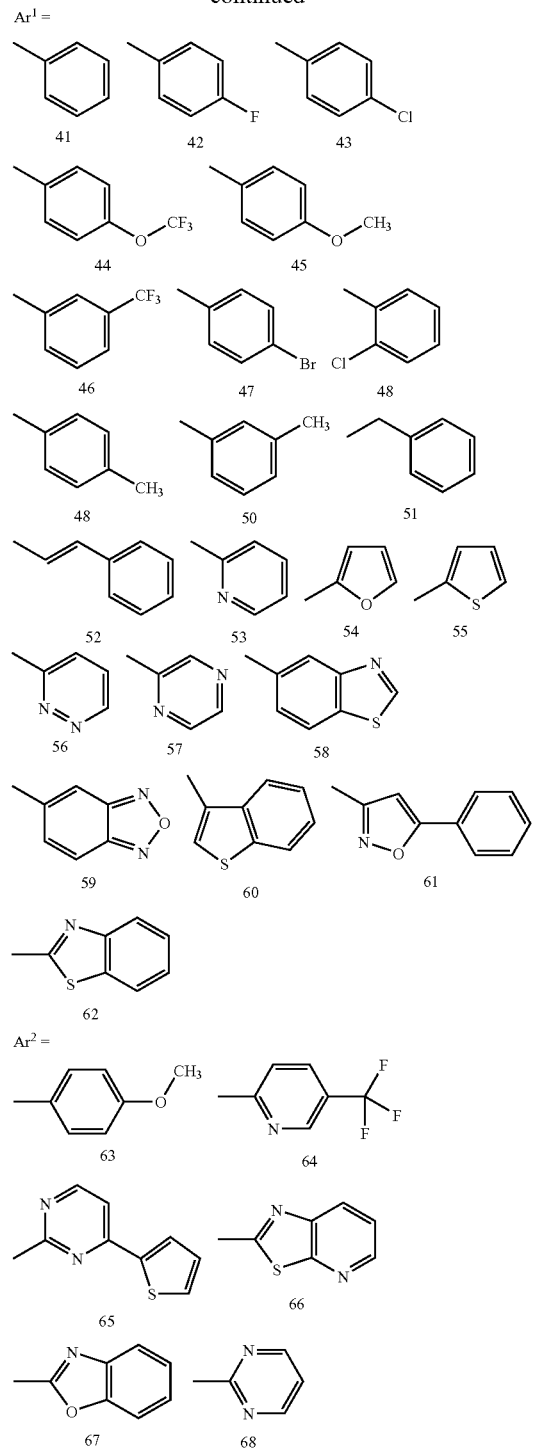

Di(2,4,6-trimethylbenzyl)trisulfide (32). Trisulfide 32 was synthesized in 59% yield. The white crystalline was obtained by chromatographic purification followed by recrystallization from hexanes. Silica gel TLC R$_f$=0.65 (40:1 hexanes-ethyl acetate). $^1$H NMR (499.1 MHz, CDCl$_3$) δ 2.27 (s, 6H), 2.42 (s, 12H), 4.23 (s, 4H), 6.87 (s, 4H).

Di(p-methoxyphenyl)trisulfide (33). Trisulfide 33 was synthesized in 98% yield. The white crystalline was obtained by chromatographic purification followed by recrystallization from hexanes. Silica gel TLC R$_f$=0.32 (20:1 hexanes-ethyl acetate). $^1$H NMR (499.1 MHz, CDCl$_3$) δ 3.80 (s, 4H), 6.81 (d, 4H, J=8.8 Hz), 7.47 (d, 4H, J=8.8 Hz).

Di(4-trifluoromethylpyridin-2-yl)trisulfide (34). Trisulfide 34 was synthesized in 53% yield. The white crystalline was obtained by chromatographic purification followed by recrystallization from hexanes. Silica gel TLC R$_f$=0.61 (10:1 hexanes-ethyl acetate). $^1$H NMR (499.1 MHz, CDCl$_3$) δ 7.70 (d, 4H, J=8.4 Hz), 7.84 (dd, 4H, J=8.4, 2.4 Hz), 8.73 (s, 2H).

The asymmetric trisulfide derivatives listed in Tables 1-8 may be synthesized following similar procedures as for compounds 41-68, using the corresponding thiol.

TABLE 1

Various disubstituted trisulfide derivatives.

TABLE 1-continued

Various disubstituted trisulfide derivatives.

TABLE 2

Various disubstituted trisulfide derivatives.

TABLE 2-continued
Various disubstituted trisulfide derivatives.
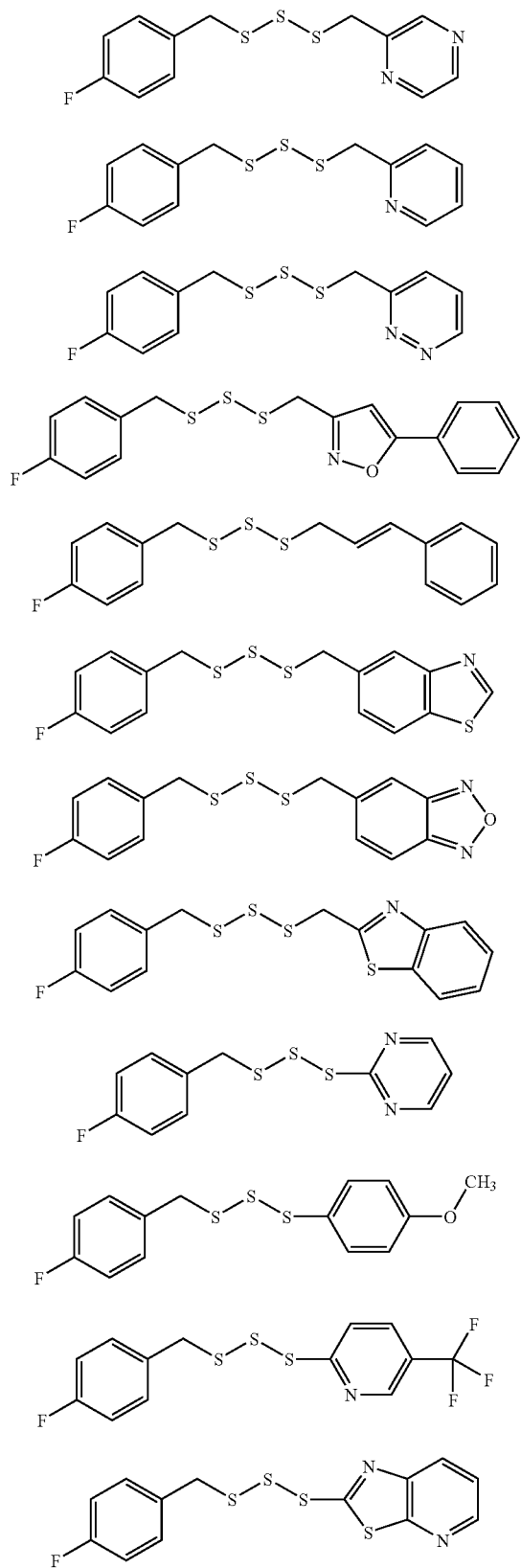
TABLE 2-continued
Various disubstituted trisulfide derivatives.
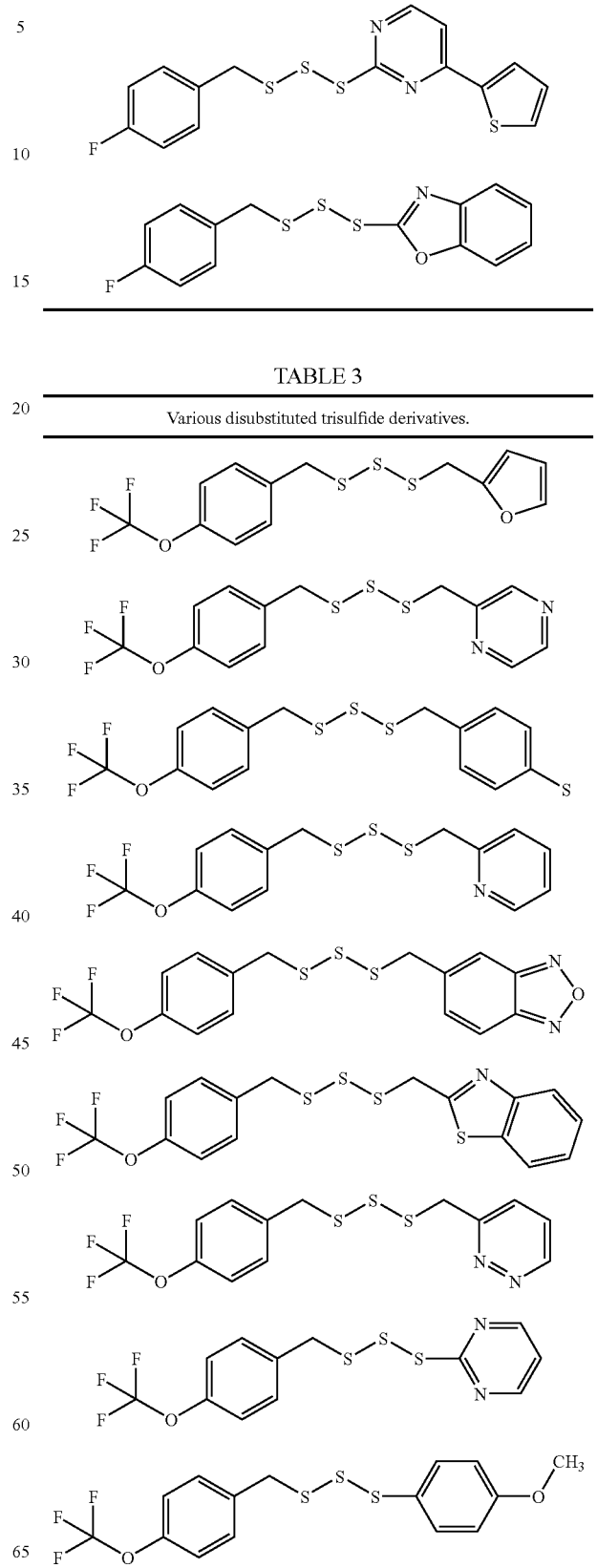
TABLE 3
Various disubstituted trisulfide derivatives.

TABLE 3-continued
Various disubstituted trisulfide derivatives.
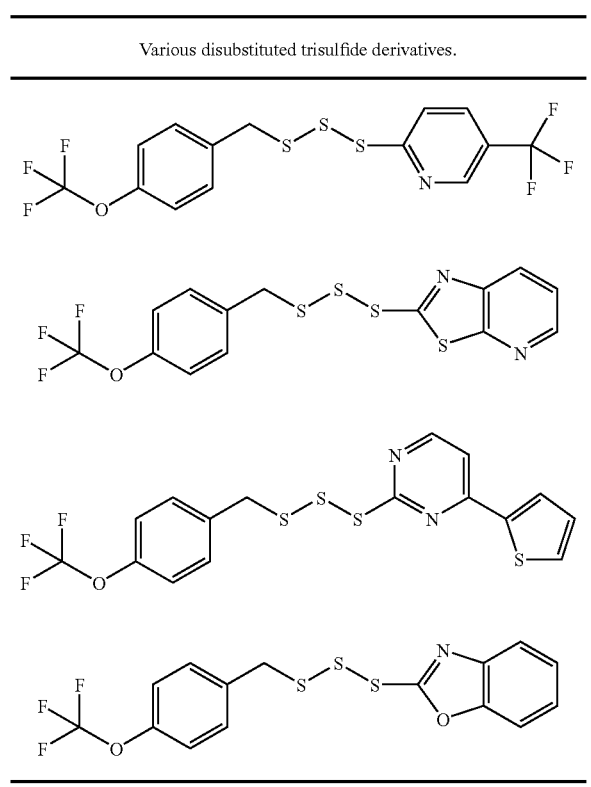
TABLE 4
Various disubstituted trisulfide derivatives.
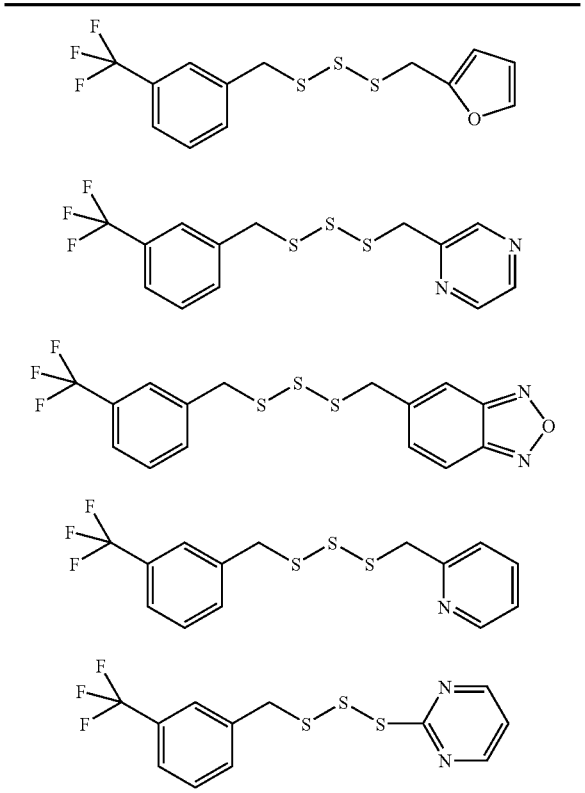
TABLE 4-continued
Various disubstituted trisulfide derivatives.
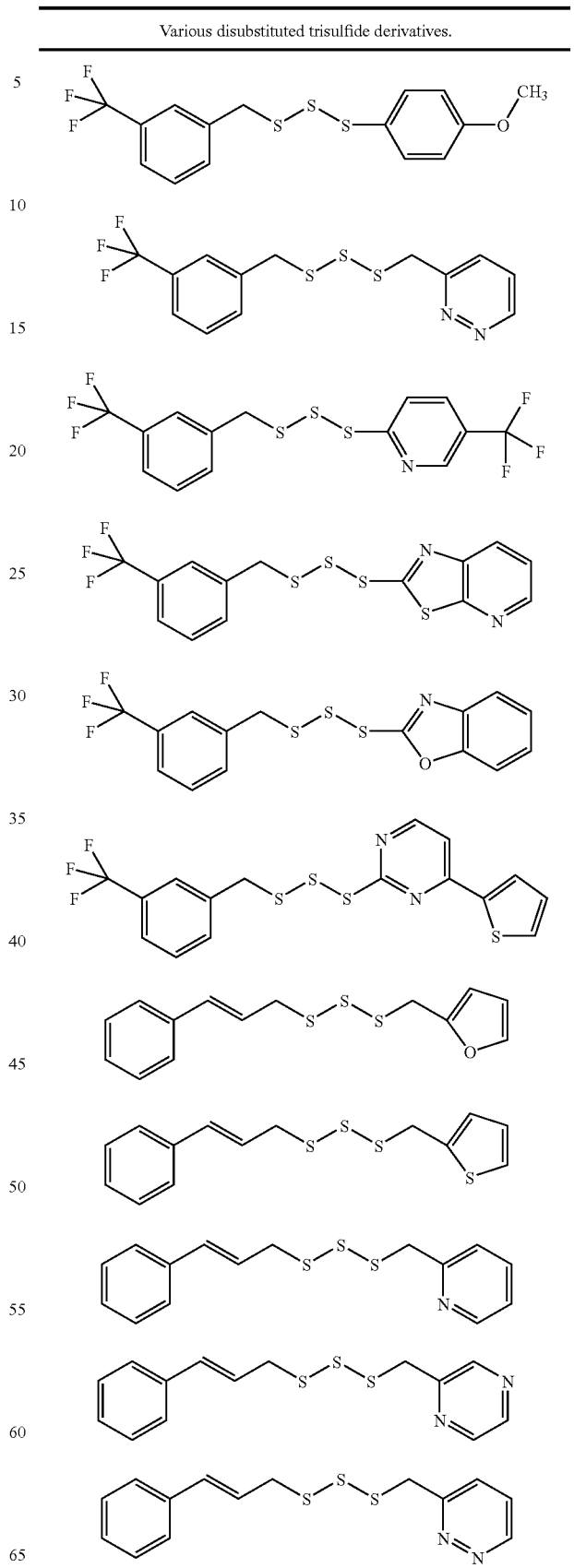

TABLE 4-continued
Various disubstituted trisulfide derivatives.
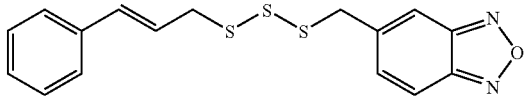
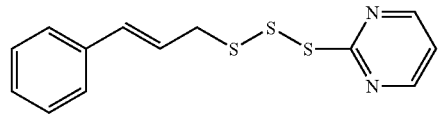
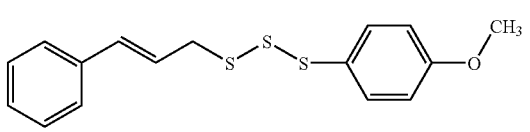
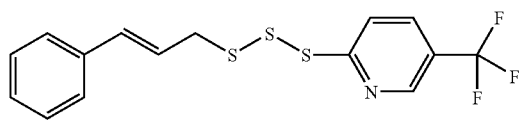
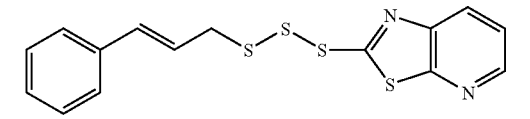
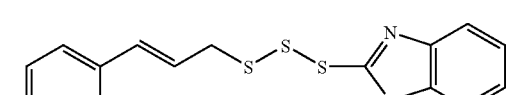
TABLE 5
Various disubstituted trisulfide derivatives.
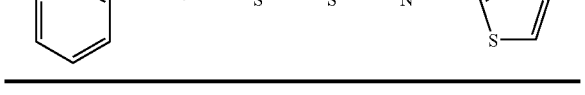
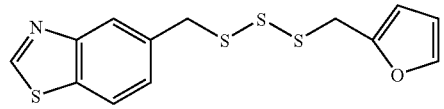
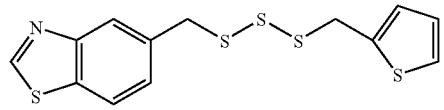
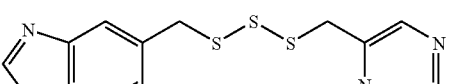
TABLE 5-continued
Various disubstituted trisulfide derivatives.
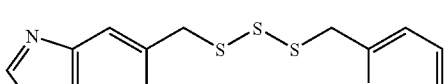
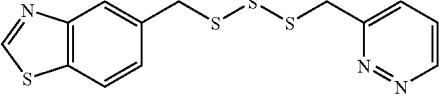
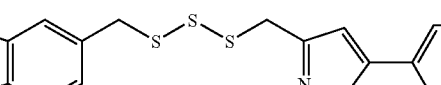
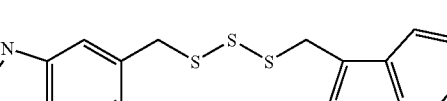
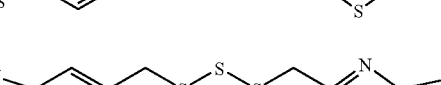
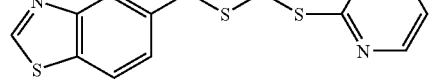
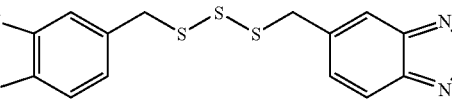
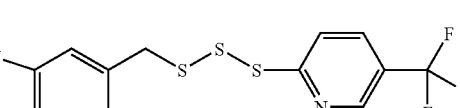
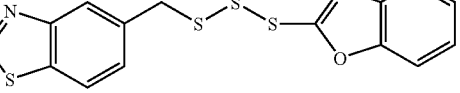
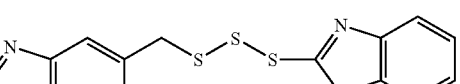

TABLE 6

Various substituted trisulfide derivatives.

TABLE 6-continued

Various substituted trisulfide derivatives.

TABLE 7

Various disubstituted trisulfide derivatives.

TABLE 7-continued
Various disubstituted trisulfide derivatives.
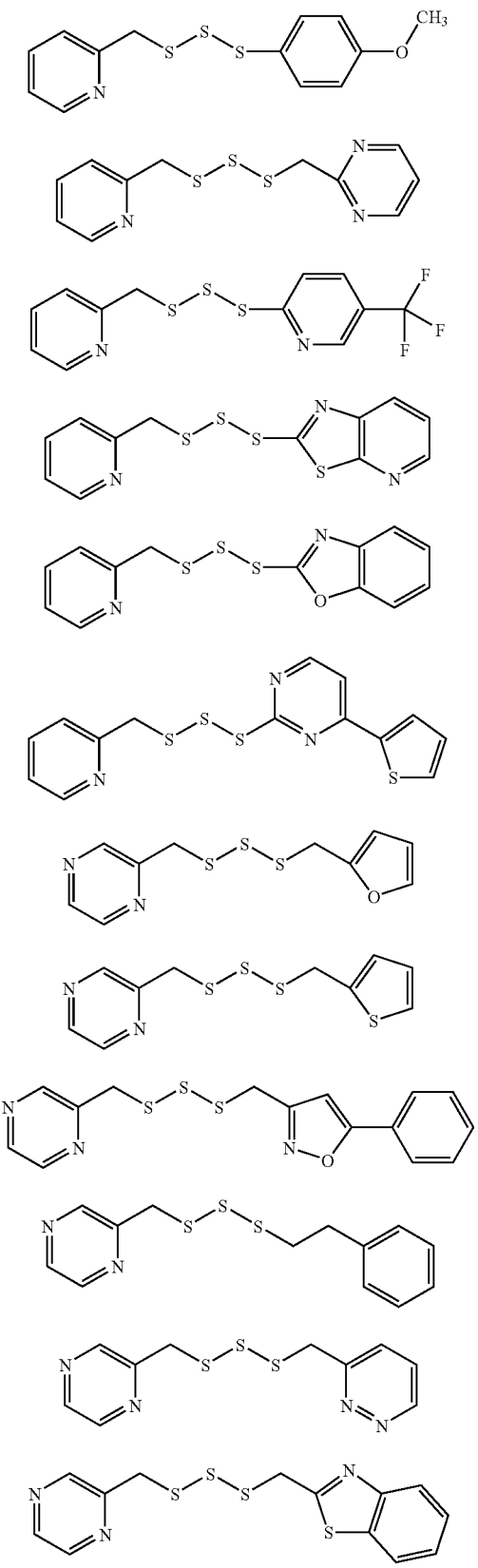
TABLE 7-continued
Various disubstituted trisulfide derivatives.
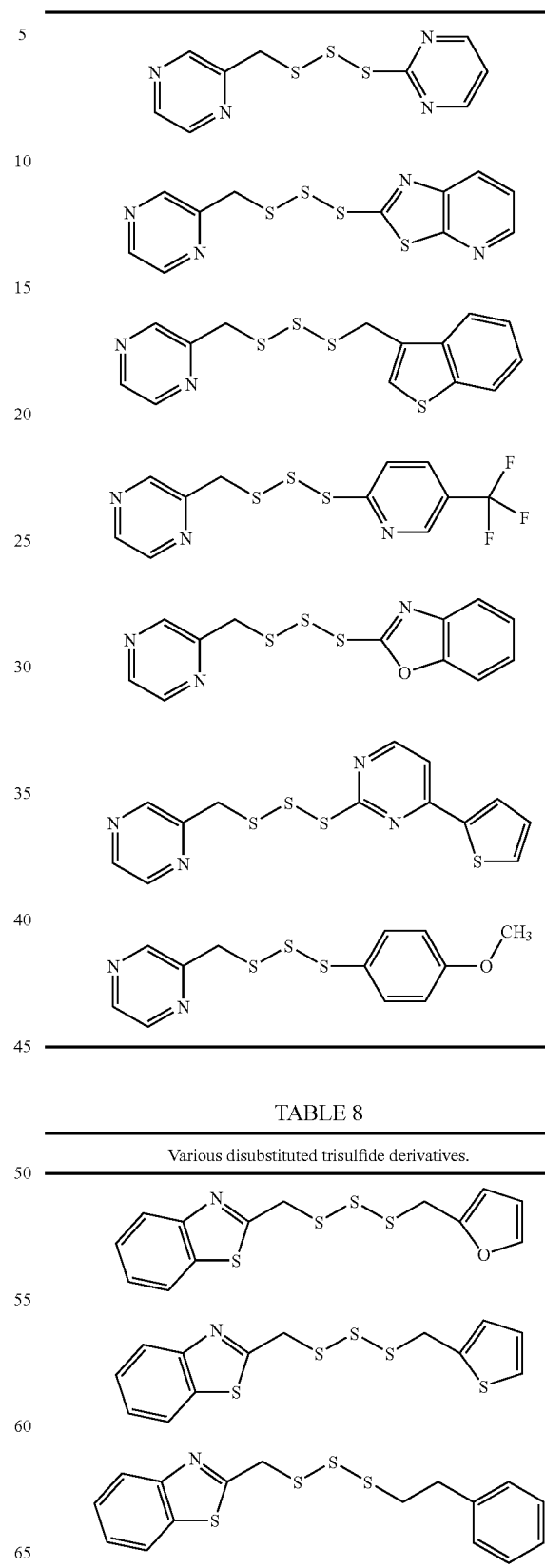
TABLE 8
Various disubstituted trisulfide derivatives.
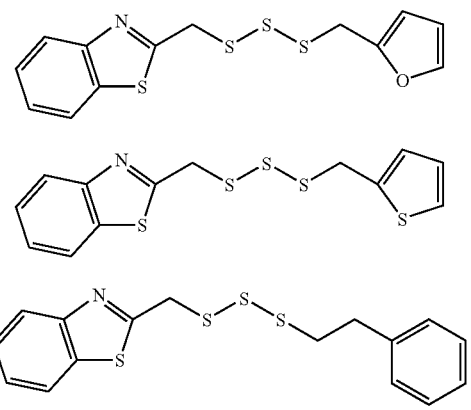

TABLE 8-continued

Various disubstituted trisulfide derivatives.

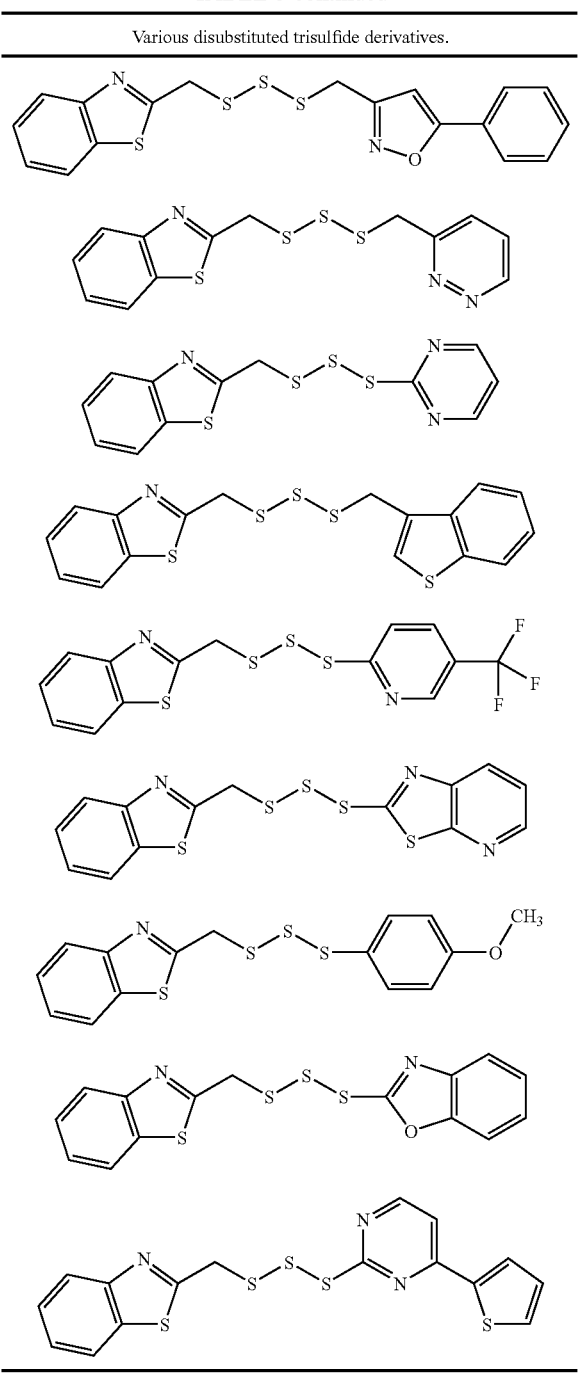

The di-substituted(trisulfide) derivatives listed in Schemes 4 and 5 may be synthesized by similar procedures (Method B). For example, a solution of 1,3-benzenedimethanethiol or 2-butene-1,4-dithiol (10 mmol) and anhydrous pyridine (20 mmol) in 30 mL of diethyl ether is added dropwise over a period of 30 minutes to a cold (−78° C.) stirred solution of sulfur dichloride (20 mmol) in 80 mL of anhydrous diethyl ether. The reaction mixture is stirred for 30 minutes. The corresponding second thiol (20 mmol) and anhydrous pyridine (20 mmol) in 40 mL of diethyl ether is added dropwise over a period of 30 minutes at −78° C., and the reaction mixture is further stirred for an additional 30 minutes. The reaction mixture is washed with water (2 times), 1 N sodium hydroxide solution (2 times), and then water (2 times) until pH is neutral. The organic phase is dried over $CaCl_2$ or anhydrous sodium sulfate, filtered and concentrated. The residue is passed through a short pad of silica gel using hexanes-ethyl acetate as eluent to provide di-substituted trisulfides in 40-90% yields.

Scheme 4. Synthesis of bis(trisulfide) derivativces

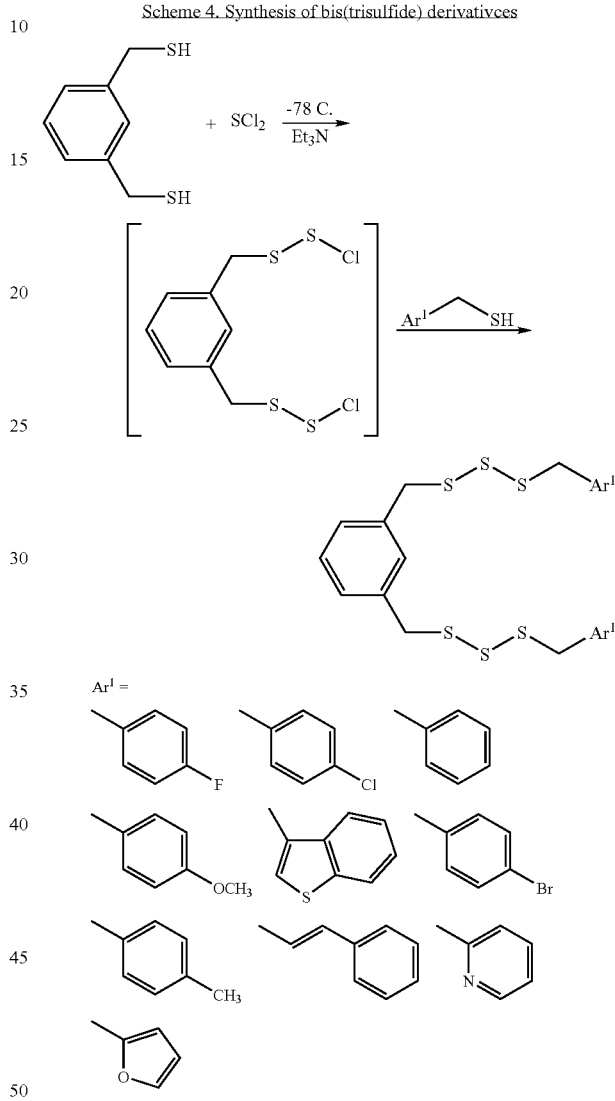

Scheme 5. Synthesis of bis(trisulfide) derivativces

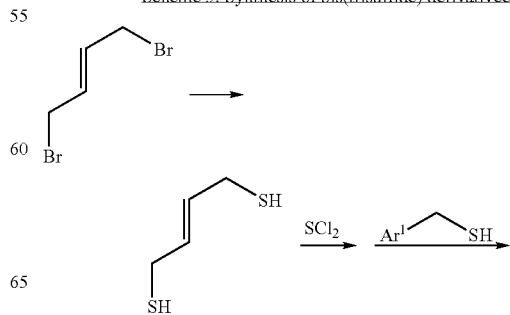

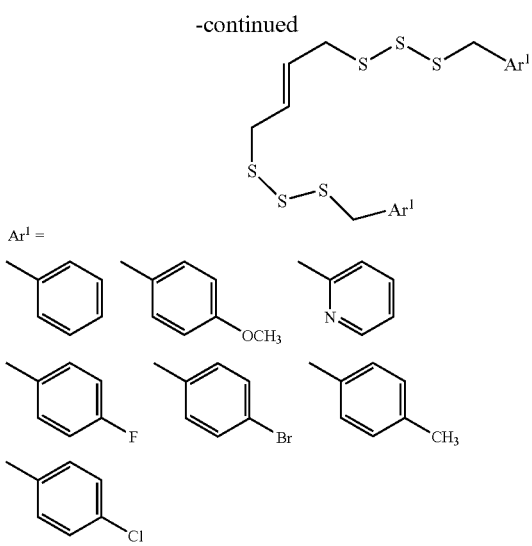

Scheme 6. Synthesis of tri-, tetra- and pentasulfide derivatives

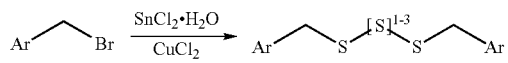

The trisulfide derivatives may be synthesized by the methods described above or by the approach illustrated in Scheme 6. The tetra- and penta-sulfide derivatives are synthesized by the similar strategy based on the reported procedure (Sinha, P.; Jundu, A.; Roy, S.; Prabhakar, S.; Vairamani, M.; Sankar, A. R.; Kunwar, A. C. *Organometallics* 2001, 20, 157-162).

Scheme 7. Synthesis of sulfenic sulfonic thioanhydride, thisulfonate, and disulfonic thioanhydride derivatives

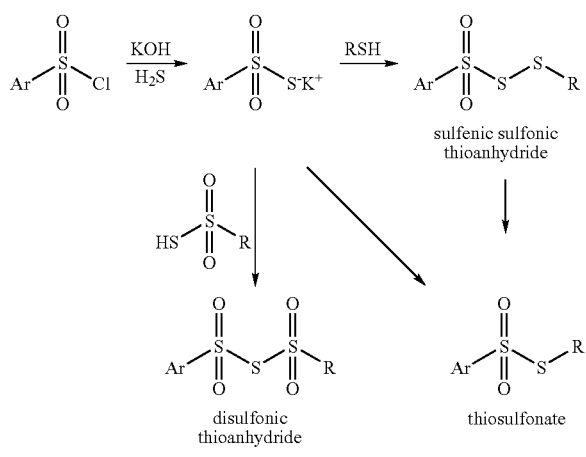

R is aromatic, heteroclic or aliphatic group

The symmetric or asymmetric sulfenic sulfonic thioanhydride derivatives (Scheme 7) can be synthesized based on the reported procedures (Karpp, D. N.; Gleason, J. G.; Ash, D. K. *J. Org. Chem.* 1971, 36, 322-326; and Harpp, D. N.; Ash, D. K.; Smith, R. A. *J. Org. Chem.* 1979, 44, 4135-4140).

The present invention also provides pharmaceutical compositions comprising an effective amount of a compound having formula 1-5 optionally with an antiproliferative agent, and a pharmaceutically acceptable excipient. As used herein, an "effective amount" refers to the amount of the compound which is required to confer a therapeutic effect on the treated subject. The effective amount or dose will vary as recognized by those skilled in the art, depending on the types of tumors treated, route of administration, and possible co-administration with other therapeutic treatments such as use of other anti-tumor agents or radiation therapy.

As used herein, the term "antiproliferative agent" refers to a therapeutic agent that may be used for treating or ameliorating a cell proliferative disorder such as tumors or cancer. Examples of antiproliferative agents include but are not limited to an antineoplastic agent, an alkylating agent, a plant alkaloid, an antimicrobial agent, a sulfonamide, an antiviral agent, a platinum agent, and other anticancer agents known in the art. Particular examples of antiproliferative agents include but are not limited to cisplatin, carboplatin, busulphan, methotrexate, daunorubicin, doxorubicin, cyclophosphamide, mephalan, vincristine, vinblastine, chlorambucil, paclitaxel, gemcitabine, and others known in the art. (See e.g., Goodman & Gilman's, *The Pharmacological Basis of Therapeutics* (9th Ed) (Goodman, et al., eds.) (McGraw-Hill) (1996); and 1999 *Physician's Desk Reference* (1998)).

Any suitable formulation of the compounds described herein may be prepared. In cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts. Pharmaceutically acceptable salts are obtained using standard procedures well known in the art, for example, by a sufficiently basic compound such as an amine with a suitable acid, affording a physiologically acceptable anion. Alkali metal (e.g., sodium, potassium or lithium) or alkaline earth metal (e.g., calcium) salts of carboxylic acids also are made.

The compounds having formula 1-5 as described herein are generally soluble in organic solvents such as chloroform, dichloromethane, ethyl acetate, ethanol, methanol, isopropanol, acetonitrile, glycerol, N,N-dimethylformamide, N,N-dimetheylaceatmide, dimethylsulfoxide, etc. In one embodiment, the present invention provides formulations prepared by admixing a compound having formula 1-5 with a pharmaceutically acceptable carrier. In one aspect, the formulation may be prepared using a method comprising: a) dissolving a compound of claim 1 in a water-soluble organic solvent, a non-ionic solvent, a water-soluble lipid, a cyclodextrin, a vitamin such as tocopherol, a fatty acid, a fatty acid ester, a phospholipid, or a combination thereof, to provide a solution; and b) adding saline our a buffer containing 1-10% carbohydrate solution. In one example, the carbohydrate comprises dextrose. The pharmaceutical compositions obtained using the present methods are stable and useful for animal and clinical applications.

Illustrative examples of water soluble organic solvents for use in the present methods include and are not limited to polyethylene glycol (PEG), alcohols, acetonitrile, N-methyl-2-pyrrolidone, N,N-dimethylformamide, N,N-dimethylacetamide, dimethyl sulfoxide, or a combination thereof. Examples of alcohols include but are not limited to methanol, ethanol, isopropanol, glycerol, or propylene glycol.

Illustrative examples of water soluble non-ionic surfactants for use in the present methods include but are not limited to polyoxyethyleneglyceroltriricinoleat 35, PEG-succinate, polysorbate 20, polysorbate 80, polyethylene glycol 660 12-hydroxystearate, sorbitan monooleate, poloxamer, ethoxylated persic oil, capryl-caproyl macrogol-8-glyceride, glycerol ester, PEG 6 caprylic glyceride, glycerin, glycolpolysorbate, or a combination thereof. Particular examples of non-ionic surfactants are polyethylene glycol modified CREMOPHOR® (polyoxyethyleneglyceroltriricinoleat 35), CREMOPHOR® EL, hydrogenated CREMOPHOR® RH40, hydrogenated CREMOPHOR® RH60, SOLUTOL® HS (polyethylene glycol 660 12-hydroxystearate), LABRAFIL® (ethoxylated persic oil), LABRASOL® (capryl-caproyl macrogol-8-glyceride), GELUCIRE® (glycerol ester), and SOFTIGEN® (PEG 6 caprylic glyceride).

Illustrative examples of water soluble lipids for use in the present methods include but are not limited to vegetable oils, triglycerides, plant oils, or a combination thereof. Examples of lipid oils include but are not limited to castor oil, polyoxyl castor oil, corn oil, olive oil, cottonseed oil, peanut oil, peppermint oil, safflower oil, sesame oil, soybean oil, hydrogenated vegetable oil, hydrogenated soybean oil, a triglyceride of coconut oil, palm seed oil, and hydrogenated forms thereof, or a combination thereof.

Illustrative examples of fatty acids and fatty acid esters for use in the present methods include but are not limited to oleic acid, monoglycerides, diglycerides, a mono- or di-fatty acid ester of PEG, or a combination thereof.

Illustrative examples of cyclodextrins for use in the present methods include but are not limited to alpha-cyclodextrin, beta-cyclodextrin, hydroxypropyl-beta-cyclodextrin, or sulfobutyl ether-beta-cyclodextrin.

Illustrative examples of phospholipids for use in the present methods include but are not limited to soy phosphatidylcholine, or distearoyl phosphatidylglycerol, and hydrogenated forms thereof, or a combination thereof.

One of ordinary skill in the art may modify the formulations within the teachings of the specification to provide numerous formulations for a particular route of administration. In particular, the compounds may be modified to render them more soluble in water or other vehicle. It is also well within the ordinary skill of the art to modify the route of administration and dosage regimen of a particular compound in order to manage the pharmacokinetics of the present compounds for maximum beneficial effect in a patient.

C. Methods of Using Substituted Organo Sulfur Derivatives and Pharmaceutical Compositions Thereof The compounds as described herein may be used as cytotoxic and/or cytostatic agents in treating cancers or other types of proliferative disease. These compounds may function through any type of action mechanisms. For example, the compounds may inhibit G2/M progression of the cell cycle, which might eventually induce apoptosis in tumor cells (see, e.g., Weung, et al. *Biochim. Biophys. Res. Comm.* 1997, 263, 398-404). Some compounds may disrupt tubulin assembly, and other compounds may disrupt tubulin disassembly, which may inhibit cell mitosis and induce cell apoptosis (see, e.g., Panda, et al. *Proc. Natl. Acad. Sci. USA,* 1997, 94, 10560-10564). The compounds may also inhibit endothelial cell proliferation and angiogenesis effect (see, e.g., Witte, et al. *Cancer Metastasis Rev.* 1998, 17, 155-161).

The present invention also provides pharmaceutical compositions for the treatment of a cell proliferative disorder, comprising any compound having formula 1-5, including but not limited to dibenzyltrisulfide, di(p-chlorobenzyl)trisulfide, (p-chlorobenzyl)benzyltrisulfide, di(p-nitrobenzyl)trisulfide, di(3-phenyl-2-propenyl)-trisulfide, diphenyltrisulfide, or di(p-t-butylphenyl)trisulfide.

To practice the method of the present invention, compounds having formula 1-5 and pharmaceutical compositions thereof may be administered orally, parenterally, by inhalation spray, topically, rectally, nasally, buccally, vaginally, via an implanted reservoir, or other drug administration methods. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

A sterile injectable composition, such as a sterile injectable aqueous or oleaginous suspension, may be formulated according to techniques known in the art using suitable dispersing or wetting agents and suspending agents. The sterile injectable preparation may also be a sterile injectable solution or suspension in a non-toxic parenterally acceptable diluent or solvent. Among the acceptable vehicles and solvents that may be employed include mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives, are useful in the preparation of injectables, as are pharmaceutically acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Various emulsifying agents or bioavailability enhancers which are commonly used in the manufacture of pharmaceutically acceptable solid, liquid, or other dosage forms can also be used for the purpose of formulation.

A composition for oral administration may be any orally acceptable dosage form including, but not limited to, tablets, capsules, emulsions and aqueous suspensions, dispersions and solutions. In the case of tablets for oral use, commonly used carriers include lactose and corn starch. Lubricating agents, such as magnesium stearate, can also be added. For oral administration in a capsule form, useful diluents include lactose and dried corn starch. When aqueous suspensions or emulsions are administered orally, the active ingredient can be suspended or dissolved in an oily phase combined with emulsifying or suspending agents. If needed, certain sweetening, flavoring, or coloring agents can be added. A nasal aerosol or inhalation compositions can be prepared according to techniques well-known in the art of pharmaceutical formulation and can be prepared as solutions in, for example saline, employing suitable preservatives (for example, benzyl alcohol), absorption promoters to enhance bioavailability, and/or other solubilizing or dispersing agents known in the art.

In addition, the compounds having formula 1-5 may be administered alone or in combination with other anticancer agents for the treatment of various cancers or conditions. Combination therapies according to the present invention comprise the administration of at least one compound of the present invention or a functional derivative thereof and at least one other pharmaceutically active ingredient. The active ingredient(s) and pharmaceutically active agents may be administered separately or together. The amounts of the active ingredient(s) and pharmaceutically active agent(s) and the relative timings of administration will be selected in order to achieve the desired combined therapeutic effect.

In one embodiment, the present invention is directed to a method of treating or ameliorating a cancer of a tissue or organ, including but not limited to leukemia, lymphoma, lung cancer, colon cancer, CNS cancer, melanoma, ovarian cancer, renal cancer, prostate cancer, breast cancer, pancreatic cancer, renal cancer, and other types of proliferative disease comprising administering a therapeutically effective amount of a compound having formula 1-5.

In another embodiment, the present invention is directed to a method of treatment of restenosis after coronary stenting for patients with coronary artery diseases with a compound having formula 1-5, such as dibenzyl trisulfide and other substituted trisulfide derivatives. One of the main causes of restenosis after coronary stenting for patients with coronary artery disease is neointimal hyperplasia which may result from the proliferation and migration of smooth-muscle cells and extracellular matrix productions (see, for example, "Pathology of acute and chronic coronary stenting in humans", by Farb, A., Sangiorgi, G., Certer, A. J., et al. *Circulation,* 1999, 99, 44-52). Compounds that have anti-proliferation capability may have an effect in reducing the risk of clinical and angiographic restenosis when such compounds are delivered with a suitable means (see, for example, "A polymer-based, paclitaxel-eluting stent in patients with coronary artery disease", by Stone, G. W., Ellis, S. G., Cox, D. A, et al. *New Engl. J. Med.,* 2004, 350, 221-231). Thus, dibenzyl trisulfide and other compounds having formula 1-5 may also be useful in inhibiting proliferation of the cells involved in neointimal hyperplasia and thus reducing the incidence of neointimal hyperplasia and restenosis.

Various methods may be used to effectively deliver compounds having formula 1-5 to their target, such as cells. For example, a composition comprising dibenzyl trisulfide, or a another compound having formula 1-5 may be administered orally, parenterally, or via an implanted reservoir. In other examples, the approaches described in the following papers hereby incorporated by reference, may also be used: "A polymer-based, paclitaxel-eluting stent in patients with coronary artery disease", by Stone, G. W., Ellis, S. G., Cox, D. A. et al. *New Engl. J. Med.* 2004, 350, 221-231; "A randomized comparison of a sirolimus-eluting stent with a standard stent for coronary revascularization", by Morice, M.-C., Serruys, P. W., Sousa, J. E., et al. *New Engl. J. Med.* 2002, 346, 1773-1780; "Sirolimus-eluting stents versus standard stents in patients with stenosis in a native coronary artery", by Moses, J. W., Leon, M. B., Popma, J. J., et al, *New Engl. J. Med.* 2003, 349, 1315-1323.

The anticancer efficacy of dibenzyl trisulfide and substituted organo sulfur analogues described above may be preliminarily screened in vitro using a penal of cancer cell lines by standard endpoint assay formats (see below for the detailed description), or by real time electronic cell sensing (RT-CES) system, which provides dynamic cell response information after exposing to an anticancer agent. Several endpoint cell-based screening assay formats for anticancer agent discovery and validation may be used. For example, National Cancer Institute (NCI) provides an endpoint cytotoxicity assay system using a panel of 60 cancer cell lines, which can be used for a large scale of cell-based screening of anticancer agents. (See, e.g., Monks, A., et al. *J Natl. Cancer Inst.* 1991, 83, 757-766; Alley, M. C., et al. *Cancer Res.* 1988, 48, 589-601; Shoemaker, R. H., et al. *Proc. Clin. Biol. Res.* 1988, 276, 265-286; and Stinson, et al. *Proc. Am. Asso. Cancer Res.* 1989, 30, 613).

In this screening method, cell suspension that is diluted to a desired cell concentration is added into wells of a 96-well microtiter plate so that each well is having solution about 100 microliters with cell number between thousands (for example, 5000) and tens of thousands (for example, 40,000). The number of cells added to individual wells depends on cell type, cell size, cell growth characteristics. Cells in the plate are incubated at 37° C., saturated humidity and 5% $CO_2$ atmosphere in a standard cell culture incubator for about 24 hrs. Compounds of interest are prepared into test solutions with serial diluted concentrations. In one example, the dilution factor in the serial diluted solutions is 10-fold (or 2-, 3-, 4-fold) and five (or six to ten) different concentrations with a ratio of highest concentration to lowest concentration of 10,000. Other dilution factors and other various concentrations may also be used. Typically, the highest concentration of the test compound is $10^{-4}$ M. About 100 microliters of test solutions are added into each well at 24 hours after initial cell seeding into wells. Test solutions of each compound concentration are added into at least two wells for replicating purpose. The test compound may be dissolved in an organic solvent such as DMSO, and the 100 microliter test solutions may be a mixture of aqueous solution with the organic solvent-based solution or suspension.

After compound addition, cells are then incubated with the compound for additional 48 hours at 37° C. in 5% $CO_2$ atmosphere and saturated humidity. The cells can then be assayed for their viable cell numbers by various assays, for example, the sulforhodamine B assay (as described by Rubinstein, L. V., et al. *J. Natl. Cancer Inst.* 1990, 82, 1113-1118; and Skehan, P., et al. *J. Natl. Cancer Inst.* 1990, 82, 1107-1112). A plate reader is then used to read the optical densities and an $IC_{50}$ value, the concentration of drug that causes 50% growth inhibition, (or $GI_{50}$ value to emphasize the correction for the cells counted at time zero), is derived based on the dose response curves. Thus, $GI_{50}$ values are used to measure the growth inhibitory power of the test compound. See Boyd, et al in *Cytotoxic Anticancer Drugs: Models and Concepts for Drug Discovery and Development*; Vleriote, F. A., Corbett T. H., Baker L. H. (Eds.); Kluwer Academic: Hingham, Mass., 1992, pp 11-34.

In another assay format, a test compound is assayed for its cytotoxicity and/or cytostatic effect on certain cancer cell types, using endpoint assay methods. Cells in the NCI cancer cell panel may be used. Cells after a pre-incubation for certain length of time (for example, 8 hrs or 24 hrs) are incubated with a test compound at serially-diluted concentrations (for example, five 10-fold dilutions) for 24 hrs and/or 48 hrs, and/or other specific length of time. The dose dependent cytotoxicity and/or cytostatic effects of test compounds can then be tested and evaluated using the 3-(4,5-dimethylthiazol-2-yl)-2,5-diphenyltetrazolium bromide (MTT) assay method, as described by, for example, Boyd (In *Principle of Practice of Oncology*, Devita, J. T., Hellman, S. and Rosenberg S. A. (Eds), 1989, Vol, 3, PPO Update, No. 10).

Another in vitro assay may be used to evaluate the effect of compounds in arresting the cell cycle progression. More specifically, a test compound is added to cells of certain cell lines in a concentration-dependent manner. After cells are incubated for certain specific length of time, cells are stained using propidium iodide and are used for flow cytometric assessment. The cell populations of sub-G0/G1, G0/G1, S and G2/M phases are determined. All above in vitro assays are cell-based, single-time point (or multiple-time points using multiple plates) end-point assays.

Test compounds may also be screened using a novel in vitro cell-based screening assay system based on the electronic measurement of cell-substrate or cell-electrode impedances. In contrast to all the endpoint assay systems, the cell-based screening assay system allows for real time monitoring dynamic response of cancer cells to anticancer agents without labeling cells. This system can also be used for a large scale of in vitro cell-based high throughput screening of anticancer agents. The approach features in the integration of molecular and cell biology with microelectronics and is based on the electronic detection of biological assay process.

The details of this cell electronic sensing technology, called real-time cell electronic sensing (RT-CES™) and associated devices, systems and methods of use are described in U.S. provisional application No. 60/397,749, filed on Jul. 20, 2002; U.S. provisional application No. 60/435,400, filed on Dec. 20, 2002; U.S. Provisional application 60/469,572, filed on May 9, 2003, PCT application number PCT/US03/22557, filed on Jul. 18, 2003; PCT application number PCT/US03/22537, filed on Jul. 18, 2003; PCT application number PCT/US04/37696, filed on Nov. 12, 2004; PCT application number PCT/US05/04481, filed on Feb. 9, 2005; U.S. patent application Ser. No. 10/705,447, filed on Nov. 10, 2003; U.S. patent application Ser. No. 10/705,615, filed on Nov. 10, 2003; U.S. patent application Ser. No. 10/987,732, filed on Nov. 12, 2004; U.S. patent application Ser. No. 11/055,639, filed on Feb. 9, 2005, each of which is incorporated by reference. Additional details of RT-CES technology is further disclosed in U.S. provisional application No. 60/519,567, filed on Nov. 12, 2003, and U.S. provisional application No. 60/542,927, filed on Feb. 9, 2004, U.S. provisional application No. 60/548,713, filed on Feb. 27, 2004, U.S. provisional application No. 60/598,608, filed on Aug. 4, 2004; U.S. provisional application No. 60/598,609, filed on Aug. 4, 2004; U.S. provisional application No. 60/613,749, filed on Sep. 27, 2004; U.S. provisional application No. 60/613,872, filed on Sep. 27, 2004; U.S. provisional application No. 60/614,601, filed on Sep. 29, 2004; U.S. provisional application No. 60/630,071, filed on Nov. 22, 2004; U.S. provisional application No. 60/630,131, filed on Nov. 22, 2004, each of which is incorporated herein by reference.

For measurement of cell-substrate or cell-electrode impedance using RT-CES technology, microelectrodes having appropriate geometries are fabricated onto the bottom surfaces of microtiter plate or similar device, facing into the wells. Cells are introduced into the wells of the devices, and make contact to and attach to the electrode surfaces. The presence, absence or change of properties of cells affects the electronic and ionic passage on the electrode sensor surfaces. Measuring the impedance between or among electrodes provides important information about biological status of cells present on the sensors. When there are changes to the biological status of the cells analogue, electronic readout signals are measured automatically and in real time, and are converted to digital signals for processing and analysis. In a RT-CES system, a cell index is automatically derived and provided based on measured electrode impedance values. The cell index obtained for a given well reflects: 1) how many cells are attached to the electrode surfaces in this well; 2) how well cells are attached to the electrode surfaces in this well. Thus, the more the cells of same type in similar physiological conditions attach the electrode surfaces, the larger the cell index. And, the better the cells attach to the electrode surfaces (e.g., the cells spread-out more to have larger contact areas, or the cells attach tighter to electrode surfaces), the larger the cell index.

Through the use of the RT-CES system, dibenzyl trisulfide has been shown to inhibit proliferation of a variety of cancer types. Dibenzyl trisulfide has not previously been found using standard endpoint assays. Negative conclusions that dibenzyl trisulfide has no antiproliferation activity were made by the previous researchers ("*Discovery of novel inducers of cellular differentiation using HL*-60 *promyelocytic cells*", Mata-Greenwood, E., Ito, A., Westernburg, H., Cui, B., Mehta, R. G., Kinghorn, A. D. and Pezzuto, J. M. *Anticancer Res.* 2001, 21, 1763-1770).

To evaluate the anticancer efficacy and to predict possible mechanisms of the anticancer action of the dibenzyl trisulfide, ten anticancer compounds were tested with known mechanisms of action side by side with dibenzyl trisulfide utilizing a panel of 12 cancer cell lines. The time-dependent, cell responsive patterns of dibenzyl trisulfide (at certain concentrations) were somewhat similar to those of paclitaxel, vinblastine and colceimid (at certain concentrations). Thus, dibenzyl trisulfide may have mechanisms of anticancer action similar to those of paclitaxel, vinblastine, and colceimid. Dibenzyl trisulfide may act on cancer cells through other mechanisms of action, different from those of paclitaxel, vinblastine and colceimid. It is also possible that dibenzyl trisulfide act on cancer cells through multiple mechanisms of action, including the mechanism of action similar to those of pacliotaxel, vinblastine and colceimid.

In addition to the in vitro cell models and assay formats, anti-tumor activity of compounds can be further assessed and evaluated by in vivo animal models with transplanted cancer. Most in vivo models are mouse models.

In Vitro Cell-Based Screening Using Real-Time Cell Electronic Sensing (RT-CES) System The RT-CES system comprises three components, an electronic sensor analyzer, a device station and 16× or 96× microtiter plate devices. Microelectrode sensor array was fabricated on glass slides with lithographical microfabrication methods and the electrode-containing slides are assembled to plastic trays to form electrode-containing wells. Each 16× (or 96×) microtiter plate device used in RT-CES system comprises up to 16 (or 96) such electrode-containing wells. The device station receives the 16× or 96× microtiter plate devices and is capable of electronically switching any one of the wells to the sensor analyzer for impedance measurement. In operation, the devices with cells cultured in the wells are placed into a device station that is located inside an incubator. Electrical cables connect the device station to the sensor analyzer. Under the RT-CES software control, the sensor analyzer can automatically select wells to be measured and continuously conduct impedance measurements. The impedance data from the analyzer is transferred to a computer, analyzed and processed by the integrated software.

Impedance measured between electrodes in an individual well depends on electrode geometry, ionic concentration in the well and whether there are cells attached to the electrodes. In the absence of the cells, electrode impedance is mainly determined by the ion environment both at the electrode/solution interface and in the bulk solution. In the presence of the cells, cells attached to the electrode sensor surfaces will alter the local ionic environment at the electrode/solution interface, leading to an increase in the impedance. The more cells there are on the electrodes, the larger the increase in cell-electrode impedance. Furthermore, the impedance change also depends on cell morphology and the extent to which cells attach to the electrodes.

To quantify cell status based on the measured cell-electrode impedance, a parameter termed Cell Index is derived, according to $$CI = \max_{i=1,\ldots,N}\left(\frac{R_{cell}(f_i)}{R_b(f_i)} - 1\right)$$

where $R_b(f)$ and $R_{cell}(f)$ are the frequency dependent electrode resistances (a component of impedance) without cells or with cell present, respectively. N is the number of the frequency points at which the impedance is measured. Thus, Cell Index is a quantitative measure of the status of the cells in an electrode-containing well. Under the same physiological conditions, more cells attached on to the electrodes leads to larger $R_{cell}(f)$ value, leading to a larger value for Cell Index. Furthermore, for the same number of cells present in the well, a change in the cell status such as morphology will lead to a change in the Cell Index. For example, an increase in cell adhesion or cell spreading leads to larger cell-electrode contact area which will lead to an increase in $R_{cell}(f)$ and thus a larger value for Cell Index. The Cell Index may also be calculated using a formula different from the one described here. Other methods for calculating the Cell Index based on impedance measurement can be found in PCT application number PCT/US04/37696, fined on Nov. 12, 2004, PCT application number PCT/US05/04481, filed on Feb. 9, 2005, U.S. patent application Ser. No. 10/987,732, filed on Nov. 12, 2004, and U.S. patent application Ser. No. 11/055,639, filed on Feb. 9, 2005.

Different types of human cancer cells, including NCI-H460 (non-small cell lung cancer cells), MV522 SW (non-small cell lung cancer cells), MCF7 (breast cancer cells), A549 (non-small cell lung cancer cells), PC3 (prostate cancer cells), A431 (epidermoid cancer cells), HT1080 (fibrosarcoma cells), MDA.MB2321 (breast cancer cells), HT29 (colon cancer cells), HCC2998 (colon cancer cells), OVCAR4 (ovarian cancer cells), A2780 (ovarian cancer cells) and HepG2 (human hepatosarcoma) with different numbers (4000 to 20,000 per well) were seeded into 16× or 96× microtiter device and monitored by RT-CES™ system. The cells were allowed to grow for about 24 hours prior to the addition of dibenzyl trisulfide dissolved in DMSO solution (final DMSO concentration: 0.2%; final dibenzyl trisulfide concentration: between 1.5625 µM and 100 µM). The cell-electrode impedance was continuously measured and the corresponding, time dependent cell-index values were derived and recorded.

FIGS. 1-5, 6A, and 7-12 show the time-dependent cell index for a number of cell lines prior to and after addition of dibenzyl trisulfide at various concentrations. As shown in the Figures, dibenzyl trisulfide exhibited inhibitory effect on the proliferation of a number of cancer cell lines. The susceptibility to dibenzyl trisulfide differs among the cancer cell types. For some cancer cell types, a low dosage of dibenzyl trisulfide is sufficient to significantly inhibit cancer cell proliferation, whilst for other cancer cell types, a higher dosage is needed to achieve similar inhibition degree.

Figure 1B:
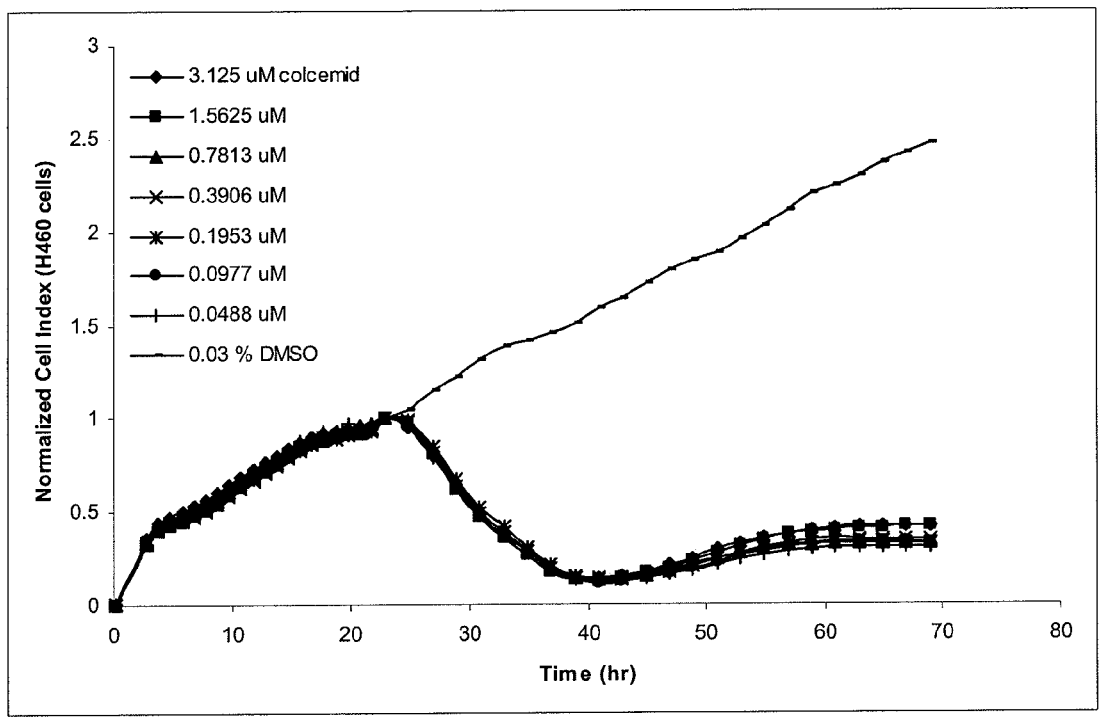
Figure 1C:
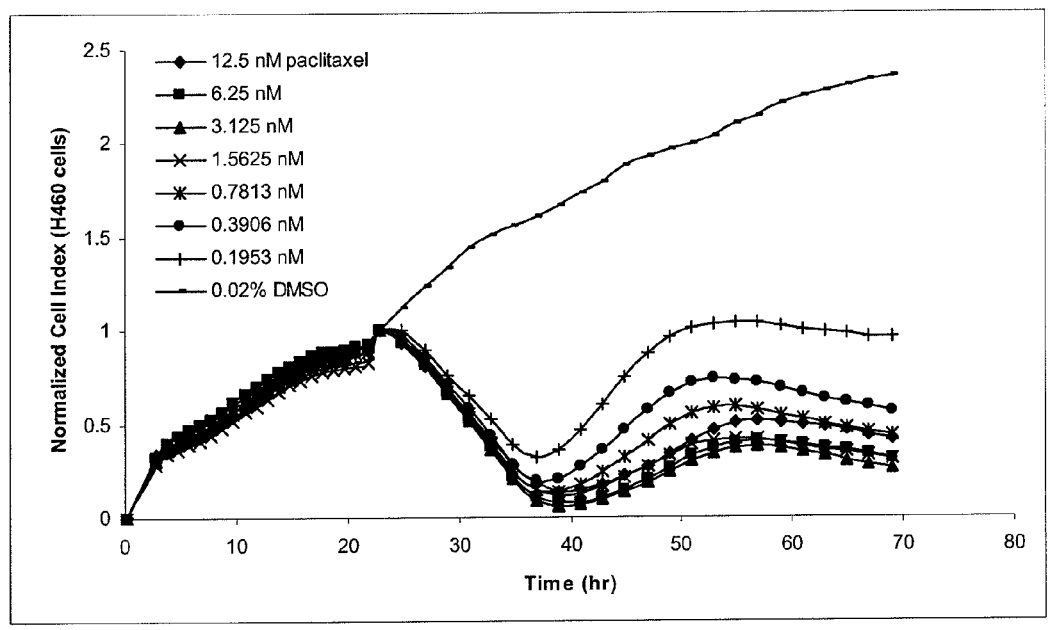

In one example, FIGS. 1B and 1C show the time-dependent cell index for H460 (non-small cell lung cancer cell line) cells prior to and after addition of colcemid and paclitaxel at various concentrations. As shown in FIGS. 1B and 1C, colcemid and paclitaxel exhibited inhibitory ability against the proliferation of A431 cells at concentrations studied. Furthermore, these figures indicate that after compound addition (colcemid or paclitaxel), the cell indices for H460 cells first decreased with time and then increased, showing that H460 cells had complex kinetic responses to either colcemid and paclitaxel. It is noteworthy that cell index curves shown in FIG. 1A for H460 cells under the influence of dibenzyl trisulfide (DBTS) at concentration of 25 µM and above are somewhat similar to the curves in FIGS. 1B and 1C, i.e., after addition of DBTS (25 µM and above), the cell indices for H460 cells also first decreased with time and then increased.

Figure 5:
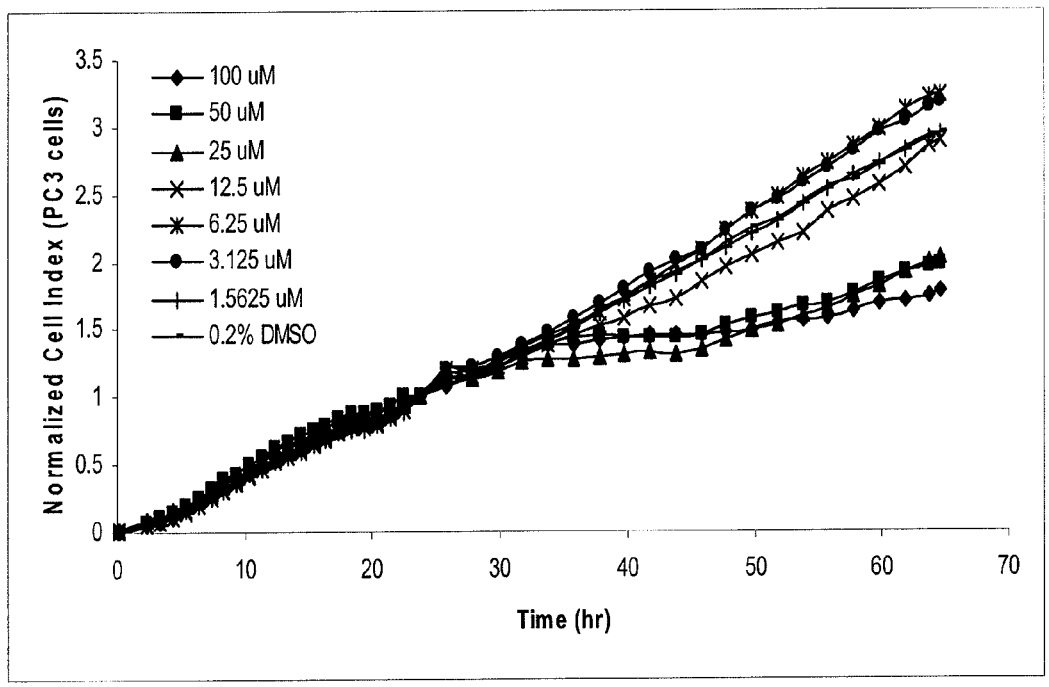
FIG. 5 shows responses of PC3 cells (prostate cancer cell line) to different concentrations of dibenzyl trisulfide (DBTS) (FIG. 6A) and 5-fluorouracil (FIG. 6B), as determined on RT-CES system.
Figure 6A:
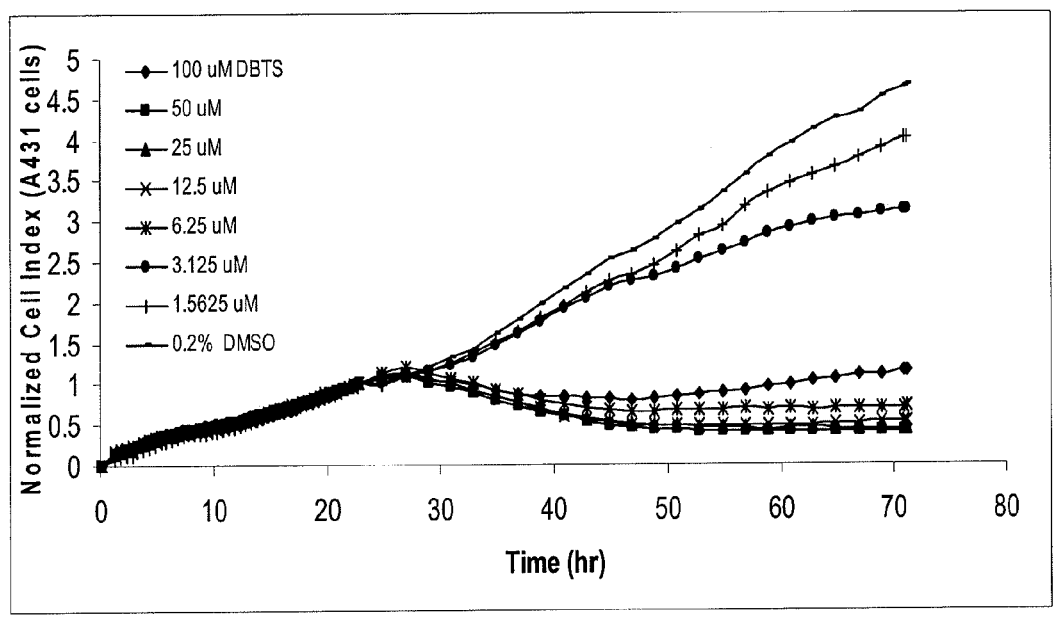
FIGS. 6A and 6B shows responses of A431 cells (epidermoid cancer cell line) to different concentrations of dibenzyl trisulfide (DBTS), as determined on RT-CES system.
Figure 6B:
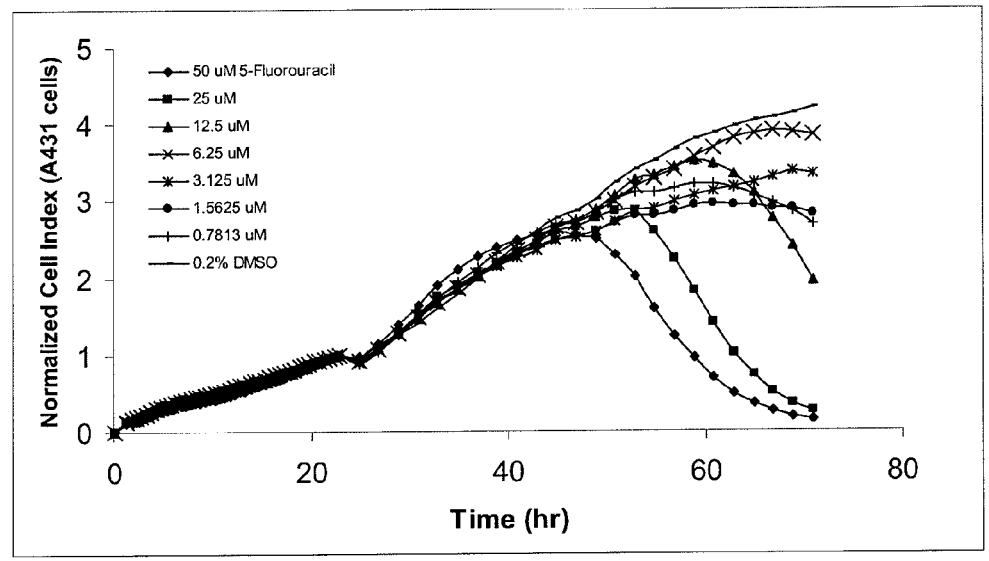

In another example, FIG. 6B shows the time-dependent cell index for A431 (epidermoid cancer cell line) cells prior to and after addition of 5-fluorouracil at various concentrations. As shown in FIG. 6B, 5-fluorouracil exhibited inhibitory ability against the proliferation of A431 cells at concentrations of 12.5 µM and above. The time dependent cell index curves in FIG. 6B are significantly different from those in FIG. 6A.

Figure 13:
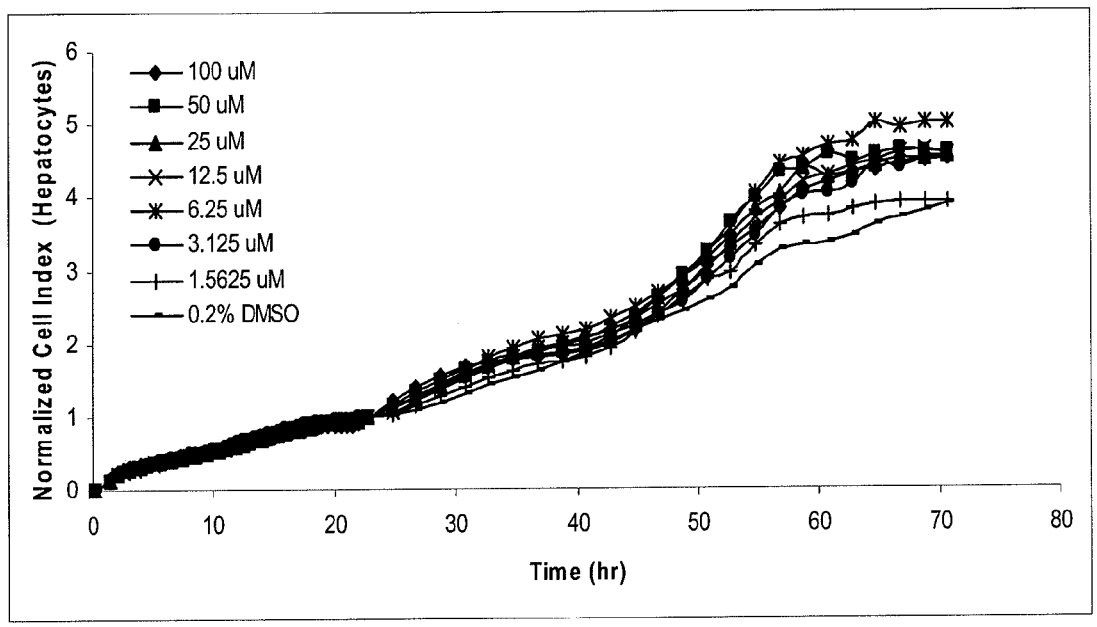
FIG. 13 shows responses of HepG2 cells (human hepatoma cell line) to different concentrations of dibenzyl trisulfide (DBTS), as determined on RT-CES system.

In another example, FIG. 13 shows the cell index data of HepaG-2 cell lines under the influence of dibenzyl trisulfide. As shown in FIG. 13, dibenzyl trisulfide did not demonstrate anti-proliferation ability on HepaG-2 cells.

In Vivo Screening for Anticancer Activity

To evaluate the in vivo anticancer efficacy of the test compounds including DBTS and ACEA100108 (a derivative of DBTS, see Table 33), various mouse models were used, including the mouse sarcoma S180 model, the mouse Lewis lung cancer model, P388 lymphocytic leukemia model, and three human tumor xenograft models in immunodeficient nude mice: Bcap-37 human breast cancer, HCT-8 human colon cancer, ao12/17 human ovarian cancer. Details of the in vivo anticancer efficacy of the test compounds are provided below.

Assessment of Acute Toxicity of DBTS and Compound ACEA100108

To evaluate the in vivo acute, intravenous toxicity of DBTS and ACEA100108 (a derivative of DBTS, see Table 33), the experiments were performed in non-tumor bearing, normal Kunming mice by monitoring the acute response of mice to a single dose of DBTS or ACEA100108 via intravenous injection (i.v.). The number of death for the treated mice was monitored and recorded. $LD_{50}$ values for these compounds were calculated. Details of the study are provided below.

The following examples are offered to illustrate but not to limit the invention.

EXAMPLE 1

Anticancer Activity of DBTS Against Mouse Sarcoma S180 and Mouse Lewis Lung Cancer To evaluate the in vivo anticancer efficacy of the test compounds, two mouse transplanted tumor models were used for the in vivo evaluation: the mouse sarcoma S180 model and the mouse Lewis lung cancer model. Experimental mice were maintained in the Pharmacology Lab of Shanghai Pharmaceutical Industry Institute. The mouse source and specifications are as follows. The mice were C57BL/6 and Kunming strains, provided by Academic Sinica, Experimental Animal Center, and certification number: Academic Sinica Experimental Animal Certificate, No. 5. The mouse weight is between 18-20 g. Both male and female mice were used. However, for each experiment, animals of same sex were used. The number of animals tested were as follows: 30 mice for the test compound group, including 10 for the high dose group, 10 for the middle dose group and 10 for the low dose group; 10 mice were for the positive compound group; 20 mice for the negative control group, including 10 mice for the Normal Saline group and 10 mice for the solvent only group. The high, middle and low doses of DBTS are, 50, 25 and 12.5 mg/kg/d, respectively.

Test controls. For the negative control, two groups were set up: the solvent only control group and normal saline control group. In the solvent only control group, each mouse was administered intravenously with the solvent only having the same volume and same concentration (10% for the sarcoma S180 model and 5% for the Lewis lung cancer model) as those used for high dose DBTS test, once a day, and for 7 or 10 consecutive days. In the normal saline group, each mouse was administered with 0.5 ml of normal saline, once per day and for 7 or 10 consecutive days. For the positive control group, the anticancer compound, cyclophosphamide (CTX) was administered intraperitoneally at 30 mg/kg, once per day and for 7 or 10 consecutive days.

Preparation and Administration of Test Compounds. Test compound solutions for evaluating anti-tumor efficiency cancer models were prepared as follows. In the mouse sarcoma S180 mouse model, 200 mg of DBTS was dissolved in 10 mL of castor oil (in polyoxyethlated version) first, and then mixed with 90 mL of normal saline. The final DBTS concentration in the solution is 0.2%, and the final solvent concentration is 10%. Each mouse was administered intravenously with the compound solution of 0.5 mL (high dose), 0.3 mL (middle dose) and 0.15 mL (low dose), respectively.

In the mouse Lewis lung cancer model, 200 mg of DBTS was dissolved in 5 mL castor oil (in polyoxyethlated version). Each time before use, this solution was diluted with normal saline to achieve final DBTS concentration of 0.2% (high dose), 0.1% (middle dose) and 0.05% (low dose) respectively. In this case, each mouse (about 20 g in weight) was administered intravenously with 0.5 mL of the compound solution of a given compound concentration. The intravenous injection speed was about 0.5 mL/0.5 min.

The dosages and administration of test compounds are within the knowledge of those commonly skilled in pharmacology. For example, the test compounds may be administered by intravenous injection with a test compound solution twice per day and for 7 consecutive days. Alternatively, the test compounds may be administered by intravenous injection with a test compound solution once per day and for 10 consecutive days.

Preparation of Tumor Cells for Transplantation and Determination of Compound Efficacy. To prepare the tumor cells, the fast grown tumors were first removed from the transplanted tumor mice (the sarcoma S180 model or the Lewis lung cancer model), the tumor tissues were dissected, and the tumor cell suspensions were prepared from the dissected tissues at the concentration of $2-4 \times 10^7$ tumor cells/ml. 0.2 mL of the tumor cell suspension (between 4 and 8 million tumor cells) was then transplanted back into an experimental mouse by subcutaneous injection. Twenty four hours after the transplantation, mice were administered intravenously with a given dose of DBTS, with normal saline, or solvent only which served as the negative control, or with 50 mg/kg CTX intraperitoneally which served as the positive control. Two weeks after the transplantation, mice were sacrificed and the transplanted tumors were removed from the experimental mice. Each removed solid tumor was weighted, and the tumor inhibition rate in the DBTS-treated groups and in the CTX-treated group was calculated according to the formula:

Tumor inhibition rate %=(average weight of tumor in the negative control group−average weight of tumor in the compound treated group)/average weight of tumor in the negative control group× 100 (2)

For the mouse sarcoma S180 model, the S180 cells were subcutaneously transplanted at approximately 5 million cells per mouse. After 24 hours of the transplantation, each mouse in the test group was administered intravenously with dibenzyl trisulfide at 50, 25, or 12.5 mg/kg respectively per day and for 7 or 10 consecutive days. For the positive control group, each mouse was administered with cyclophosphamide (Cytoxan, CTX) at 50 mg/kg intraperitoneally per day and for 7 consecutive days. For the negative control group, each mouse was administered intravenously either with normal saline, or with the solvent for dibenzyl trisulfide at the same concentration as that in the test group per day and for consecutive 7 days. For each group, 10 mice were used.

For the mouse Lewis lung cancer model, the Lewis lung cancer cells were subcutaneously transplanted at approximately 5 million cells per mouse. After 24 hours of the transplantation, each mouse in the test group was administered intravenously with dibenzyl trisulfide at 50, 25, or 12.5 mg/kg per day and for 10 consecutive days. For the positive control group, each mouse was administered with CTX at 50 mg/kg intraperitoneally per day and for 10 consecutive days. For the negative control group, each mouse was administered intravenously either with normal saline, or with the solvent for dibenzyl trisulfide at the same concentration as that in the test group per day and for consecutive 10 days. For each group, 10 mice were used.

Figure 14:
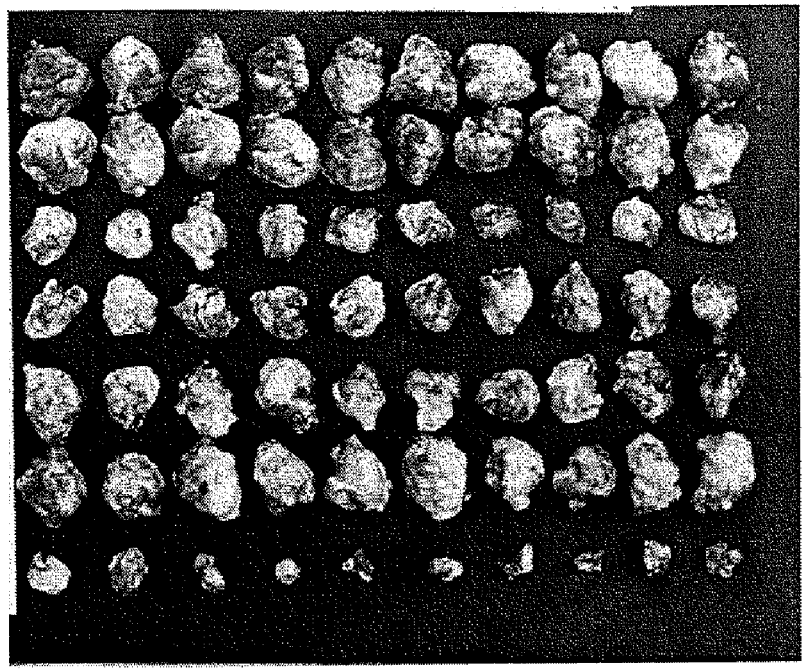
FIG. 14 shows mouse sarcoma S180 tumors (planted into mice by subcutaneous implanting) treated with dibenzyl trisulfide (DBTS).

Results. In the mouse sarcoma S180 model, DBTS showed an average tumor inhibition rate of 63.30%, 54.68% and 48.69% for the 50, 25 and 12.5 mg/kg dosage groups respectively (relative to the normal saline control). The detailed results are shown in Table 9 and FIG. 14, describing an in vivo efficacy study of 0.2% DBTS in the mouse sarcoma S180 model. In FIG. 14, the seven rows (1-7, respectively) represent results from the following administered compounds (iv× 7qd): 1) negative control; 2) normal saline; 3) DBTS (25 ml/kg); 4) DBTS (15 ml/kg); 5) DBTS (7.5 ml/kg); 6) solvent control (15 ml/kg) and 7) positive control CTX (30 mg/kg).

It was observed that right after the intravenous injection of DBTS, mice exhibited transient abnormal reactions including jumping, fast breathing, and lying down followed by reduced activities. Such reactions typically lasted 10-15 minutes. The same abnormal reactions were also seen in the mice intravenously injected with only solvent. Therefore, the injection speed and the high concentration of the solvent other than DBTS may result in the transient abnormal reactions in the mice.

Figure 15:
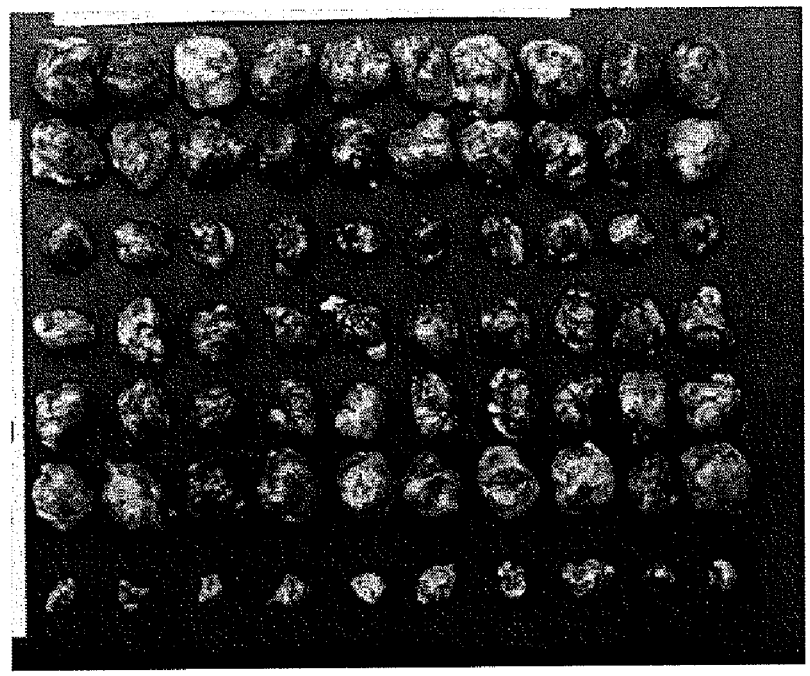
FIG. 15 shows mouse Lewis lung cancer (planted into mice by subcutaneous implanting) treated with dibenzyl trisulfide (DBTS).

In the Lewis lung cancer model, DBTS showed an average tumor inhibition rate of 67.05%, 51.34% and 45.21% for the 50, 25 and 12.5 mg/kg dosage groups respectively (relative to the normal saline control). The detailed results are summarized in Table 10 and FIG. 15, describing an efficacy study of 0.2% DBTS on mouse Lewis lung cancer. In FIG. 15, the seven rows (1-7, respectively) represent results from the following administered compounds: 1) negative control; 2) normal saline; 3) DBTS (25 ml/kg); 4) DBTS (15 ml/kg); 5) DBTS (7.5 ml/kg); 6) solvent control (15 ml/kg) and 7) positive control CTX (30 mg/kg). DBTS and the solvent control were administered iv×10 qd; the positive control was administered ip×7qd. In contrast to the mice used for the mouse sarcoma S180 experiment, the mice intravenously injected with either DBTS or solvent in this experiment showed much minor transient abnormal reactions.

By using the solvent only as the negative control, the average in vivo tumor inhibition rates of DTBS for the S180 sarcoma are 50.25%, 38.58% and 30.46% in 50, 25 and 12.5 mg/kg dosage groups respectively, as shown in Table 11. For the Lewis lung cancer model, the average in vivo tumor inhibition rates of DBTS are 62.28%, 44.30% and 37.38% in the 50, 25 and 12.5 mg/kg dosage groups respectively, as shown in Table 12.

The results generated from two mouse transplanted tumor models demonstrate the specific inhibition of transplanted tumor growth in the mice administered intravenously with DBTS. When intravenously administered with a high dose of DBTS (50 mg/kg/d, and for 7 or 10 consecutive days), a tumor inhibition rate of 65% was achieved in either mouse transplanted tumor model, by using the normal saline as the negative control. The solvent used to prepare DBTS solution showed a weak inhibitory effect on the tumor growth in the mouse transplanted tumor models, and may also cause transient abnormal reactions in mice after intravenous injection.

TABLE 9

In vivo antitumor efficacy of DBTS in the mouse sarcoma S180 model
(subcutaneously transplanted sarcoma)

| Sample | Dosage (mg/kg/d) | Administration method | Animal number (beginning/end) | Animal weight (g) beginning/end | Tumor weight (g) X +/− SD | Inhibition rate (%) |
|---|---|---|---|---|---|---|
| DBTS | 50 | iv X 7 qd | 10/10 | 19.5/22.9 | 0.98 ± 0.20† | 63.30 |
| DBTS | 25 | iv X 7 qd | 10/10 | 19.4/23.8 | 1.21 ± 0.14† | 54.68 |
| DBTS | 12.5 | iv X 7 qd | 10/10 | 19.4/24.5 | 1.37 ± 0.12† | 48.69 |
| Positive control (CTX) | 30 | ip X 7 qd | 10/10 | 19.6/20.3 | 0.22 ± 0.11† | 91.76 |
| Negative control | Normal saline | iv X 7 qd | 10/10 | 19.3/24.8 | 2.67 ± 0.15 | |

†p < 0.01, as compared with the negative control.

TABLE 10

The in vivo antitumor efficacy of DBTS in the mouse Lewis cancer model
(subcutaneously transplanted tumor)

| Sample | Dosage (mg/kg/d) | Administration method | Animal number (beginning/end) | Animal weight (g) beginning/end | Tumor weight (g) X +/− SD | Inhibition rate (%) |
|---|---|---|---|---|---|---|
| DBTS | 50 | iv X 10 qd | 10/10 | 18.9/22.9 | 0.86 ± 0.14† | 67.05 |
| DBTS | 25 | iv X 10 qd | 10/10 | 19.3/23.5 | 1.27 ± 0.22† | 51.34 |
| DBTS | 12.5 | iv X 10 qd | 10/10 | 19.0/23.9 | 1.43 ± 0.18† | 45.21 |
| Positive control (CTX) | 30 | ip X 10 qd | 10/10 | 19.1/20.2 | 0.323 ± 0.14† | 87.62 |
| Negative control | Normal saline | iv X 10 qd | 20/20 | 19.2/24.9 | 2.61 ± 0.25 | |

†p < 0.01, as compared with the negative control.

TABLE 11

The in vivo antitumor efficacy of DBTS in the mouse sarcoma S180 model
(subcutaneously transplanted tumor)

| Sample | Dosage (mg/kg/d) | Administration method | Animal number (beginning/end) | Animal weight (g) beginning/end | Tumor weight (g) X +/− SD | Inhibition rate (%) |
|---|---|---|---|---|---|---|
| DBTS | 50 | iv X 7 qd | 10/10 | 19.5/22.9 | 0.98 ± 0.20† | 50.25 |
| DBTS | 25 | iv X 7 qd | 10/10 | 19.4/23.8 | 1.21 ± 0.14† | 38.58 |
| DBTS | 12.5 | iv X 7 qd | 10/10 | 19.4/24.5 | 1.37 ± 0.12† | 30.46 |
| Positive control (CTX) | 30 | ip X 7 qd | 10/10 | 19.6/20.3 | 0.22 ± 0.11† | 88.83 |
| Negative control | 10% solvent | iv X 7 qd | 10/10 | 19.3/24.7 | 1.97 ± 0.18 | |

†p < 0.01, as compared with the solvent (10%) only negative control.

TABLE 12

The in vivo antitumor efficacy of DBTS in the mouse Lewis cancer model
(subcutaneously transplanted tumor)

| Sample | Dosage (mg/kg/d) | Administration method | Animal number (beginning/end) | Animal weight (g) beginning/end | Tumor weight (g) X +/− SD | Inhibition rate (%) |
|---|---|---|---|---|---|---|
| DBTS | 50 | iv X 10 qd | 10/10 | 18.9/22.9 | 0.86 ± 0.14† | 62.28 |
| DBTS | 25 | iv X 10 qd | 10/10 | 19.3/23.5 | 1.27 ± 0.22† | 44.30 |
| DBTS | 12.5 | iv X 10 qd | 10/10 | 19.0/23.9 | 1.43 ± 0.18† | 37.28 |

TABLE 12-continued

The in vivo antitumor efficacy of DBTS in the mouse Lewis cancer model (subcutaneously transplanted tumor)

| Sample | Dosage (mg/kg/d) | Administration method | Animal number (beginning/end) | Animal weight (g) beginning/end | Tumor weight (g) X +/− SD | Inhibition rate (%) |
|---|---|---|---|---|---|---|
| Positive control (CTX) | 30 | ip X 7 qd | 10/10 | 19.1/20.2 | 0.323 ± 0.14† | 85.83 |
| Negative control | 5% solvents | iv X 7 qd | 20/20 | 19.1/24.3 | 2.28 ± 0.25 | |

†p < 0.01, as compared with 5% solvent only negative control.

EXAMPLE 2

Anticancer Activity of DBTS on Mouse Lewis Lung Cancer

This study evaluates the in vivo anticancer efficacy of dibenzyl trisulfide (DBTS) in the mouse Lewis lung cancer model as in Example 1. The experimental mice were maintained in the Pharmacology Lab of Shanghai Pharmaceutical Industry Institute. The mice for experiments were $C_{57}BL/6$ strain, provided by Academic Sinica, Experimental Animal Center, certification number: SCXK (Shanghai) 2003-0003. The mouse weight was between 18 and 20 g. Only female mice were used. The numbers of animals tested were as follows: 10 for each dose group, 10 for positive control group and 20 for negative control group (10 for physiological control group and 10 for solvent-control group).

Test control. For the negative control, two groups were set up: the solvent only control group and normal saline control group. In the solvent only control group, each mouse was administered intravenously with the solvent only having the same volume and same concentration (5% solvent in normal saline) as those used in a high dose DBTS test, once a day, for 7-10 consecutive days. In the normal saline group, each mouse was administered with 0.5 ml of normal saline, once a day, for 10 consecutive days. For positive control group, an anticancer compound, cyclophosphamide (Cytoxan, CTX, for intraperitoneal use) was administered intraperitoneally at 30 mg/kg, once a day for 7 consecutive days. In addition, as a reference group, an anticancer compound, Taxol, was administered intravenously at 15, 10 and 7.5 mg/kg, once a day for 5 consecutive days.

Preparation and Administration of Test Compounds. 400 mg of DBTS was dissolved in 10 mL of castor oil (solvent) to have a DBTS concentration 40 mg/ml in the solvent. Each time before use, this solution was diluted in normal saline to achieve desired DBTS concentrations. Normal saline was added to dilute DBTS solution to desired concentrations of 0.2% (high dose), 0.1% (middle dose) and 0.05% (low dose) respectively. Each mouse was administered intravenously with the compound solution of 0.5 mL at a controlled injection speed of 0.5 ml/0.5 min. 24 hrs after the tumor transplantation, intravenous injections of compound solutions into carrier mice were performed once a day, for consecutive 7 or 10 days.

Preparation of Tumor Cells for Transplantation and Determination of Compound Efficacy. To prepare the tumor cells, the fast growing tumors were first removed from the transplanted tumor mice, the tumor tissues were dissected and tumor cell suspensions were prepared in normal saline to have a concentration of $2-4 \times 10^7$ cells/ml. 0.2 ml of cell suspension was subcutaneously injected into the axillary region of each mouse. Twenty four hours after the transplantation, mice were administered with a given doses of DBTS, with normal saline, or solvent only which serves as the negative control, or with 30 mg/kg CTX intraperitoneally which served as the positive control. About two weeks after transplantation, mice were sacrificed and the transplanted tumors were removed from experimental mice. Each removed solid tumor was weighed; the tumor inhibition rate in each dosage group was calculated according to equation (2) in Example 1 (Anticancer Activity of DBTS Against Mouse Sarcoma S180 and Mouse Lewis Lung Cancer).

For the mouse Lewis lung cancer model, the Lewis lung cancer cells were subcutaneously transplanted at approximately 6 million cells per mouse. After 24 hours of the transplantation, each mouse in the test group was administered intravenously with dibenzyl trisulfide at 50, 25, or 12.5 mg/kg per day and for 10 consecutive days. For the positive control group, each mouse was administered with CTX at 30 mg/kg intraperitoneally per day and for 7 consecutive days. For the negative control group, each mouse was administered intravenously either with normal saline, or with the solvent for dibenzyl trisulfide at the same concentration as that in the test group per day and for consecutive 10 or 7 days. For each group, 10 mice were used. For Taxol reference group, each mouse in the test group was administered intravenously with Taxol at 15, 10 or 7.5 mg/kg per day and for 5 consecutive days.

Results. In the Lewis lung cancer model, DBTS showed an average tumor inhibition rate of 65.77%, 51.61% and 43.10% for the 50, 25 and 12.5 mg/kg dosage groups respectively (relative to the normal saline control). The detailed results are shown in Table 13. By using the solvent only as the negative control, the corresponding tumor inhibition rates are 61.02%, 46.94% and 35.10%, respectively (Table 14). It was observed that right after the intravenous injection of DBTS, mice exhibited transient abnormal reactions including jumping, fast breathing, and lying down followed by reduced activities. Such reactions typically lasted 10-15 minutes. The same abnormal reactions were also seen in the mice intravenously injected with only solvent.

In the reference test, Taxol showed an average tumor inhibition rate of 48.94%, 36.97 and 30.28% for the 15, 10 and 7.5 mg/kg dosage groups respectively (relative to the normal saline control). The detailed results are shown in Table 15.

The result generated in the mouse Lewis lung cancer model demonstrates the specific inhibition of transplanted tumor growth in the mice administered intravenously with DBTS. When intravenously administered with a high dose of DBTS (50 mg/kg/d, and for 10 consecutive days), a tumor inhibition rate of 65% was achieved in the mouse transplanted tumor model, by using the normal saline as the negative control. Such data have been shown to be reproducible. The solvent used to prepare DBTS solution showed a weak inhibitory effect on the tumor growth in the mouse transplanted tumor models, and may also cause transient abnormal reactions in mice after intravenous injection.

nude mice: Bcap-37 human breast cancer and HCT-8 human colon cancer. All the mouse models are maintained in the Pharmacology Lab of Shanghai Pharmaceutical Industry Institute. For human tumor xenograft models, cancer cells were passed twice in vivo before being transplanted into the nude mice for the study. Cultured human cancer cells in flask

TABLE 13

In vivo antitumor efficacy of DBTS in the mouse Lewis cancer model (subcutaneously transplanted tumor).

| Sample | Dosage (mg/kg/d) | Administration method | Animal No. beginning/end | Animal weight (g) beginning/end | Tumor weight (g) $\overline{X} \pm SD$ | Tumor Inhibition rate (%) |
|---|---|---|---|---|---|---|
| DBTS | 50 | ivx10 qd | 10/10 | 21.0/23.4 | 0.955 ± 0.20*** | 65.77 |
| DBTS | 25 | ivx10 qd | 10/10 | 21.2/23.7 | 1.35 ± 0.10*** | 51.61 |
| DBTS | 12.5 | ivx10 qd | 10/10 | 20.9/24.1 | 1.59 ± 0.16*** | 43.01 |
| Positive Control (CTX) | 30 | ipx7 qd | 10/10 | 21.1/22.3 | 0.258 ± 0.09*** | 90.75 |
| Negative Control | Normal saline | ivx10 qd | 20/20 | 21.3/26.0 | 2.79 ± 0.30 | |

***P < 0.01, as compared with the negative control.

TABLE 14

In vivo antitumor efficacy of DBTS in the mouse Lewis cancer model (subcutaneously transplanted tumor).

| Sample | Dosage (mg/kg/d) | Administration method | Animal Number Beginning/end | Animal weight (g) beginning/end | Tumor weight (g) $\overline{X} \pm SD$ | Tumor inhibition rate (%) |
|---|---|---|---|---|---|---|
| DBTS | 50 | ivx10 qd | 10/10 | 21.0/23.4 | 0.955 ± 0.20*** | 61.02 |
| DBTS | 25 | ivx10 qd | 10/10 | 21.2/23.7 | 1.35 ± 0.10*** | 46.94 |
| DBTS | 12.5 | ivx10 qd | 10/10 | 20.9/24.1 | 1.59 ± 0.16*** | 35.10 |
| Negative Control | 5% solvent | ivx7 qd | 10/10 | 21.3/26.0 | 2.79 ± 0.30 | |

***P < 0.01, as compared with the 5% solvent only negative control

TABLE 15

In vivo antitumor efficacy of Taxol in the mouse Lewis cancer model (subcutaneously transplanted tumor). Data is used as reference here.

| Sample | Dosage (mg/kg/d) | Administration method | Animal number beginning/end | Animal weight (g) beginning/end | Tumor weight (g) $\overline{X} \pm SD$ | Tumor Inhibition rate % |
|---|---|---|---|---|---|---|
| Taxol | 15 | ivx5 qd | 8/8 | 18.9/19.3 | 1.45 ± 0.14*** | 48.94 |
| Taxol | 10 | ivx5 qd | 8/8 | 18.7/21.7 | 1.79 ± 0.09*** | 36.97 |
| Taxol | 7.5 | ivx5 qd | 8/8 | 18.5/22.9 | 1.98 ± 0.14*** | 30.28 |
| Negative Control | Normal saline | ivx5 qd | 16/16 | 18.6/24.9 | 2.84 ± 0.31 | |

***P < 0.01, as compared with the negative control
Note:
Taxol is often used as positive control for anticancer efficacy test. The dosage is 10 mg/kg/d, ivx7 qd.

EXAMPLE 3

In Vivo Anticancer Activity of ACEA100108 on Lewis Lung Cancer and P388 Lymphocytic Leukemia in Mice, and on Bcap-37 Human Breast Cancer and HCT-8 Human Colon Cancer in Nude Mice To evaluate the in vivo anticancer efficacy of compound ACEA100108 (a DBTS derivative, see Table 33), mouse models with transplanted cancer were used, including Lewis lung cancer model and P388 lymphocytic leukemia model, and two human tumor xenograft models in immunodeficient were first xenograft-transplanted in immunodeficient nude mice. After the cancer cells grew to a tumor of certain sizes in the nude mice, the tumor was removed form the nude mice and tumor tissues were dissected. The cell suspensions were prepared from the dissected tumor tissue and transplanted back to immunodeficient nude mice again (i.e. the second passage of cancer cells in human cancer xenograft-transplanted model). After the cancer cells grew to certain size, the tumor was removed from nude mice and the tumor tissues were dissected. The cell suspensions were prepared from dissected tissues and were used for the study of human cancer xenograft models described here.

The mice for experiments were $C_{57}BL/6$, DBF1 and BALB/c nude mice strains, provided by Academic Sinica, Experimental Animal Center, certification number: SCXK (Shanghai) 2003-0003. The mouse weight was between 18 and 22 g. Both male and female mice were used. However, for each experiment, animals of same sex were used. For the mouse transplanted tumor model, the numbers of animals tested were as follows: 10 for each dose group, 10 for positive control group and 20 for negative control group. For human tumor xenograft model, the numbers of animals tested were as follows: 6 for each dose group, 6 for positive control group and 12 for negative control group.

Test control. For negative control, each mouse was administered intravenously with the solvent only having the same volume and same concentration as those used in high dose ACEA100108 test, once a day, for 7 consecutive days. For positive control group, an anticancer compound, Taxol was administered intravenously at 10 mg/kg, once a day for 7 consecutive days. In a reference group, DBTS was administered intravenously at 50 mg/kg, once a day for 7 consecutive days.

Preparation and Administration of Test Compounds. Compound ACEA100108 was dissolved in hydrogenated castor oil (solvent) to have a compound ACEA100108 concentration of 20 mg/ml in the solvent. Each time before use, this solution was diluted in normal saline to achieve desired ACEA100108 concentrations. Each mouse (about 20 g in weight) was administered intravenously with the compound solution of 0.5 mL at a controlled injection speed of 0.5 ml/0.5 min. 24 hrs after the tumor transplantation, intravenous injections of compound solutions into carrier mice were performed once a day, for consecutive 7 or 10 days. Different dosages of compound ACEA100108 between 100 and 6.25 mg/kg were used in the study.

Preparation of Tumor Cells for Transplantation and Determination of Compound Efficacy. To prepare the cancer cells for mouse Lewis lung cancer model, human breast cancer xenograft model and human colon cancer xenograft model, the fast growing tumors were first removed from the transplanted tumor mice. The tumor tissues were dissected and tumor cell suspensions were prepared in normal saline to have a concentration of $2\text{-}4\times10^7$ cells/ml. 0.2 ml of cell suspension was subcutaneously injected into the axillary region (right-side) of each mouse. Twenty four hours after the transplantation, mice were administered with a given dose of ACEA100108, or with solvent only which serves as the negative control, or with 10 mg/kg Taxol which served as positive control, or with 50 mg/kg DBTS which served as a reference test. Between two and four weeks after transplantation, mice were sacrificed and the transplanted tumors were removed from experimental mice. Each removed solid tumor was weighed; the tumor inhibition rate in each dosage group was calculated according to equation (2) in Example 1.

For human tumor xenograft model, all used materials, including animal food, animal cage, supporting materials and apparatus contacted by animals, were high-pressure sterilized. Nude mice were maintained in laminar flow shelves under SPF condition. After tumor transplantation, mouse weight and tumor size in each compound dosage group were dynamically monitored and plotted. The tumor size was determined by measuring the major axis (a) and minor axis (b) of the tumor, and tumor volume was calculated according to the formula $$\text{Tumor volume}=a\times b^2/2 \quad (3)$$

To prepare cancer cells for the P388 murine lymphocytic leukemia model, ascites of a P388 leukemia-bearing mouse were removed under sterile condition. The ascites were diluted in normal saline (1:6 for ascites to normal saline) to prepare cell suspension. 0.2 mL of the cell suspension was then injected intraperitoneally. Twenty four hours after transplanting the cancer cells into mice, mice were administered with given doses of a given dose of ACEA100108, or with solvent only which serves as the negative control, or with 10 mg/kg Taxol and with 2 mg/kg MMC (mitomycin C) which served as positive controls, or with 50 mg/kg DBTS which served as a reference test. The life span of carrier mice was determined within 30 days. The life span ratio comparing to the negative control group of the carrier mice in each compound treatment group was calculated according to the formula:

Life span ratio %=average life span for the compound treatment group/average life span for the negative control group×100% (4)

Results. In the Lewis lung cancer model, ACEA100108 showed the average of in vivo tumor inhibition rates of 60.15%, 55.35% and 34.32%, respectively, in 100 (administered only 5 times because of toxicity), 25 and 6.25 mg/kg dosage groups (relative to the solvent-only control). In the same experiment, DBTS showed the average in vivo tumor inhibition rates of 63.10% and 57.93%, respectively, in 100 (administered only 5 times because of toxicity) and 25 mg/kg dosage groups, and Taxol showed an in vivo tumor inhibition rate of 43.91% for the routine administration dosage of 10 mg/kg. The results are summarized in Table 16.

In murine lymphocytic leukemia model, the average increase in life span of mice treated with compound ACEA100108 were 106.18%, 107.22% and 109.28%, respectively, in 50, 25 and 12.5 mg/kg dosage groups. In the same experiment, the average increase in life span of mice was 109.28% for the mice being treated with DBTS compound at a dosage of 50 mg/kg, and the average increase in life span of mice treated with 10 mg/kg Taxol compound was 109.28%. The details are provided in Table 17.

Figure 16:
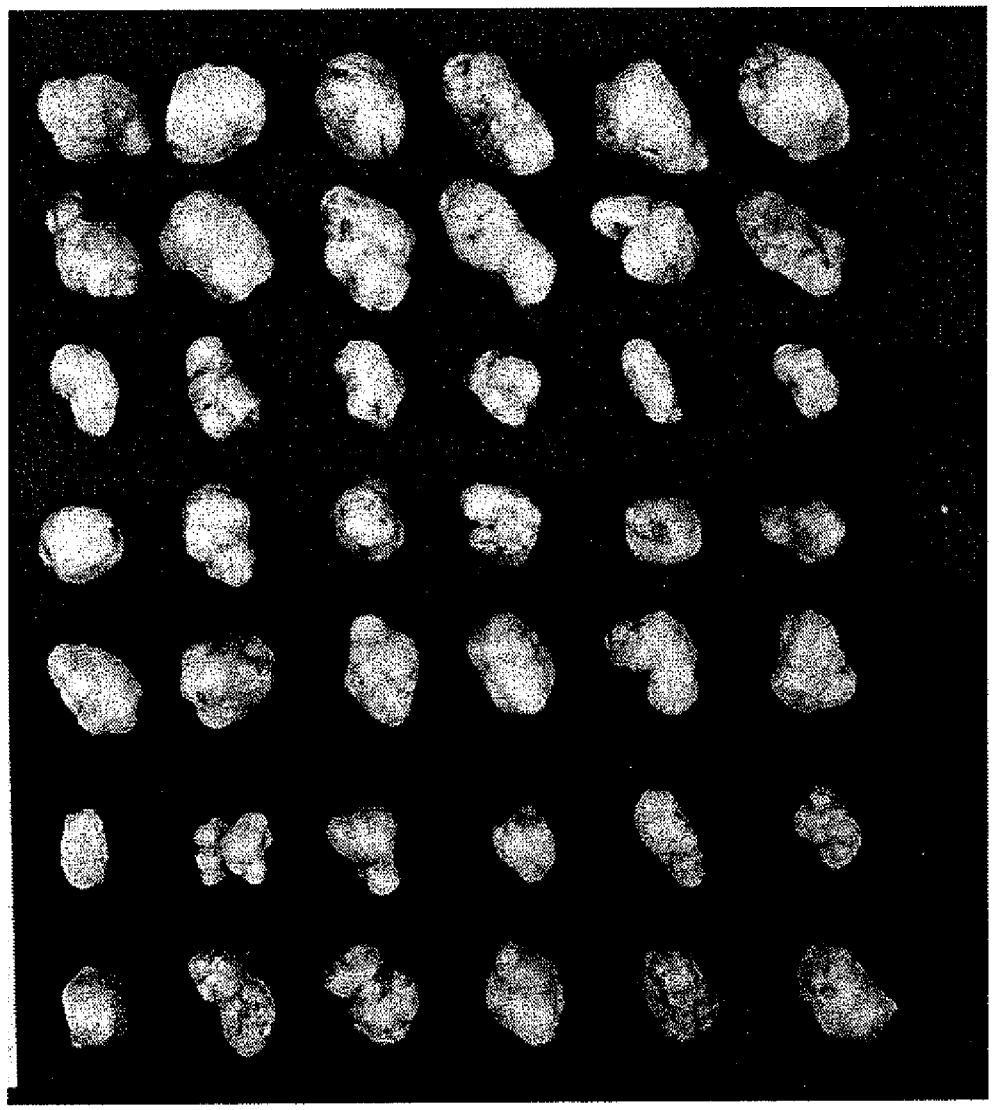
FIG. 16 shows Bcap-37 human breast tumors that were xenograft-transplanted in immunodeficient nude mice by subcutaneous seeding and were treated with compound ACEA100108.
Figure 17:
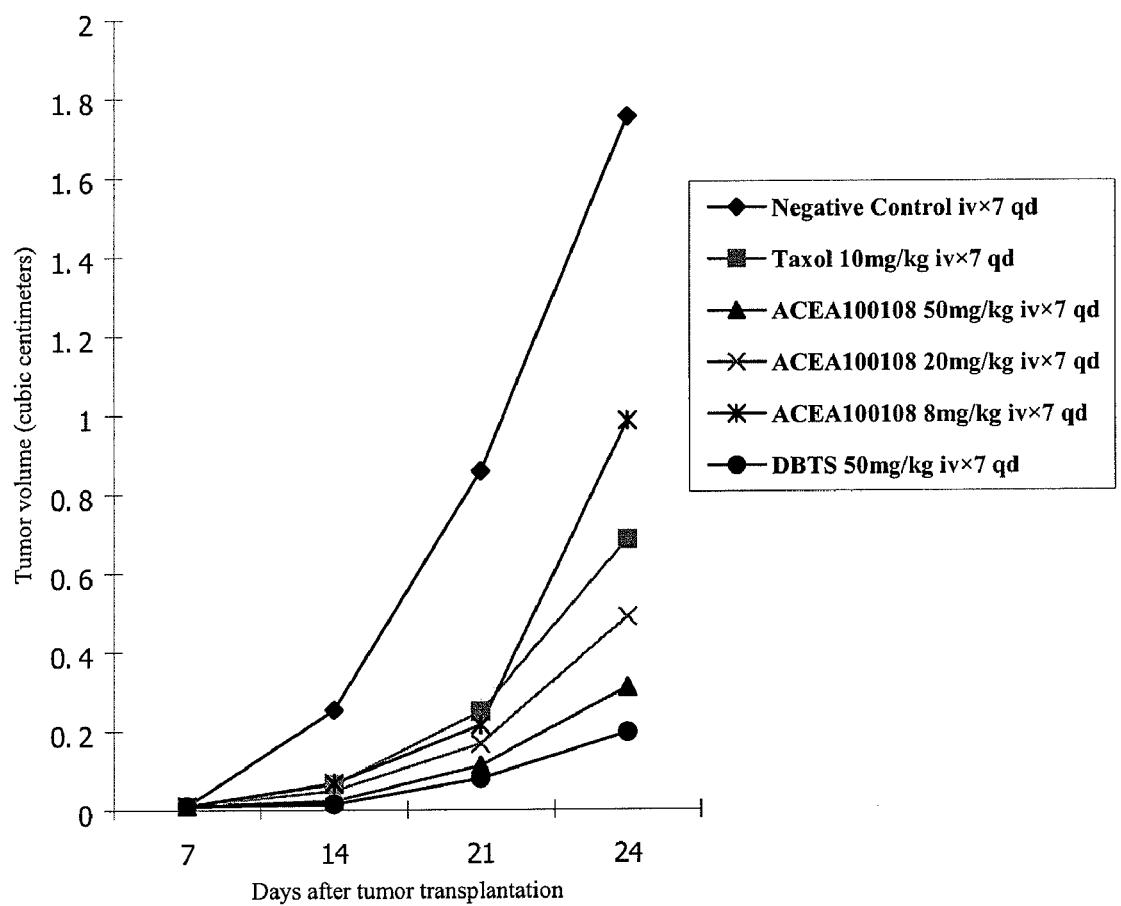
FIG. 17 shows the dynamic change in tumor size in the in vivo antitumor efficacy test of compound ACEA100108 on Bcap-37 human breast cancer that was xenograft transplanted in immunodeficient nude mice by subcutaneous implanting.
Figure 18:
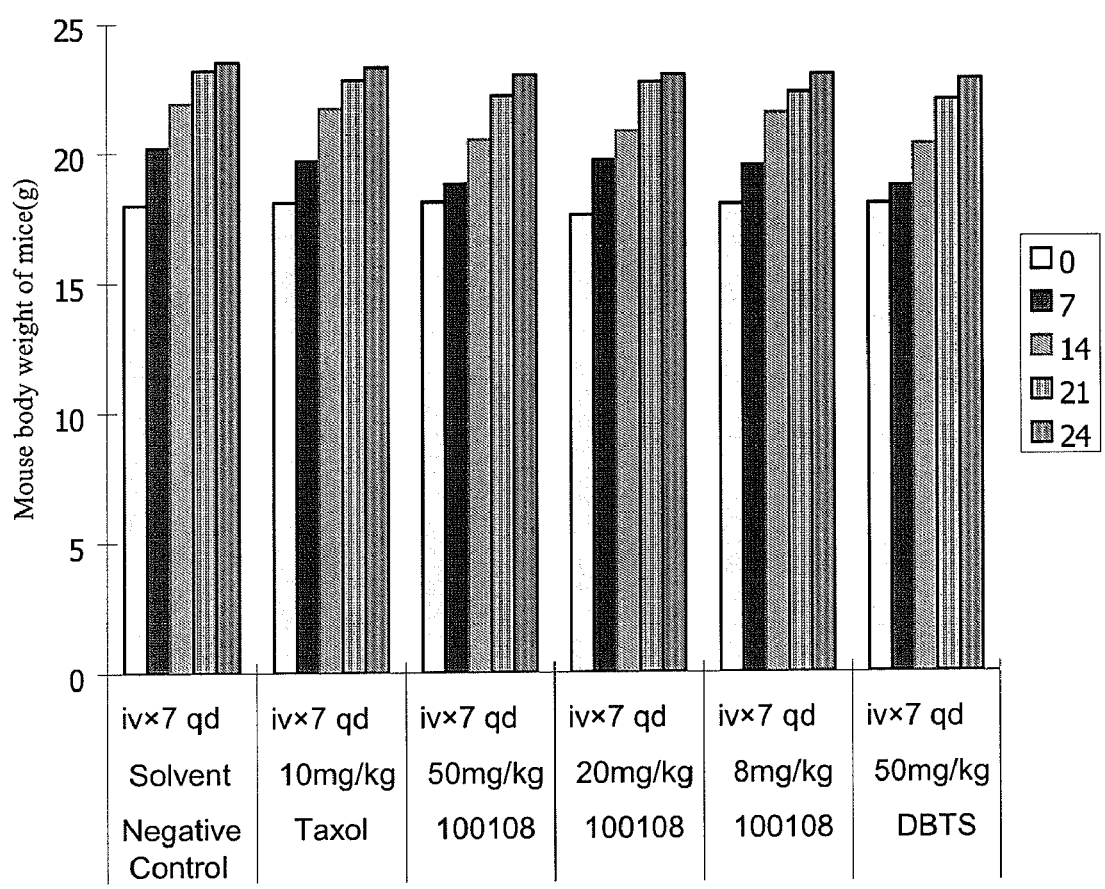
FIG. 18 shows the dynamic change in body weight of carrier mice in the in vivo antitumor efficacy test of compound ACEA100108 (100108) on Bcap-37 human breast cancer that was xenograft-transplanted in immunodeficient nude mice by subcutaneous implanting.

In Bcap-37 human breast cancer xenograft model in nude mice, ACEA100108 showed the average in vivo tumor inhibition rates of 64.13%, 56.10% and 31.40%, respectively, in 50, 25 and 8 mg/kg dosage groups. In the same experiment, DBTS showed the average in vivo tumor inhibition rate of 66.98% for a 50 mg/kg dosage and Taxol showed an average in vivo tumor inhibition rate of 48.84% for the routine administration dosage of 10 mg/kg. The details are provided in Table 18 and FIG. 16, describing an efficacy study of DBTS and ACEA 100108 on Bcap-37 human breast cancer xenograft-transplanted in nude mice. In FIG. 16, the seven rows (1-7, respectively) represent results from the following administered compounds: 1) negative control; 2) solvent; 3) ACEA 100108 (50 mg/kg); 4) ACEA 100108 (20 mg/kg); 5) ACEA 100108 (8 mg/kg); 6) DBTS (50 mg/kg); and 7) positive control (taxol, 10 mg/kg). The test compounds and controls were administered iv×7qd. The dynamic changes of tumor size are summarized in Table 19 and FIG. 17. The dynamic change of body weight of carrier mice results are summarized in Table 20 and FIG. 18.

Figure 19:
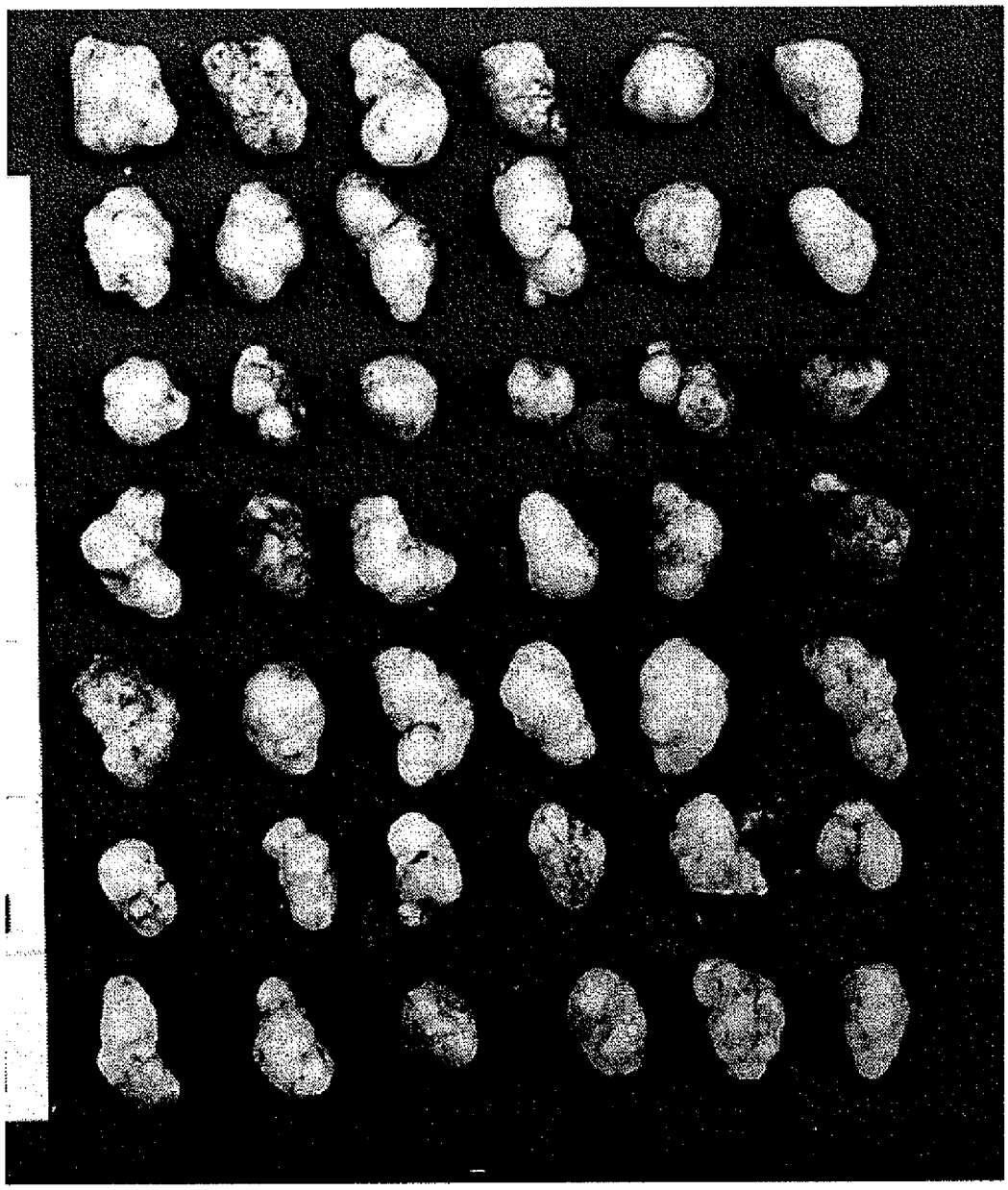
FIG. 19 shows HCT-8 human colon tumors that were xenograft-transplanted in immunodeficient nude mice by subcutaneous seeding and were treated with compound ACEA100108.
Figure 20:
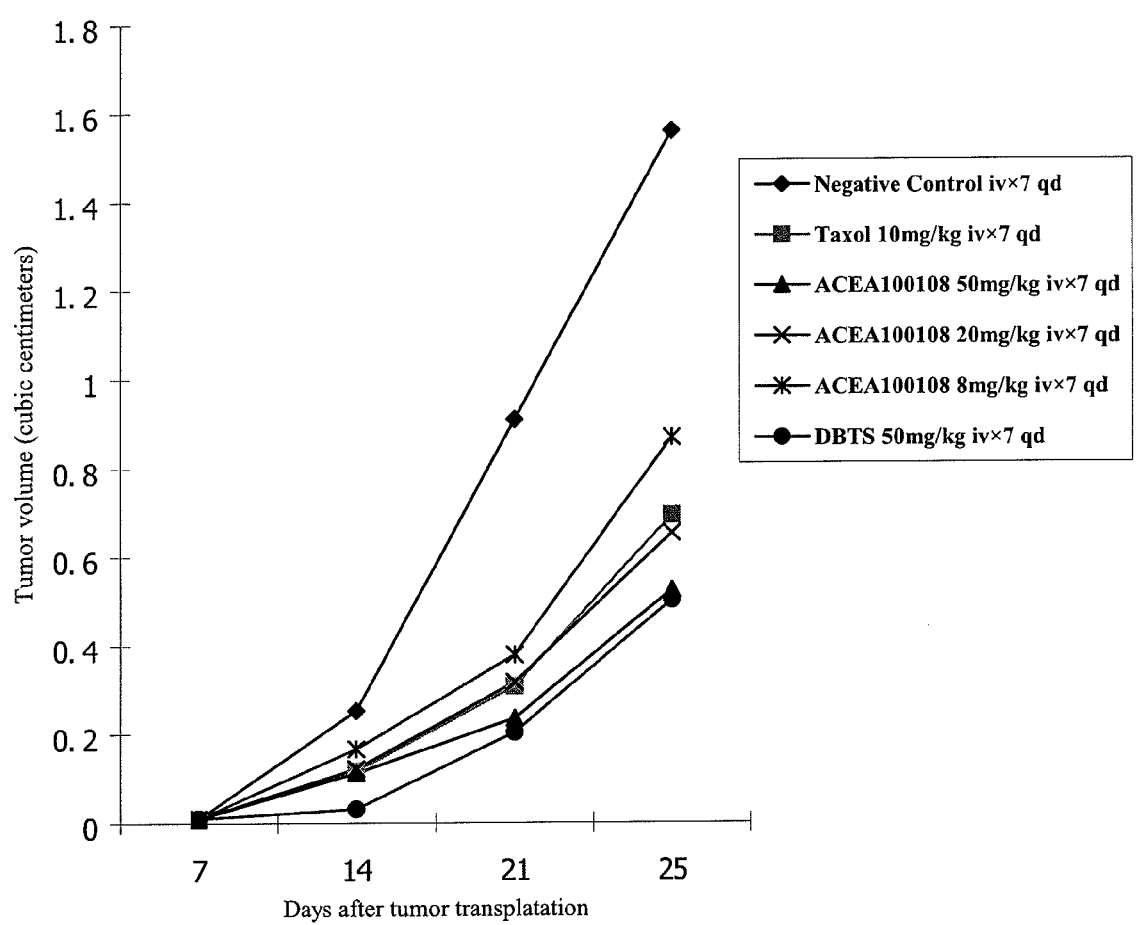
FIG. 20 shows the dynamic change in tumor size in the in vivo antitumor efficacy test of compound ACEA100108 on HCT-8 human colon cancer that was xenograft-transplanted in immunodeficient nude mice by subcutaneous implanting.
Figure 21:
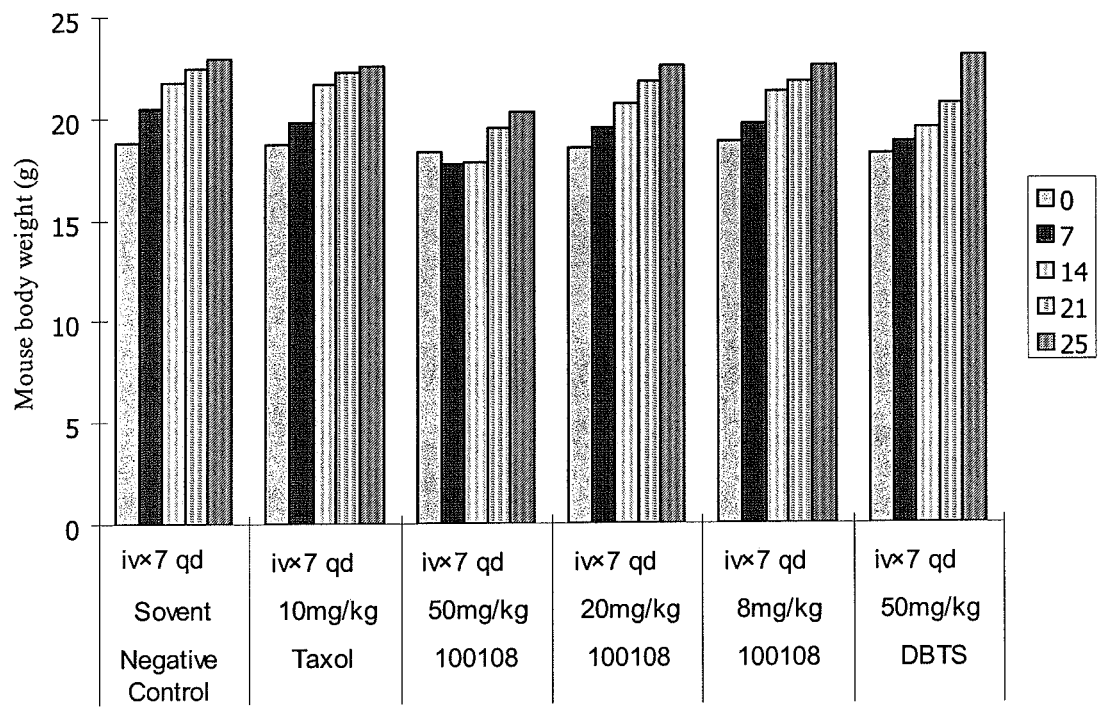
FIG. 21 shows the dynamic change in body weight of carrier mice in the in vivo antitumor efficacy test of compound ACEA100108 (100108) on HCT-8 human colon cancer that was xenograft-transplanted in immunodeficient nude mice by subcutaneous implanting.

In HCT-8 human lung cancer xenograft model in nude mice, ACEA100108 showed the average in vivo tumor inhibition rates of 45.62%, 28.10% and 15.03%, respectively, in 50, 25 and 8 mg/kg dosage groups. In the same experiment, DBTS showed the average in vivo tumor inhibition rate of 46.08% for a 50 mg/kg dosage and Taxol showed an average in vivo tumor inhibition rate of 33.33% for the routine administration dosage of 10 mg/kg. The details are provided in Table 21 and FIG. 19, describing an efficacy study of DBTS and ACEA 100108 on HCT-8 human colon cancer xenograft transplanted in nude mice. In FIG. 19, the seven rows (1-7, respectively) represent results from the following administered compounds: 1) negative control; 2) solvent; 3) ACEA 100108 (50 mg/kg); 4) ACEA 100108 (20 mg/kg); 5) ACEA 100108 (8 mg/kg); 6) DBTS (50 mg/kg); and 7) positive control (taxol, 10 mg/kg). The test compounds and controls were administered iv×7qd. The dynamic changes of tumor size are summarized in Table 22 and FIG. 20. The dynamic change of body weight of carrier mice results are summarized in Table 23 and FIG. 21.

Based on the results from the in vivo evaluation of two mouse tumor models and two humor tumor xenograft models, ACEA100108 may be effectively administered at 50 mg/kg and iv×7qd. In addition, the anticancer effect of ACEA100108 on mouse Lewis lung cancer model and Bcap-37 human breast cancer model is stronger than its effect on HCT-8 human colon cancer model. However, ACEA100108 did not exhibit anticancer effect on P388 mouse leukemia model. Furthermore, for the same dosage and same drug-administration procedure, the anticancer effect for above models of compound ACEA100108 is comparable with that of DBTS, and is better than that of Taxol under routine treatment dosage conditions.

TABLE 16

The in vivo antitumor efficacy of compound ACEA100108 in the mouse Lewis cancer model by subcutaneous seeding.

| Sample | Dosage mg/kg/d | Administration method | Animal No. beginning/end | Animal weight (g) beginning/end | Tumor weight (g) $\bar{X} \pm SD$ | Inhibition rate (%) |
|---|---|---|---|---|---|---|
| ACEA100108 | 100 | ivx7 qd | 10/8 | 20.6/23.4 | 1.08 ± 0.17*** | 60.15 |
| ACEA100108 | 25 | ivx7 qd | 10/10 | 20.1/24.2 | 1.21 ± 0.22*** | 55.35 |
| ACEA100108 | 6.25 | ivx7 qd | 10/10 | 20.3/24.4 | 1.78 ± 0.24*** | 34.32 |
| ACEA100101 | 100 | ivx7 qd | 10/6 | 20.7/23.1 | 1.00 ± 0.15*** | 63.10 |
| ACEA100101 | 25 | ivx7 qd | 10/10 | 20.5/23.6 | 1.14 ± 0.17*** | 57.93 |
| Positive control (Taxol) | 10 | ivx7 qd | 10/10 | 20.4/23.8 | 1.52 ± 0.15*** | 43.91 |
| Negative control | Solvent | ivx7 qd | 20/20 | 20.3/24.7 | 2.71 ± 0.26 | |

***P < 0.01, as compared with the negative control group

TABLE 17

The in vivo antitumor efficacy of compound ACEA100108 in the murine P388 lympholytic leukemia model (transplanted by injection of cancer cells into the peritoneal cavity of host mice).

| Sample | dosage mg/kg/d | administration method | animal No. beginning/end | Beginning animal weight (g) | Average life span $\bar{X} \pm SD$ | Life span ratio % |
|---|---|---|---|---|---|---|
| ACEA100108 | 50 | ivx7 qd | 10/0 | 20.4 | 10.3 ± 0.95 | 106.18 |
| ACEA100108 | 25 | ivx7 qd | 10/0 | 20.4 | 10.4 ± 1.17 | 107.22 |
| ACEA100108 | 12.5 | ivx7 qd | 10/0 | 20.1 | 10.6 ± 0.84 | 109.28 |
| ACEA100101 | 50 | ivx7 qd | 10/0 | 20.7 | 10.6 ± 1.26 | 109.28 |
| Positive control (Taxol) | 10 | ivx7 qd | 10/0 | 20.2 | 10.5 ± 1.18 | 108.25 |
| Positive control (MMC) | 2 | ivx7 qd | 10/1 | 20.6 | 18.1 ± 0.15*** | 186.59 |
| Negative control | Solvent | ivx7 qd | 20/0 | 20.0 | 9.7 ± 0.66 | |

***p < 0.01, as compared with negative control group.
Note:
In general, a compound is regarded as having antitumor efficacy when the life span ratio of carrier mice in the treatment group is more than 125%.

TABLE 18

The in vivo antitumor efficacy of compound ACEA100108 on Bcap-37 human breast cancer that was xenograft-transplanted in immunodeficient nude mice by subcutaneous implanting.

| Sample | dosage mg/kg/d | Administration method | animal No. beginning/end | animal weight (g) beginning/end | tumor weight (g) $\bar{X} \pm SD$ | tumor inhibition rate % | Tumor Volume TV (cm$^3$) | TV inhibition rate % T/C |
|---|---|---|---|---|---|---|---|---|
| ACEA100108 | 50 | ivx7 qd | 6/6 | 18.1/23.0 | 0.617 ± 0.09*** | 64.13 | 0.310 | 17.67 |
| ACEA100108 | 20 | ivx7 qd | 6/6 | 17.6/23.0 | 0.755 ± 0.09*** | 56.10 | 0.488 | 27.82 |
| ACEA100108 | 8 | ivx7 qd | 6/6 | 18.0/23.0 | 1.18 ± 0.23*** | 31.40 | 0.985 | 56.15 |
| ACEA100101 | 50 | ivx7 qd | 6/6 | 18.0/22.8 | 0.568 ± 0.07*** | 66.98 | 0.196 | 11.17 |

TABLE 18-continued

The in vivo antitumor efficacy of compound ACEA100108 on Bcap-37 human breast cancer that was xenograft-transplanted in immunodeficient nude mice by subcutaneous implanting.

| Sample | dosage mg/kg/d | Administration method | animal No. beginning/end | animal weight (g) beginning/end | tumor weight (g) $\overline{X} \pm SD$ | tumor inhibition rate % | Tumor Volume TV (cm³) | TV inhibition rate % T/C |
|---|---|---|---|---|---|---|---|---|
| Positive control Taxol | 10 | ivx7 qd | 6/6 | 18.1/23.3 | 0.88 ± 0.17*** | 48.84 | 0.685 | 39.05 |
| Negative Control | Solvent | ivx7 qd | 12/12 | 18.0/23.5 | 1.72 ± 0.19 | | 1.754 | |

***$P < 0.01$, as compared with negative control group.

TABLE 19

The dynamic change in tumor size in the in vivo antitumor efficacy test of compound ACEA100108 on Bcap-37 human breast cancer that was xenograft-transplanted in immunodeficient nude mice by subcutaneous implanting.

| Sample | Dosage mg/kg | Administration method | Tumor volume (cm³) Days after tumor transplantation | | | | |
|---|---|---|---|---|---|---|---|
| | | | 7 days | | 14 d | 21 d | 24 d |
| Negative Control | Solvent | ivx7 qd | 0.01 | 10/12†† | 0.254 ± 0.06 | 0.858 ± 0.06 | 1.754 ± 0.37 |
| Taxol | 10 mg/kg | ivx7 qd | 0.01 | 4/6†† | 0.065 ± 0.02 | 0.249 ± 0.07 | 0.685 ± 0.14 |
| ACEA100108 | 50 mg/kg | ivx7 qd | 0.01 | 3/6†† | 0.023 ± 0.02 | 0.112 ± 0.03 | 0.31 ± 0.05 |
| ACEA100108 | 20 mg/kg | ivx7 qd | 0.01 | 5/6†† | 0.049 ± 0.03 | 0.167 ± 0.03 | 0.488 ± 0.07 |
| ACEA100108 | 8 mg/kg | ivx7 qd | 0.01 | 4/6†† | 0.068 ± 0.02 | 0.214 ± 0.04 | 0.985 ± 0.4 |
| ACEA100101 | 50 mg/kg | ivx7 qd | 0.01 | 2/6†† | 0.014 ± 0.01 | 0.079 ± 0.01 | 0.196 ± 0.02 |

10/12††: it means that out of total 12 mice, 10 had tumor size sufficiently large when one touches these mice, one can feel tumor in each mouse.

TABLE 20

The dynamic change in body weight of carrier mice in the in vivo antitumor efficacy test of compound ACEA100108 on Bcap-37 human breast cancer that was xenograft-transplanted in immunodeficient nude mice by subcutaneous implanting.

| Samples | dosage (mg/kg/d) | administration method | Body weight of mice (g) | | | | |
|---|---|---|---|---|---|---|---|
| | | | 0 day | 7 day | 14 d | 21 d | 24 d |
| Negative Control | Solvent | ivx7 qd | 18 ± 0.9 | 20.2 ± 0.9 | 21.9 ± 1.1 | 23.2 ± 1.2 | 23.5 ± 0.9 |
| Taxol | 10 | ivx7 qd | 18.1 ± 1.1 | 19.7 ± 1 | 21.7 ± 1 | 22.8 ± 1.2 | 23.3 ± 1.2 |
| ACEA100108 | 50 | ivx7 qd | 18.1 ± 1.1 | 18.8 ± 0.8 | 20.5 ± 1 | 22.2 ± 1.2 | 23 ± 1.2 |
| ACEA100108 | 20 | ivx7 qd | 17.6 ± 0.8 | 19.7 ± 1 | 20.8 ± 1 | 22.7 ± 1.2 | 23 ± 1.2 |
| ACEA100108 | 8 | ivx7 qd | 18 ± 0.6 | 19.5 ± 1 | 21.5 ± 1 | 22.3 ± 1.6 | 23 ± 1.5 |
| ACEA100101 | 50 | ivx7 qd | 18 ± 1 | 18.7 ± 0.8 | 20.3 ± 0.8 | 22 ± 0.6 | 22.8 ± 1.6 |

TABLE 21

The in vivo antitumor efficacy of compound ACEA100108 on HCT-8 human colon cancer that was xenograft-transplanted in immunodeficient nude mice by subcutaneous implanting.

| Sample | dosage (mg/kg/d) | administration method | Animal No. beginning/end | Animal weight (g) beginning/end | tumor weight (g) $\overline{X} \pm SD$ | tumor inhibition rate % | Tumor volume TV (cm³) | TV inhibition rate % T/C |
|---|---|---|---|---|---|---|---|---|
| ACEA100108 | 50 | iv × 7 qd | 6/6 | 18.3/20.3 | 0.832 ± 0.10*** | 45.62 | 0.525 | 33.63 |
| ACEA100108 | 20 | iv × 7 qd | 6/6 | 18.5/22.5 | 1.10 ± 0.23 | 28.10 | 0.654 | 41.89 |
| ACEA100108 | 8 | iv × 7 qd | 6/6 | 18.8/22.5 | 1.30 ± 0.23 | 15.03 | 0.870 | 55.73 |

TABLE 21-continued

The in vivo antitumor efficacy of compound ACEA100108 on HCT-8 human colon cancer that was xenograft-transplanted in immunodeficient nude mice by subcutaneous implanting.

| Sample | dosage (mg/kg/d) | administration method | Animal No. beginning/end | Animal weight (g) beginning/end | tumor weight (g) $\overline{X} \pm SD$ | tumor inhibition rate % | Tumor volume TV (cm$^3$) | TV inhibition rate % T/C |
|---|---|---|---|---|---|---|---|---|
| ACEA100101 | 50 | iv × 7 qd | 6/6 | 18.2/23.0 | 0.825 ± 0.07*** | 46.08 | 0.502 | 32.17 |
| Positive control Taxol | 10 | iv × 7 qd | 6/6 | 18.7/22.58 | 1.02 ± 0.11*** | 33.33 | 0.694 | 44.45 |
| Negative control | Solvent | iv × 7 qd | 12/12 | 18.8/23.9 | 1.53 ± 0.23 | | 1.561 | |

***$P < 0.01$, as compared with negative control.

TABLE 22

The dynamic change in tumor size in the in vivo antitumor efficacy test of compound ACEA100108 on HCT-8 human colon cancer that was xenograft-transplanted in immunodeficient nude mice by subcutaneous implanting.

| Sample | Dosage (mg/kg/d) | Administration method | Tumor volume (cm$^3$) Days after transplantation | | | | |
|---|---|---|---|---|---|---|---|
| | | | 7 day | | 14 d | 21 d | 25 d |
| Negative control | solvent | iv × 7 qd | 0.01 | 12/12†† | 0.253 ± 0.07 | 0.911 ± 0.2 | 1.561 ± 0.26 |
| Taxol | 10 | iv × 7 qd | 0.01 | 6/6†† | 0.116 ± 0.03 | 0.308 ± 0.06 | 0.694 ± 0.15 |
| ACEA100108 | 50 | iv × 7 qd | 0.01 | 6/6†† | 0.112 ± 0.02 | 0.236 ± 0.02 | 0.525 ± 0.14 |
| ACEA100108 | 20 | iv × 7 qd | 0.01 | 6/6†† | 0.122 ± 0.04 | 0.317 ± 0.05 | 0.654 ± 0.09 |
| ACEA100108 | 8 | iv × 7 qd | 0.01 | 6/6†† | 0.166 ± 0.05 | 0.379 ± 0.04 | 0.87 ± 0.15 |
| ACEA100101 | 50 | iv × 7 qd | 0.01 | 4/6†† | 0.031 ± 0.02 | 0.204 ± 0.03 | 0.502 ± 0.18 |

4/6††: it means that out of total 6 mice, 4 had tumor size sufficiently large when one touched these mice, one could feel the tumor.

TABLE 23

The dynamic change in body weight of carrier mice in the in vivo antitumor efficacy test of compound ACEA100108 on HCT-8 human colon cancer that was xenograft-transplanted in immunodeficient nude mice by subcutaneous implanting.

| Sample | Dosage (mg/kg/d) | administration method | Mouse Body weight (g) | | | | |
|---|---|---|---|---|---|---|---|
| | | | 0 Day | 7 d | 14 d | 21 d | 25 d |
| Negative control | Solvent | iv × 7 qd | 18.8 ± 1 | 20.5 ± 0.7 | 21.8 ± 1.1 | 22.4 ± 0.9 | 22.9 ± 1.1 |
| Taxol | 10 | iv × 7 qd | 18.7 ± 1 | 19.8 ± 1.2 | 21.7 ± 1.2 | 22.2 ± 0.8 | 22.5 ± 1.8 |
| ACEA100108 | 50 | iv × 7 qd | 18.3 ± 1 | 17.7 ± 1.2 | 17.8 ± 2.3 | 19.5 ± 1.6 | 20.3 ± 1 |
| ACEA100108 | 20 | iv × 7 qd | 18.5 ± 1 | 19.5 ± 1 | 20.7 ± 1 | 21.8 ± 1.2 | 22.5 ± 1 |
| ACEA100108 | 8 | iv × 7 qd | 18.8 ± 0.8 | 19.7 ± 0.8 | 21.3 ± 1.2 | 21.8 ± 1.2 | 22.5 ± 1 |
| ACEA100101 | 50 | iv × 7 qd | 18.2 ± 1.2 | 18.8 ± 1 | 19.5 ± 1 | 20.7 ± 0.8 | 23 ± 1.3 |

EXAMPLE 4

In Vivo Anticancer Activity of ACEA100108 on ao10/17 Human Ovarian Cancer in Nude Mice To evaluate the in vivo anticancer efficacy of compound ACEA100108, an ao10/17 human ovarian cancer xenograft model in immunodeficient nude mice was used. The cell line and mice were maintained in the Pharmacology Lab of Shanghai Pharmaceutical Industry Institute. For the ao10/17 human ovarian cancer xenograft models, cancer cells were passed twice in vivo before being transplanted into the nude mice for the study. In another word, cultured human ovarian cancer ao10/17 cells in flask were first xenograft-transplanted in immunodeficient nude mice. After the cancer cells grew to a tumor of certain sizes in the nude mice, the tumor was removed form the nude mice and tumor tissues were dissected. The cell suspensions were prepared from the dissected tumor tissue and transplanted back to immunodeficient nude mice again (i.e. the second passage of cancer cells in human cancer xenograft-transplanted model). After the cancer cells grew to certain size, the tumor was removed from nude mice and the tumor tissues were dissected. The cell suspensions were prepared from dissected tissues and were used for the study of human cancer xenograft models described here.

The mice for experiments were $C_{57}BL/6$, DBF1 and BALB/c (nude mice) strains, provided by Academic Sinica, Experimental Animal Center, certification number: SCXK (Shanghai) 2003-0003. The mouse weight was between 18 and 22 g. Only female mice were used in this study. For human tumor xenograft model, the numbers of animals tested were as follows: 6 for each dose group, 6 for positive control group and 12 for negative control (solvent only) group. The high, middle and low doses of ACEA100108 were 50, 25 and 8 mg/kg/d, respectively.

Test control. For negative control, each mouse was administered intravenously with the solvent only having the same volume and same concentration as those used in high dose ACEA100108 test, once a day, for 7 consecutive days. For positive control group, an anticancer compound, Taxol was administered intravenously at 10 mg/kg, once a day for 7 consecutive days. In a reference group, DBTS was administered intravenously at 50 mg/kg, once a day for 7 consecutive days.

Preparation and Administration of Test Compounds. Compound ACEA100108 was dissolved in hydrogenated castor oil (solvent) to have a compound ACEA100108 concentration of 20 mg/ml in the solvent. Each time before use, this solution was diluted in normal saline to achieve desired ACEA100108 concentrations. Each mouse (about 20 g in weight) was administered intravenously with the compound solution of 0.5 mL at a controlled injection speed of 0.5 ml/0.5 min. 24 hrs after the tumor transplantation, intravenous injections of compound solutions into carrier mice were performed once a day, for consecutive 7 days. The high, middle and low dose of compound ACEA100108 was 50, 20 and 8 mg/kg, respectively.

Preparation of Tumor Cells for Transplantation and Determination of Compound Efficacy. To prepare the cancer cells for human ovarian cancer xenograft model, the fast growing tumors were first removed from the transplanted tumor mice. The tumor tissues were grounded in normal saline (1:6 for tumor volume to saline volume) and tumor cell suspensions were prepared in the normal saline. 0.2 ml of cell suspension was subcutaneously injected into the axillary region (right-side) of each mouse. Twenty four hours after the transplantation, mice were administered with a given dose of ACEA100108, or with solvent only which serves as the negative control, or with 10 mg/kg Taxol which served as positive control, or with 50 mg/kg DBTS which served as a reference test. Between two and four weeks after transplantation, mice were sacrificed and the transplanted tumors were removed from experimental mice. Each removed solid tumor was weighed; the tumor inhibition rate in each dosage group was calculated according to equation (2) in Example 1.

For the human ovarian cancer xenograft model, all used materials, including animal food, animal cage, supporting materials and apparatus contacted by animals, were high-pressure sterilized. Nude mice were maintained in laminar flow shelves under SPF condition. After tumor transplantation, mouse weight and tumor size in each compound dosage group were dynamically monitored and plotted. The tumor size was determined by measuring the major axis (a) and minor axis (b) of the tumor, and tumor volume was calculated according to the equation (3) in Example 3.

Figure 22:
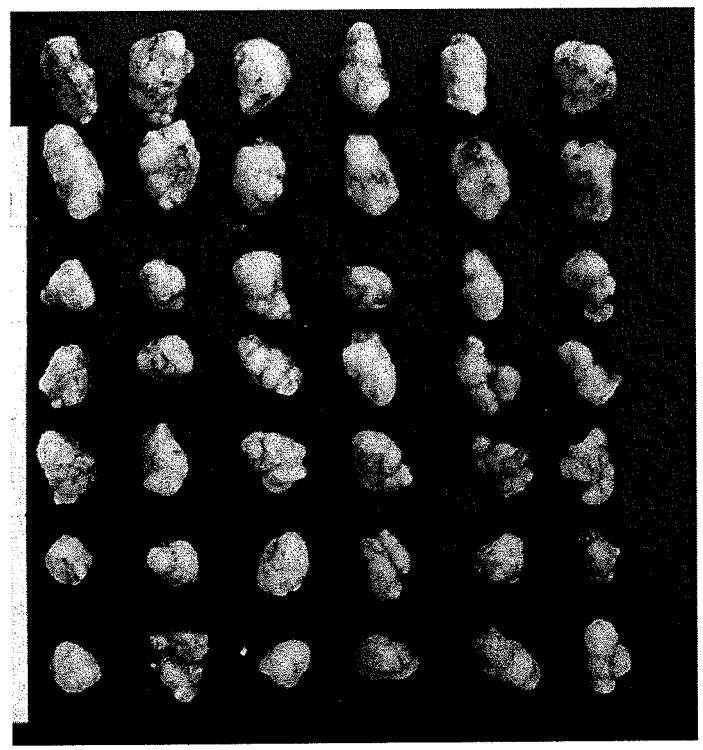
FIG. 22 shows ao10/17 human ovarian tumors that were xenograft-transplanted in immunodeficient nude mice by subcutaneous seeding and were treated with compound ACEA100108.

Results. In a o10/17 human ovarian cancer xenograft model in nude mice, ACEA100108 showed the average in vivo tumor inhibition rates of 53.40%, 46.67% and 33.19%, respectively, in 50, 25 and 8 mg/kg dosage groups. In the same experiment, DBTS showed the average in vivo tumor inhibition rate of 57.30% for a 50 mg/kg dosage and Taxol showed an average in vivo tumor inhibition rate of 45.39% for the routine administration dosage of 10 mg/kg. The details are provided in Table 24 and FIG. 22, describing an efficacy study of DBTS and ACEA 100108 on ao10/17 human ovarian cancer xenograft-transplanted in nude mice. In FIG. 22, the seven rows (1-7, respectively) represent results from the following administered compounds: 1) negative control; 2) solvent; 3) ACEA 100108 (50 mg/kg); 4) ACEA 100108 (20 mg/kg); 5) ACEA 100108 (8 mg/kg); 6) DBTS (50 mg/kg); and 7) positive control (taxol, 10 mg/kg). The test compounds and controls were administered iv at 7qd.

Figure 23:
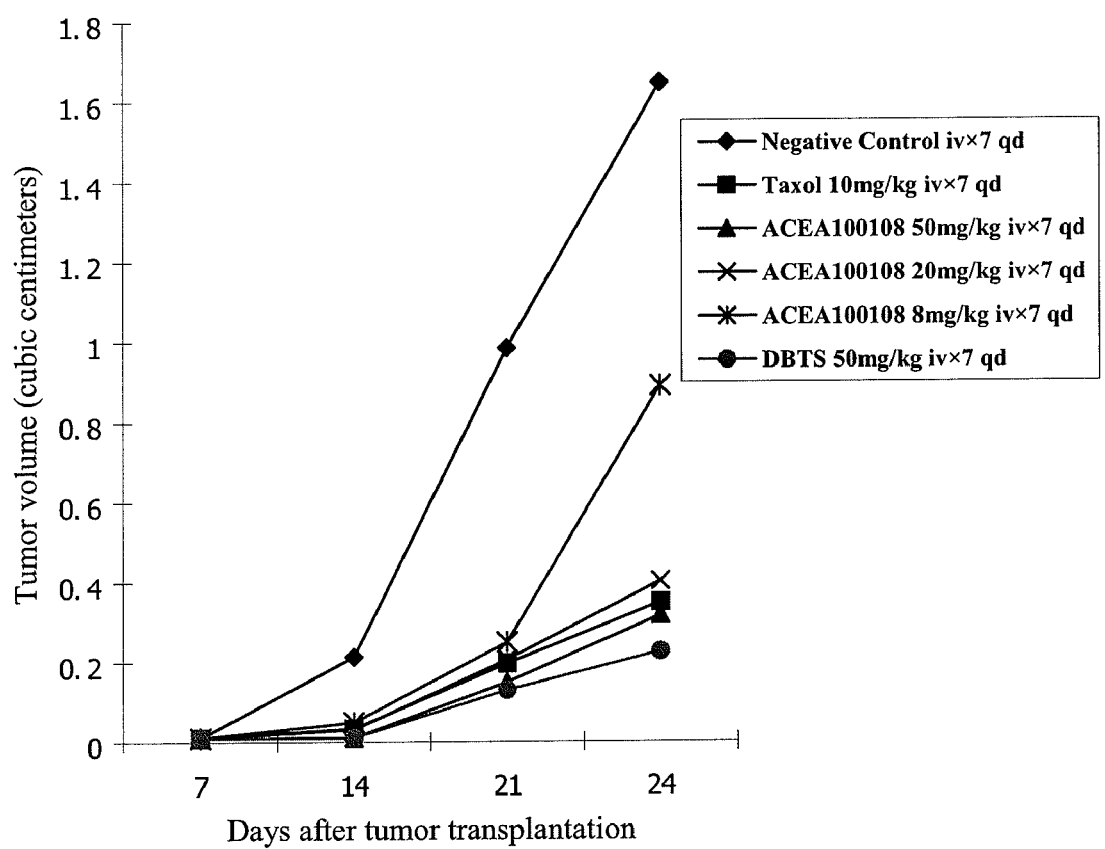
FIG. 23 shows the dynamic change in tumor size in the in vivo antitumor efficacy test of compound ACEA100108 on ao10/17 human ovarian cancer that was xenograft transplanted in immunodeficient nude mice by subcutaneous implanting.
Figure 24:
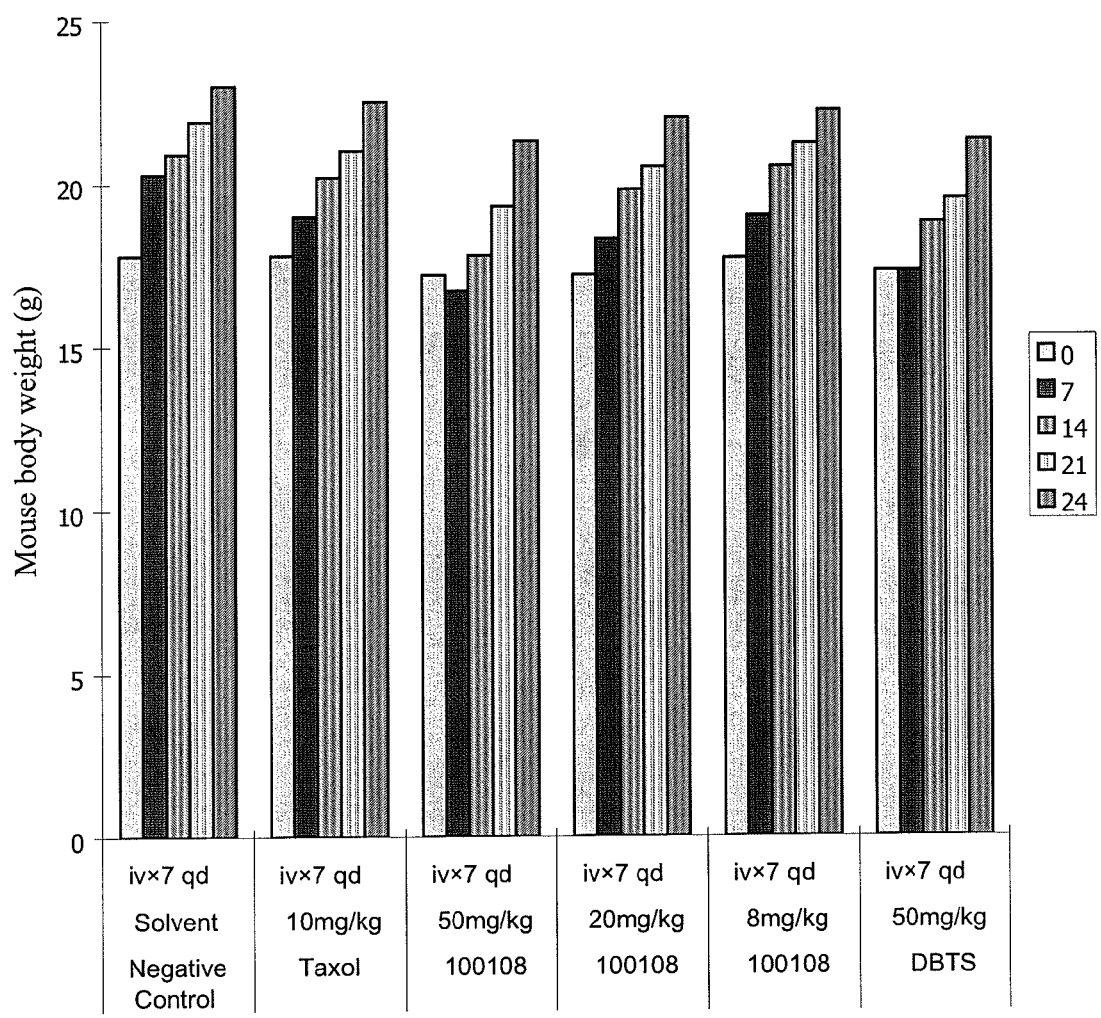
FIG. 24 shows the dynamic change in body weight of carrier mice in the in vivo antitumor efficacy test of compound ACEA100108 (100108) on ao10/17 human ovarian cancer that was xenograft-transplanted in immunodeficient nude mice by subcutaneous implanting.

The dynamic changes of tumor size are summarized in Table 25 and FIG. 23. The dynamic change of body weight of carrier mice results are summarized in Table 26 and FIG. 24. For the same dosage and same drug-administration procedure, the anticancer effect of compound ACEA100108 in ao10/17 human ovarian cancer models is comparable with that of compound ACEA100101, and is better than that of Taxol under regular treatment dosage conditions.

TABLE 24

The in vivo antitumor efficacy of compound ACEA100108 on ao10/17 human ovarian cancer xenograft transplanted in immunodeficient nude mice (subcutaneously transplanted tumor).

| Sample | Dosage mg/kg/d | Administration Method | Animal No. Beginning/end | Body weight (g) Beginning/end | Tumor Weight (g) $\overline{X} \pm SD$ | Tumor Inhibition Rate % |
|---|---|---|---|---|---|---|
| ACEA100108 | 50 | iv × 7 qd | 6/6 | 17.2/21.3 | 0.657 ± 0.13*** | 53.40 |
| ACEA100108 | 20 | iv × 7 qd | 6/6 | 17.2/22.0 | 0.752 ± 0.12*** | 46.67 |
| ACEA100108 | 8 | iv × 7 qd | 6/6 | 17.7/22.2 | 0.942 ± 0.14*** | 33.19 |
| ACEA100101 | 50 | iv × 7 qd | 6/6 | 17.3/21.3 | 0.602 ± 0.10*** | 57.30 |
| Positive Control (Taxol) | 10 | iv × 7 qd | 6/6 | 17.8/22.5 | 0.77 ± 0.12*** | 45.39 |
| Negative Control | Solvent | iv × 7 qd | 12/12 | 17.8/23.0 | 1.41 ± 0.17 | |

***$P < 0.01$, as compared with negative control.

TABLE 25

The dynamic change in tumor size in the in vivo antitumor efficacy test of compound ACEA100108 on ao10/17 human ovarian cancer that was xenograft-transplanted in immunodeficient nude mice (subcutaneously transplanted tumor).

| Sample | Dosage mg/kg | Administration method | Tumor volume (cm³) Days after tumor transplantation | | | |
|---|---|---|---|---|---|---|
| | | | 7 D | 14 d | 21 d | 24 d |
| Negative Control | Solvent | iv × 7 qd | 0.01 ± 7/12†† | 0.213 ± 0.03 | 0.985 ± 0.03 | 1.648 ± 0.22 |
| Taxol | 10 | iv × 7 qd | 0.01 ± 2/6†† | 0.033 ± 0.02 | 0.196 ± 0.03 | 0.349 ± 0.08 |
| ACEA100108 | 50 | iv × 7 qd | 0.01 ± 1/6†† | 0.01 ± 6/6†† | 0.148 ± 0.02 | 0.316 ± 0.06 |
| ACEA100108 | 20 | iv × 7 qd | 0.01 ± 2/6†† | 0.03 ± 0.02 | 0.206 ± 0.03 | 0.402 ± 0.1 |
| ACEA100108 | 8 | iv × 7 qd | 0.01 ± 3/6†† | 0.048 ± 0.03 | 0.249 ± 0.05 | 0.89 ± 0.39 |
| ACEA100101 | 50 | iv × 7 qd | 0.01 ± 2/6†† | 0.01 ± 6/6†† | 0.129 ± 0.01 | 0.225 ± 0.04 |

7/12††: it means that out of total 12 mice, 7 had tumor size sufficiently large when one touched the mouse, one could feel the tumor.

TABLE 26

The dynamic change in body weight of carrier mice in the in vivo antitumor efficacy test of compound ACEA100108 on ao10/17 human ovarian cancer that was xenograft-transplanted in immunodeficient nude mice by subcutaneous implanting.

| Sample | Dosage (mg/kg) | Administration method | Body weight of mice (g) | | | | |
|---|---|---|---|---|---|---|---|
| | | | 0 d | 7 d | 14 d | 21 d | 24 d |
| Negative Control | Solvent | iv × 7 qd | 17.8 ± 1.1 | 20.3 ± 0.8 | 20.9 ± 0.9 | 21.9 ± 0.9 | 23.0 ± 1 |
| Taxol | 10 | iv × 7 qd | 17.8 ± 1.2 | 19 ± 0.9 | 20.2 ± 1.2 | 21.0 ± 0.9 | 22.5 ± 1 |
| ACEA100108 | 50 | iv × 7 qd | 17.2 ± 0.8 | 16.7 ± 0.8 | 17.8 ± 1.5 | 19.3 ± 1 | 21.3 ± 1.2 |
| ACEA100108 | 20 | iv × 7 qd | 17.2 ± 1.2 | 18.3 ± 0.8 | 19.8 ± 0.8 | 20.5 ± 1 | 22.0 ± 1.4 |
| ACEA100108 | 8 | iv × 7 qd | 17.7 ± 0.5 | 19 ± 0.6 | 20.5 ± 1 | 21.2 ± 0.8 | 22.2 ± 0.8 |
| ACEA100101 | 50 | iv × 7 qd | 17.3 ± 1 | 17.3 ± 1.4 | 18.8 ± 1.2 | 19.5 ± 1 | 21.3 ± 1.2 |

EXAMPLE 5

In Vivo Anticancer Activity of ACEA100108 on Bcap-37 Human Breast Cancer in Nude Mice To evaluate the in vivo anticancer efficacy of compound ACEA100108, Bcap-37 human breast cancer xenograft model in immunodeficient nude mice was used. The cell line and mouse model are maintained in the Pharmacology Lab of Shanghai Pharmaceutical Industry Institute. For the Bcap-37 human breast cancer xenograft models, cancer cells were passed twice in vivo before being transplanted into the nude mice for the study. In another word, cultured human breast cancer Bcap-37 cells in flask were first xenograft-transplanted in immunodeficient nude mice. After the breast cancer cells grew to a tumor of certain sizes in the nude mice, the tumor was removed form the nude mice and tumor tissues were dissected. The cell suspensions were prepared from the dissected tumor tissue and transplanted back to immunodeficient nude mice again (i.e. the second passage of cancer cells in human cancer xenograft-transplanted model). After the cancer cells grew to certain size, the tumor was removed from nude mice and the tumor tissues were dissected. The cell suspensions were prepared from dissected tissues and were used for the study of human cancer xenograft models described here.

The mice for experiments were BALB/c (nude mice) strains, provided by Academic Sinica, Experimental Animal Center, certification number: SCXK (Shanghai) 2003-0003. The mouse weight was between 18 and 22 g. Only female mice were used in this study. For human tumor xenograft model, the numbers of animals tested were as follows: 6 for each dose group, 6 for positive control group and 12 for negative control (solvent only) group. The high, middle and low doses of ACEA100108 were 50, 25 and 8 mg/kg/d, respectively.

Test control. For negative control, each mouse was administered intravenously with the solvent only having the same volume and same concentration as those used in high dose ACEA100108 test, once a day, for 7 consecutive days. For positive control group, an anticancer compound, Taxol was administered intravenously at 10 mg/kg, once a day for 7 consecutive days.

Preparation and Administration of Test Compounds. Compound ACEA100108 was dissolved in hydrogenated castor oil (solvent) to have a ACEA100108 concentration of 20 mg/ml in the solvent. Each time before use, this solution was diluted in normal saline to achieve desired ACEA100108 concentrations. Each mouse (about 20 g in weight) was administered intravenously with the compound solution of 0.5 mL at a controlled injection speed of 0.5 ml/0.5 min. Seven days after the tumor transplantation, the transplanted tumors grew to size sufficiently large that could be felt by hands when one touched the animal. From that time on, intravenous injections of compound solutions into carrier mice were performed once a day, for consecutive 7 or 10 days. The high, middle and low dose of ACEA100108 was 50, 20 and 8 mg/kg, respectively.

Preparation of Tumor Cells for Transplantation and Determination of Compound Efficacy. To prepare the cancer cells for human breast cancer xenograft model, the fast growing tumors were first removed from the transplanted tumor mice. The tumor tissues were grounded in normal saline (1:6 for tumor volume to saline volume) and tumor cell suspensions were prepared in the normal saline having cell concentration of $2\text{-}4\times10^7$ cells/ml. 0.2 ml of cell suspension was subcutaneously injected into the axillary region (right-side) of each mouse. About seven days after the transplantation, tumors in the mice grew sufficiently large so that tumor could be felt by hands when one touched the animals. From that time on, mice were administered with a given dose of ACEA100108, or with solvent only which serves as the negative control, or with 10 mg/kg Taxol which served as positive control. Between three and four weeks after transplantation, mice were sacrificed and the transplanted tumors were removed from experimental mice. Each removed solid tumor was weighed; the tumor inhibition rate in each dosage group was calculated according to equation (2) in Example 1. Based on the tumor volume, another parameter, namely, tumor volume inhibition rate was also calculated, according to T/C(%)=average volume of tumor in the compound treated group/average weight of tumor in the negative control group×100% (5)

For the human breast cancer xenograft model, all used materials, including animal food, animal cage, supporting materials and apparatus contacted by animals, were high-pressure sterilized. Nude mice were maintained in laminar flow shelves under SPF condition. After tumor transplantation, mouse weight and tumor size in each compound dosage group were dynamically monitored and recorded. The tumors size was determined by measuring the major axis (a) and minor axis (b) of the tumor, and tumor volume was calculated according to the equation (3) in Example 3.

Figure 25:
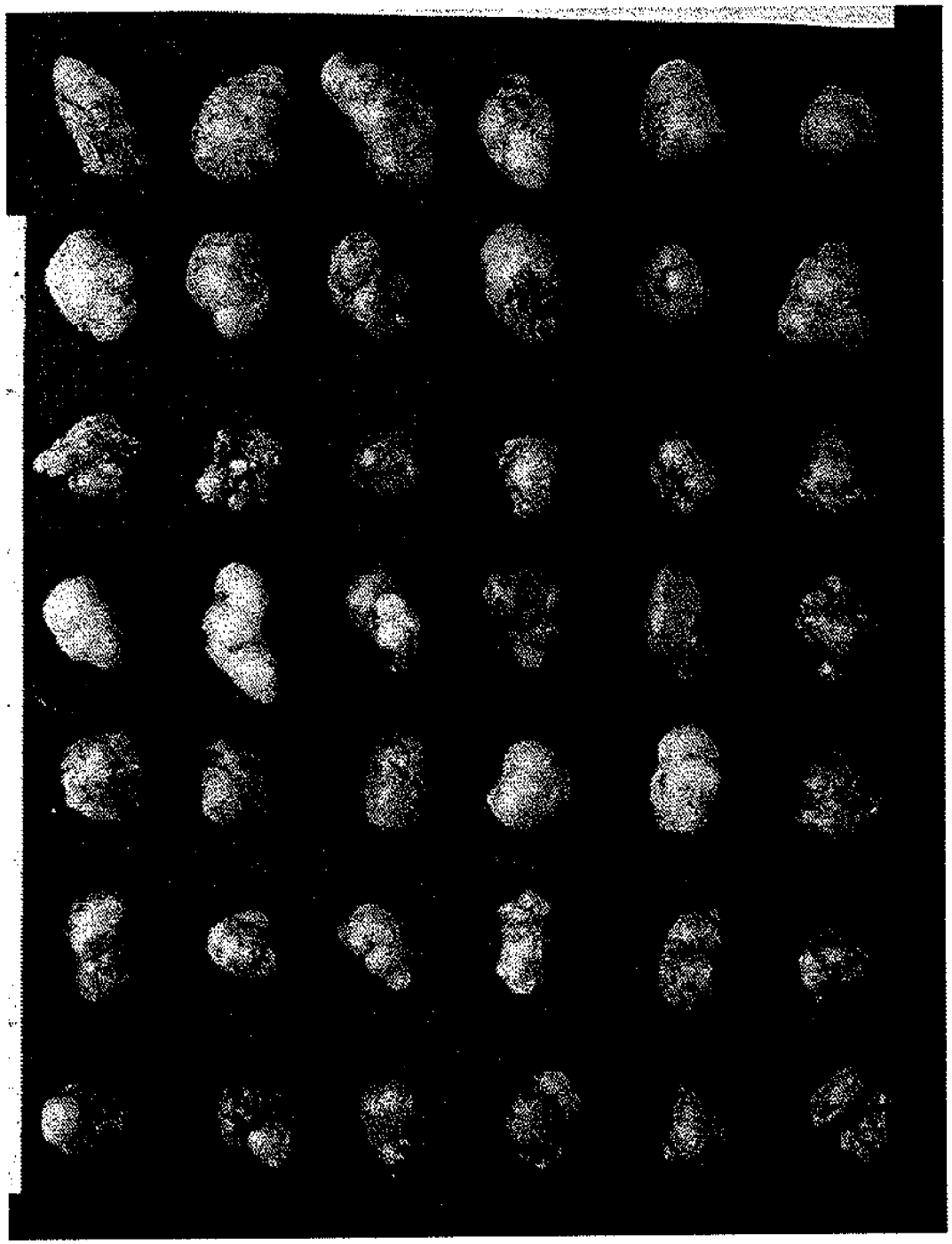
FIG. 25 shows Bcap-37 human breast tumors that were xenograft-transplanted in immunodeficient nude mice by subcutaneous implanting and were treated with compound ACEA100108.

Results. In Bcap-37 human breast cancer xenograft model in nude mice, ACEA100108 showed the average in vivo tumor inhibition rates of 52.24%, 47.31% and 28.21%, respectively, in 50, 20 and 8 mg/kg dosage groups when the compound was administered according to iv×7qd procedure. Furthermore, it showed the average in vivo tumor inhibition rates of 56.92% for 50 mg/kg dosage when the compound was administered according to 10×qd procedure. In the same experiment, Taxol showed an average in vivo tumor inhibition rate of 44.33% for the routine administration dosage of 10 mg/kg. The details are provided in Table 27 and FIG. 25, describing an efficacy study of ACEA 100108 on Bcap-37 human breast cancer xenograft-transplanted in nude mice. In FIG. 25, the seven rows (1-7, respectively) represent results from the following administered compounds: 1) negative control; 2) solvent; 3) ACEA 100108 (50 mg/kg); 4) ACEA 100108 (20 mg/kg); 5) ACEA 100108 (8 mg/kg); 6) ACEA 100108 (50 mg/kg); and 7) positive control (taxol, 10 mg/kg). The test compounds and controls were administered iv at 7qd, except for ACEA 1001008 at 50 mg/kg, which was administered iv×10qd. The result of tumor volume inhibition rates are shown in Table 28. The dynamic changes of tumor size are summarized in Table 26. The dynamic change of body weight of carrier mice results are summarized in Table 27.

In the Bcap-37 human breast cancer xenograft model in nude mice, ACEA100108 showed a tumor inhibition rate above 50% for a compound administration procedure in which compound was administered after the tumor grew to sufficient large so that the tumor could be felt by hands. Furthermore, when dosing times of the compound in the nude mice increased, there was no apparent increased toxic effect to mice, while there was increased tumor inhibition. In addition, the middle dosage of ACEA100108 administered here into nude mice showed a better anticancer efficacy than that of the routine treatment dosage of Taxol.

TABLE 27

The in vivo antitumor efficacy of compound ACEA100108 on Bcap-37 human breast cancer xenograft transplanted in immunodeficient nude mice (subcutaneously transplanted tumor). (Based on tumor weight).

| Sample | Dosage mg/kg/d | Administration Method | Animal No. Beginning/end | Body weight (g) Beginning/end | Tumor Weight (g) $\overline{X} \pm SD$ | Tumor Inhibition Rate C − T/C % |
|---|---|---|---|---|---|---|
| ACEA100108 | 50 | iv × 7 qd | 6/6 | 18.2/22.8 | 0.745 ± 0.10*** | 52.24 |
| ACEA100108 | 20 | iv × 7 qd | 6/6 | 18.8/24.3 | 0.822 ± 0.12*** | 47.31 |
| ACEA100108 | 8 | iv × 7 qd | 6/6 | 18.5/24.0 | 1.12 ± 0.18*** | 28.21 |
| ACEA100108 | 50 | iv × 10 qd | 6/6 | 18.8/21.2 | 0.672 ± 0.10*** | 56.92 |
| Positive Control (Taxol) | 10 | iv × 7 qd | 6/6 | 18.8/24.3 | 0.92 ± 0.07*** | 41.03 |
| Negative Control | Solvent | iv × 7 qd | 12/12 | 18.6/24.8 | 1.56 ± 0.14 | |

***P < 0.01, as compared with negative control.

TABLE 28

The in vivo antitumor efficacy of compound ACEA100108 on Bcap-37 human breast cancer xenograft transplanted in immunodeficient nude mice (subcutaneously transplanted tumor). (Based on tumor volume)

| Sample | Dosage mg/kg/d | Administration Method | Animal No. Beginning/end | Body weight (g) Beginning/end | Tumor Volume (g) $\overline{X} \pm SD$ | Tumor Volume Inhibition T/C % |
|---|---|---|---|---|---|---|
| ACEA100108 | 50 | iv × 7 qd | 6/6 | 18.2/22.8 | 0.485 ± 0.06*** | 26.91 |
| ACEA100108 | 20 | iv × 7 qd | 6/6 | 18.8/24.3 | 0.740 ± 0.18*** | 41.06 |
| ACEA100108 | 8 | iv × 7 qd | 6/6 | 18.5/24.0 | 0.962 ± 0.23*** | 53.38 |
| ACEA100108 | 50 | iv × 10 qd | 6/6 | 18.8/21.2 | 0.280 ± 0.04*** | 15.53 |

TABLE 28-continued

The in vivo antitumor efficacy of compound ACEA100108 on Bcap-37 human breast cancer xenograft transplanted in immunodeficient nude mice (subcutaneously transplanted tumor). (Based on tumor volume)

| Sample | Dosage mg/kg/d | Administration Method | Animal No. Beginning/end | Body weight (g) Beginning/end | Tumor Volume (g) $\bar{X} \pm SD$ | Tumor Volume Inhibition T/C % |
|---|---|---|---|---|---|---|
| Positive Control (Taxol) | 10 | iv × 7 qd | 6/6 | 18.8/24.3 | 0.799 ± 0.23*** | 44.33 |
| Negative Control | Solvent | iv × 7 qd | 12/12 | 18.6/24.8 | 1.802 ± 0.43 | |

***P < 0.01, as compared with negative control.

TABLE 29

The dynamic change in tumor size in the in vivo antitumor efficacy test of compound ACEA100108 on Bcap-37 human breast cancer that was xenograft-transplanted in immunodeficient nude mice (subcutaneously transplanted tumor).

| Sample | Dosage mg/kg | Administration method | Tumor volume (cm³) Days after tumor transplantation | | | | |
|---|---|---|---|---|---|---|---|
| | | | | 7 d | 14 d | 21 d | 24 d |
| Negative Control | Solvent | iv × 7 qd | 0.01 | 12/12†† | 0.282 ± 0.07 | 0.962 ± 0.25 | 1.802 ± 0.43 |
| Taxol | 10 | iv × 7 qd | 0.01 | 6/6†† | 0.103 ± 0.02 | 0.283 ± 0.05 | 0.799 ± 0.23 |
| ACEA100108 | 50 | iv × 7 qd | 0.01 | 6/6†† | 0.049 ± 0.02 | 0.169 ± 0.03 | 0.485 ± 0.06 |
| ACEA100108 | 20 | iv × 7 qd | 0.01 | 6/6†† | 0.087 ± 0.01 | 0.23 ± 0.04 | 0.74 ± 0.18 |
| ACEA100108 | 8 | iv × 7 qd | 0.01 | 6/6†† | 0.107 ± 0.02 | 0.27 ± 0.03 | 0.962 ± 0.23 |
| ACEA100108 | 50 | iv × 10 qd | 0.01 | 6/6†† | 0.048 ± 0.03 | 0.114 ± 0.02 | 0.28 ± 0.04 |

12/12††: it means that out of total 12 mice, all had tumor size sufficiently large when one touched the mouse, one could feel the tumor.

TABLE 30

The dynamic change in body weight of carrier mice in the in vivo antitumor efficacy test of compound ACEA100108 on Bcap-37 human breast cancer that was xenograft-transplanted in immunodeficient nude mice by subcutaneous implanting.

| Sample | Dosage (mg/kg) | Administration method | Body weight of mice (g) | | | | |
|---|---|---|---|---|---|---|---|
| | | | 0 d | 7 d | 14 d | 21 d | 24 d |
| Negative Control | Solvent | iv × 7 qd | 18.6 ± 0.9 | 21.1 ± 1.2 | 21.9 ± 1.2 | 23.5 ± 1.2 | 24.8 ± 1.1 |
| Taxol | 10 | iv × 7 qd | 18.8 ± 1 | 20.5 ± 1 | 21.5 ± 1.6 | 23.0 ± 1.4 | 24.3 ± 0.8 |
| ACEA100108 | 50 | iv × 7 qd | 18.2 ± 1.2 | 19.3 ± 1 | 20.7 ± 1.2 | 21.8 ± 1.5 | 22.8 ± 1.5 |
| ACEA100108 | 20 | iv × 7 qd | 18.8 ± 1.2 | 19.5 ± 1 | 21.2 ± 1.5 | 22.3 ± 1.6 | 24.3 ± 0.8 |
| ACEA100108 | 8 | iv × 7 qd | 18.5 ± 1 | 19.8 ± 1.5 | 21.7 ± 1.4 | 23.2 ± 1.5 | 24 ± 1.4 |
| ACEA100108 | 50 | iv × 10 qd | 18.8 ± 1 | 19.7 ± 1 | 20.3 ± 1.4 | 21.5 ± 1.8 | 21.2 ± 1.2 |

EXAMPLE 6

Acute Toxicity Test of DBTS and Compound ACEA100108

Determination of the Intravenous Injection $LD_{50}$ in Mice

The experiments to test DBTS and ACEA100108 acute toxicity were performed in mice. The test mice were randomly divided into six groups (five dosing groups and one control group). Each group contained 20 Kunming strain mice, and among them, 50% were male and 50% were female. After administration of a single dose of DBTS or ACEA100108 via intravenous injection (i.v.), the acute response to DBTS or ACEA100108 compound, and the death of the treated mice during the first two weeks were monitored and recorded. The $LD_{50}$ value was calculated using the Bliss method. The mouse single i.v. dose $LD_{50}$ value of DBTS was 258.53 mg/kg (234.96 to 284.46 mg/kg), and the mouse single i.v. dose $LD_{50}$ value of ACEA100108 was 316 mg/kg (284.26-351.28 mg/kg).

Materials and Method. The test chemical compound were DBTS and ACEA100108, which were dissolved into hydrogenated castor oil in the pre-warmed water bath and made as a 20 mg/ml solution. The solution was further diluted to desired experiment concentrations with the normal saline. The administration volume was 0.5 ml i.v. per mouse and the injection speed was 0.5 ml/0.5 min.

The experimental mice were Kunming strain, provided by the Experimental Animal Department, Shanghai Pharmaceutical Industry Institute. The certificate number of the facility was Animal Facility Certification Number 107. The average weight of the mice was 18-20 gram. Each test group contained 20 Kunming strain mice, and among them, 10 mice were male and 10 mice were female. Five experimental doses were used, which were 400 mg/kg, 320 mg/kg, 256 mg/kg, 204.8 mg/kg and 163.8 mg/kg. The mice in the control group were only given the same volume of the solvent, which were diluted hydrogenated castor oil. All the testing mice were given a single intravenous injection of DBTS, ACEA100108, or the solvent that served as the control at the injection speed of 0.5 ml/0.5 min. The acute response to DBTS, ACEA100108 or the solvent immediately after the administration, as well as weight change, and the death within the first two weeks of the administration were monitored and recorded. The intravenous injection $LD_{50}$ values in mice were calculated using the Bliss method.

Result. Immediately after intravenous injection, mice showed behavioral abnormalities, which included jumping, running, convulsion, and shortness of breath (accelerated respiration). At high dose groups, some mice died of convulsive seizure within 3 min after the injection. The death occurred within one hour of the administration and the peak was at the $12^{th}$ hour of the administration. No pathological abnormality in the organs of the dead mice was found by autopsy. The survival mice showed no severe toxic symptoms except early reduced activities and loose hair, which were gradually recovered, and there was no delayed toxic manifestations seen within the 14 day following up monitoring. Although survival mice were healthy and behaved normal, the mice showed weight loss to some degree. Based experimental data, the mouse single i.v. dose $LD_{50}$ value of DBTS was 258.53 mg/kg (234.96 to 284.56 mg/kg), and the mouse single i.v. dose $LD_{50}$ value of ACEA100108 was 316 mg/kg (284.26-351.28 mg/kg). There was no significant difference in $LD_{50}$ values between male mice and female mice (p value >0.05). The acute toxicity results for DBTS and ACEA100108 were summarized in Tables 31 and 32. To evaluate the possible toxic effect of the solvent on the mice, the mice in the control group were administered with the same volume of the solvent. The mice given the solvent showed early abnormal manifestations and weight loss to a degree less than the mice dosed with DBTS or ACEA100108. This suggests that the acute toxic effects seen in the dosing mice are related to DBTS or ACEA100108.

TABLE 31

Acute toxicity in the Kunming mice given a single intravenous injection dose of DBTS.

| Sex | Dosage Mg/kg | Animal number | \multicolumn{10}{c}{Distribution of dead animals on each day after the single intravenous injection} | Percentage of dead animals % | $LD_{50}$ (95% CL) g/kg | Average animal weight (g) Beginning | End |
|---|---|---|---|---|---|---|---|---|---|---|---|---|---|---|---|---|
| | | | 1 | 2 | 3 | 4 | 5 | 6 | 7 | 8 | 9 | 10 - - - 14 | | | | |
| Male | 400 | 10 | 10 | 0 | 0 | 0 | 0 | 0 | 0 | 0 | 0 | 0 - - - 0 | 100 | 261.08 | 20.1 | — |
| | 320 | 10 | 7 | 1 | 1 | 0 | 0 | 0 | 0 | 0 | 0 | 0 - - - 0 | 90 | (230.3~295.9) | 20.1 | 25.0 |
| | 256 | 10 | 2 | 1 | 1 | 0 | 0 | 0 | 0 | 0 | 0 | 0 - - - 0 | 40 | | 20.4 | 26.3 |
| | 204.8 | 10 | 0 | 0 | 1 | 0 | 0 | 0 | 0 | 0 | 0 | 0 - - - 0 | 10 | | 19.9 | 26.6 |
| | 163.8 | 10 | 0 | 0 | 0 | 0 | 0 | 0 | 0 | 0 | 0 | 0 - - - 0 | 0 | | 20.0 | 26.9 |
| Female | 400 | 10 | 10 | 0 | 0 | 0 | 0 | 0 | 0 | 0 | 0 | 0 - - - 0 | 100 | 256 | 19.8 | — |
| | 320 | 10 | 5 | 2 | 1 | 0 | 0 | 0 | 0 | 0 | 0 | 0 - - - 0 | 80 | (221.7~295.5) | 20.6 | 24.5 |
| | 256 | 10 | 3 | 1 | 0 | 1 | 0 | 0 | 0 | 0 | 0 | 0 - - - 0 | 50 | | 19.9 | 24.2 |
| | 204.8 | 10 | 0 | 1 | 0 | 1 | 0 | 0 | 0 | 0 | 0 | 0 - - - 0 | 20 | | 20.5 | 24.3 |
| | 163.8 | 10 | 0 | 0 | 0 | 0 | 0 | 0 | 0 | 0 | 0 | 0 - - - 0 | 0 | | 19.9 | 24.5 |
| 50% Male, 50% Female | 400 | 20 | 20 | 0 | 0 | 0 | 0 | 0 | 0 | 0 | 0 | 0 - - - 0 | 100 | 258.53 | | |
| | 320 | 20 | 12 | 3 | 2 | 0 | 0 | 0 | 0 | 0 | 0 | 0 - - - 0 | 85 | (234.9~284.4) | | |
| | 256 | 20 | 5 | 2 | 1 | 1 | 0 | 0 | 0 | 0 | 0 | 0 - - - 0 | 45 | | | |
| | 204.8 | 20 | 0 | 1 | 1 | 1 | 0 | 0 | 0 | 0 | 0 | 0 - - - 0 | 15 | | | |
| | 163.8 | 20 | 0 | 0 | 0 | 0 | 0 | 0 | 0 | 0 | 0 | 0 - - - 0 | 0 | | | |

TABLE 32

Acute toxicity in the Kunming mice given a single intravenous injection dose of ACEA100108.

| Sex | Dosage Mg/kg | Animal number | \multicolumn{10}{c}{Distribution of dead animals on each day after the single intravenous injection} | Percentage of dead animals % | $LD_{50}$ (95% CL) g/kg | Average animal weight Beginning | End |
|---|---|---|---|---|---|---|---|---|---|---|---|---|---|---|---|---|
| | | | 1 | 2 | 3 | 4 | 5 | 6 | 7 | 8 | 9 | 10 - - - 14 | | | | |
| Male | 500 | 10 | 10 | 0 | 0 | 0 | 0 | 0 | 0 | 0 | 0 | 0 - - - 0 | 100 | 319.3 | 20.3 | — |
| | 400 | 10 | 3 | 3 | 0 | 1 | 0 | 0 | 0 | 0 | 0 | 0 - - - 0 | 70 | (271.9~375.0) | 19.9 | 26.0 |
| | 320 | 10 | 0 | 3 | 1 | 0 | 0 | 0 | 0 | 0 | 0 | 0 - - - 0 | 40 | | 20.0 | 26.7 |
| | 256 | 10 | 0 | 2 | 0 | 1 | 0 | 0 | 0 | 0 | 0 | 0 - - - 0 | 30 | | 20.2 | 26.3 |
| | 204.8 | 10 | 0 | 0 | 1 | 0 | 0 | 0 | 0 | 0 | 0 | 0 - - - 0 | 10 | | 20.3 | 26.3 |
| | 163.8 | 10 | 0 | 0 | 0 | 0 | 0 | 0 | 0 | 0 | 0 | 0 - - - 0 | 0 | | 20.4 | 27.0 |
| Female | 500 | 10 | 10 | 0 | 0 | 0 | 0 | 0 | 0 | 0 | 0 | 0 - - - 0 | 100 | 313.2 | 19.6 | — |
| | 400 | 10 | 5 | 2 | 0 | 1 | 0 | 0 | 0 | 0 | 0 | 0 - - - 0 | 80 | (272.7~359.7) | 19.9 | 23.5 |
| | 320 | 10 | 2 | 2 | 1 | 0 | 0 | 0 | 0 | 0 | 0 | 0 - - - 0 | 50 | | 19.9 | 24.6 |
| | 256 | 10 | 0 | 2 | 0 | 1 | 0 | 0 | 0 | 0 | 0 | 0 - - - 0 | 30 | | 20.1 | 24.6 |
| | 204.8 | 10 | 0 | 0 | 0 | 0 | 0 | 0 | 0 | 0 | 0 | 0 - - - 0 | 0 | | 20.5 | 24.3 |
| | 163.8 | 10 | 0 | 0 | 0 | 0 | 0 | 0 | 0 | 0 | 0 | 0 - - - 0 | 0 | | 19.6 | 24.2 |
| 50% male, 50% | 500 | 20 | 20 | 0 | 0 | 0 | 0 | 0 | 0 | 0 | 0 | 0 - - - 0 | 100 | 316 | | |
| | 400 | 20 | | 8 | 5 | 0 | 2 | 0 | 0 | 0 | 0 | 0 - - - 0 | 75 | (284.2~351.2) | | |
| | 320 | 20 | | 2 | 5 | 2 | 0 | 0 | 0 | 0 | 0 | 0 - - - 0 | 45 | | | |

TABLE 32-continued

Acute toxicity in the Kunming mice given a single intravenous injection dose of ACEA100108.

| Sex | Dosage Mg/kg | Animal number | Distribution of dead animals on each day after the single intravenous injection | | | | | | | | | | Percentage of dead animals % | LD$_{50}$ (95% CL) g/kg | Average animal weight | |
|---|---|---|---|---|---|---|---|---|---|---|---|---|---|---|---|---|
| | | | 1 | 2 | 3 | 4 | 5 | 6 | 7 | 8 | 9 | 10 - - - 14 | | | Beginning | End |
| female | 256 | 20 | 0 | 4 | 0 | 2 | 0 | 0 | 0 | 0 | 0 | 0 - - - 0 | 30 | | | |
| | 204.8 | 20 | 0 | 0 | 1 | 0 | 0 | 0 | 0 | 0 | 0 | 0 - - - 0 | 5 | | | |
| | 163.8 | 20 | 0 | 0 | 0 | 0 | 0 | 0 | 0 | 0 | 0 | 0 - - - 0 | 0 | | | |

EXAMPLE 7

Inhibition of Cell Proliferation by DBTS, Colcemid and Paclitaxel

H460 cells (human lung cancer cells) were seeded into wells of 16× or 96× microtiter plate devices (electronic plates, i.e., the plates comprise microelectrode sensor arrays in the wells of the plate) with an initial seeding density of 8000 cells per well and were pre-incubated in incubator under standard cell culture conditions for about 22 hrs. Dibenzyl trisulfide (DBTS), colcemil and paclitaxel at different concentrations in DMSO were added into wells following the incubation period. The cell status was monitored prior to and after the compound addition using RT-CES system. The cell indexes of different wells were between 1.7 and 1.9 for DBTS and colcemid solutions just before the compound addition, and between 1.4 and 1.9 for paclitaxel. FIGS. 1A-C show the normalized cell index as a function of time prior to and after the compound addition. The cell index was normalized against the cell index values at a time point just after compound addition (about 23 hrs after cell seeding).

EXAMPLE 8

Inhibition of Cell Proliferation by DBTS in MV522 Cells

Figure 2:
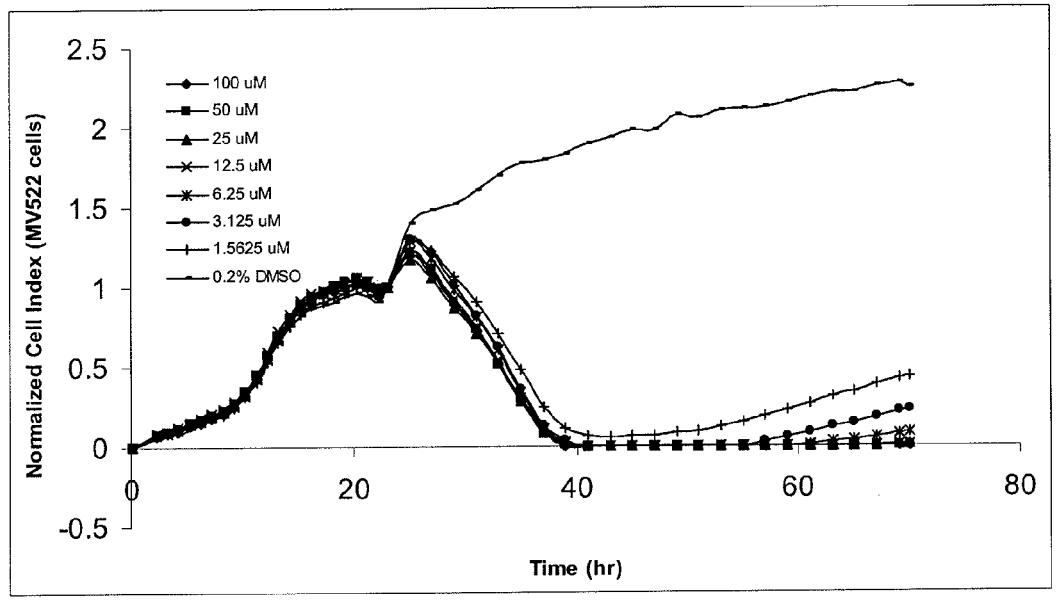
FIG. 2 shows the responses of MV522 cells (lung cancer cell line) to different concentrations of dibenzyl trisulfide (DBTS), as determined on RT-CES system.

MV522 cells (human lung cancer cells) were seeded into wells of 16× or 96× microtiter plate devices (electronic plates, i.e., the plates comprise microelectrode sensor arrays in the wells of the plate) with an initial seeding density of 10,000 cells per well and were pre-incubated in incubator under standard cell culture conditions for about 22 hrs. Dibenzyl trisulfide solutions in DMSO were added into wells following the incubation period. The cell status was monitored prior to and after the compound addition using RT-CES system. The cell indexes of different wells were between 1.0 and 1.6 just before the compound addition. FIG. 2 shows the normalized cell index as a function of time prior to and after the compound addition. The cell index was normalized against the cell index values at a time point just after compound addition (about 23 hrs after cell seeding).

EXAMPLE 9

Inhibition of Cell Proliferation by Dibenzyl Trisulfide in MCF-7 Cells

Figure 3:
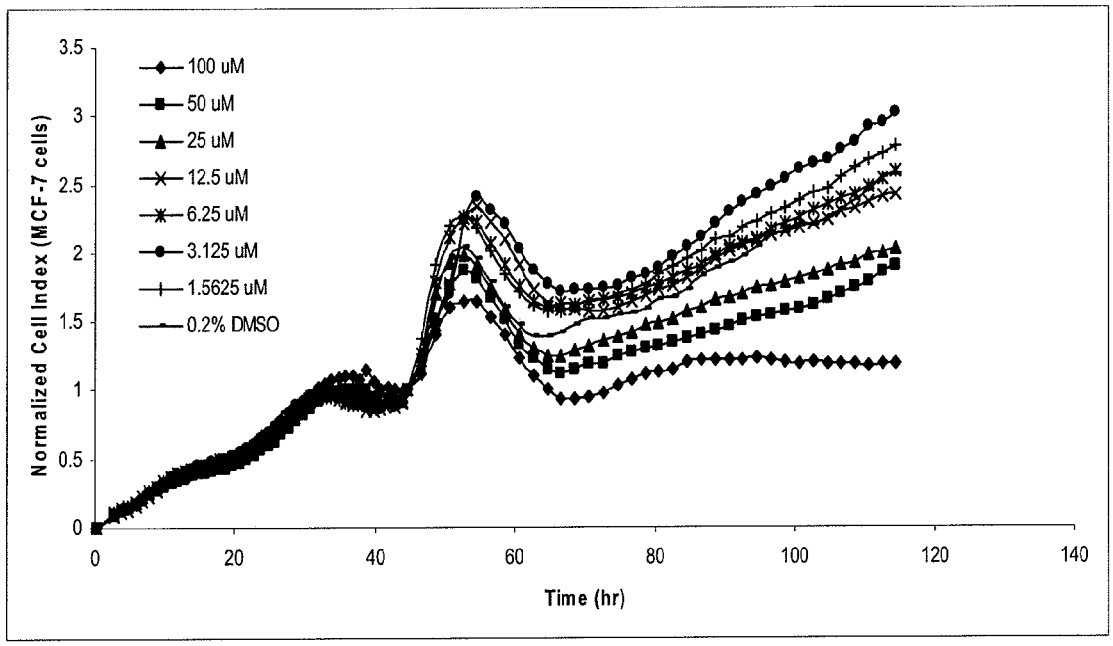
FIG. 3 shows responses of MCF-7 cells (breast cancer cell line) to different concentrations of dibenzyl trisulfide (DBTS), as determined on RT-CES system.

MCF-7 cells (human breast cancer cells) were seeded into wells of 16× or 96× microtiter plate devices (electronic plates, i.e., the plates comprise microelectrode sensor arrays in the wells of the plate) with an initial seeding density of 10,000 cells per well and were pre-incubated in incubator under standard cell culture conditions for about 44 hrs. Dibenzyl trisulfide solution in DMSO was added into wells following the incubation period. The cell status was monitored prior to and after the compound addition using RT-CES system. The cell indexes of different wells were between 1.2 and 1.5 just before the compound addition. FIG. 3 shows the normalized cell index as a function of time prior to and after the compound addition. The cell index was normalized against the cell index values at a time point just after compound addition (about 44.5 hrs after cell seeding).

EXAMPLE 10

Inhibition of Cell Proliferation by Dibenzyl Trisulfide in A549 Cells

Figure 4:
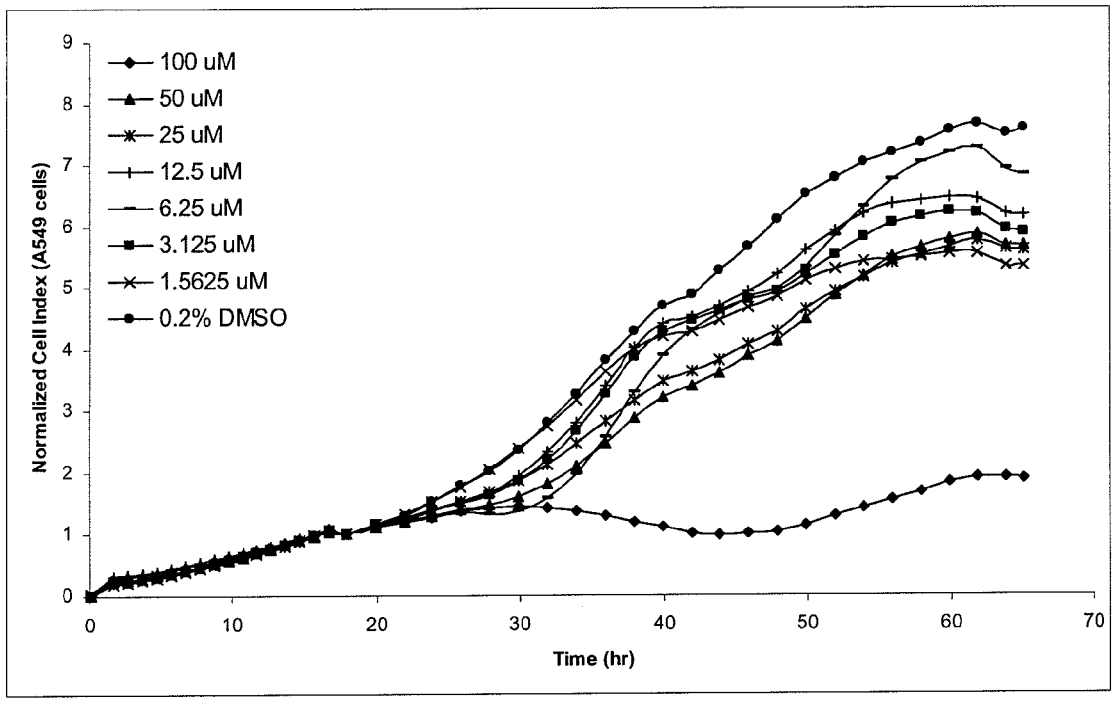
FIG. 4 shows responses of A549 cells (lung cancer cell line) to different concentrations of dibenzyl trisulfide (DBTS), as determined on RT-CES system.

A549 cells (human lung cancer cells) were seeded into wells of 16× or 96× microtiter plate devices (electronic plates, i.e., the plates comprise microelectrode sensor arrays in the wells of the plate) with an initial seeding density of 8,000 cells per well and were pre-incubated in incubator under standard cell culture conditions for about 17 hrs. Dibenzyl trisulfide solution in DMSO was added into wells following the incubation period. The cell status was monitored prior to and after the compound addition using RT-CES system. The cell indexes of different wells were between 0.72 and 1.26 just before the compound addition. FIG. 4 shows the normalized cell index as a function of time prior to and after the compound addition. The cell index was normalized against the cell index values at a time point just after compound addition (about 18 hrs after cell seeding).

EXAMPLE 11

Inhibition of Cell Proliferation by Dibenzyl Trisulfide in PC3 Cells

PC3 cells (human prostate cancer cells) were seeded into wells of 16× or 96× microtiter plate devices (electronic plates, i.e., the plates comprise microelectrode sensor arrays in the wells of the plate) with an initial seeding density of 10,000 cells per well and were pre-incubated in incubator under standard cell culture conditions for about 22.5 hrs. Dibenzyl trisulfide solution in DMSO was added into wells following the incubation period. The cell status was monitored prior to and after the compound addition using RT-CES system. The cell indexes of different wells were between 0.34 and 0.54 just before the compound addition. FIG. 5 shows the normalized cell index as a function of time prior to and after the compound addition. The cell index was normalized against the cell index values at a time point just after compound addition (about 23.5 hrs after cell seeding).

EXAMPLE 12

Inhibition of Cell Proliferation by DBTS and 5-Fluorouracil in A431 Cells

A431 cells (human epidermoid cancer cells) were seeded into wells of microtiter plate devices (electronic plates, i.e., the plates comprise microelectrode sensor arrays in the wells of the plate) with an initial seeding density of 10,000 cells per well and were pre-incubated in incubator under standard cell culture conditions for about 22.3 hrs. Various concentrations of DBTS and 5-fluorouracil solutions were added into wells following the incubation period. The cell status was monitored prior to and after the compound addition using RT-CES system. The cell indexes of different wells of DBTS were between 0.6 and 1.2 for DBTS, and between 0.6 and 1.2 for 5-fluorouracil just before the compound addition. FIGS. 6A-B show the normalized cell index as a function of time prior to and after the compound addition. The cell index was normalized against the cell index values at a time point just after compound addition (22.6 hrs after cell seeding).

EXAMPLE 13

Inhibition of Cell Proliferation by DBTS in HT1080 Cells

Figure 7:
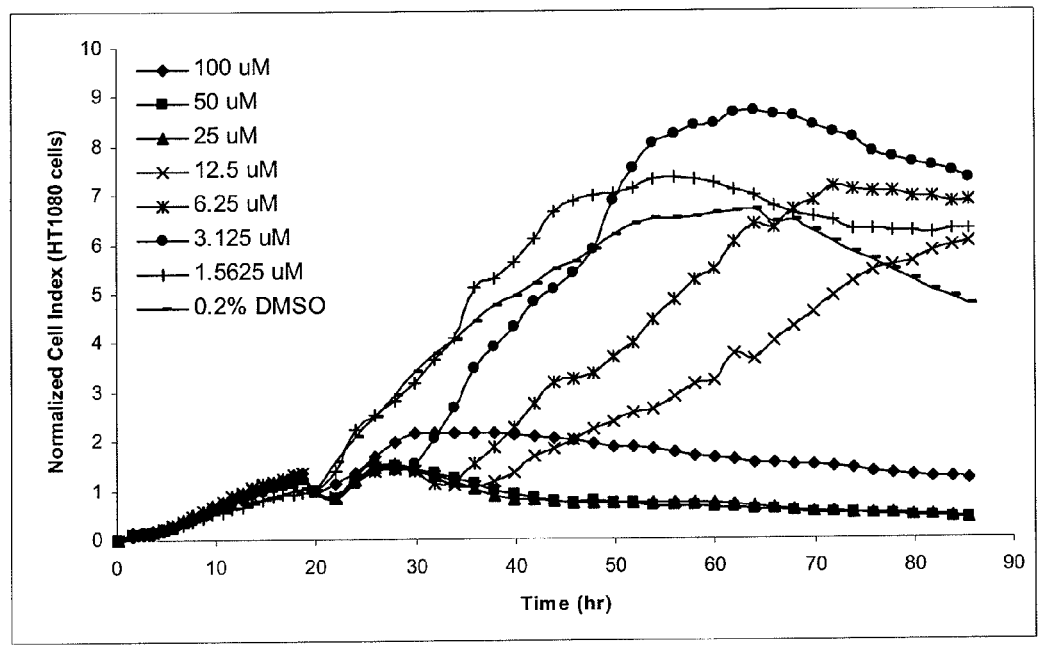
FIG. 7 shows responses of HT1080 cells (fibrosarcoma cell line) to different concentrations of dibenzyl trisulfide (DBTS), as determined on RT-CES system.

HT1080 cells (human fibrosarcoma cells) were seeded into wells of 16× or 96× microtiter plate devices (electronic plates, i.e., the plates comprise microelectrode sensor arrays in the wells of the plate) with an initial seeding density of 4,000 cells per well and were pre-incubated in incubator under standard cell culture conditions for about 18.6 hrs. Dibenzyl trisulfide solution in DMSO was added into wells following the incubation period. The cell status was monitored prior to and after the compound addition using RT-CES system. The cell indexes of different wells were between 0.72 and 1.45 just before the compound addition. FIG. 7 shows the normalized cell index as a function of time prior to and after the compound addition. The cell index was normalized against the cell index values at a time point just after compound addition (about 20 hrs after cell seeding).

EXAMPLE 14

Inhibition of Cell Proliferation by DBTS in MDA-231 Cells

Figure 8:
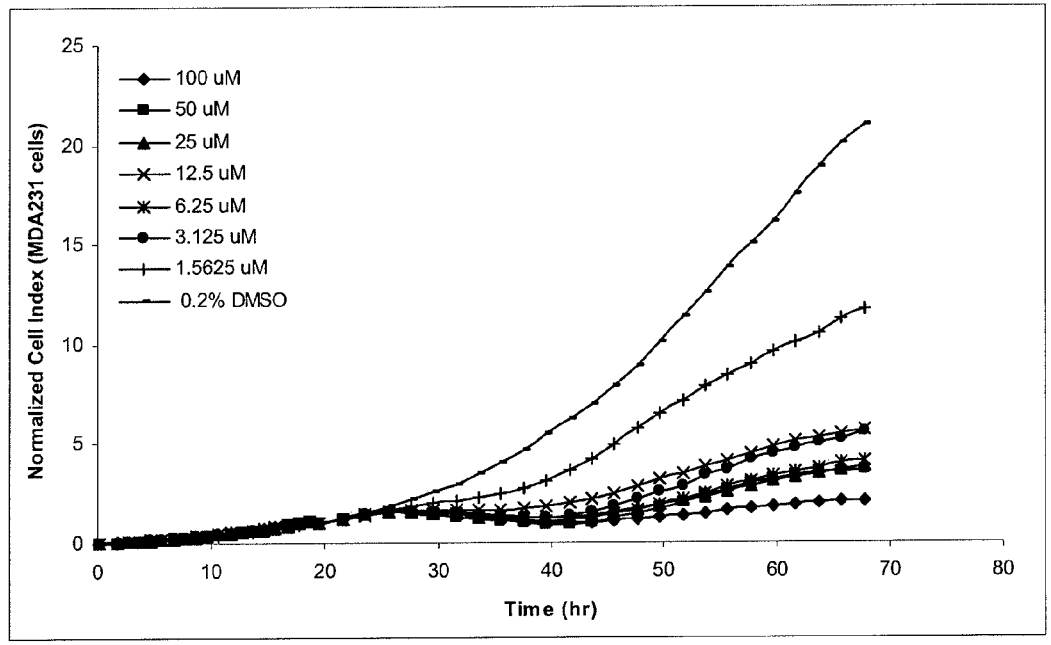
FIG. 8 shows responses of MDA-231 cells (breast cancer cell line) to different concentrations of dibenzyl trisulfide (DBTS), as determined on RT-CES system.

MDA-231 cells (human breast cancer cells) were seeded into wells of 16× or 96× microtiter plate devices (electronic plates, i.e., the plates comprise microelectrode sensor arrays in the wells of the plate) with an initial seeding density of 5,000 cells per well and were pre-incubated in incubator under standard cell culture conditions for about 18.7 hrs. Dibenzyl trisulfide solution in DMSO was added into wells following the incubation period. The cell status was monitored prior to and after the compound addition using RT-CES system. The cell indexes of different wells were between 0.65 and 0.82 just before the compound addition. FIG. 8 shows the normalized cell index as a function of time prior to and after the compound addition. The cell index was normalized against the cell index values at a time point just after compound addition (about 19.6 hrs after cell seeding).

EXAMPLE 15

Inhibition of Cell Proliferation by DBTS in HT-29 Cells

Figure 9:
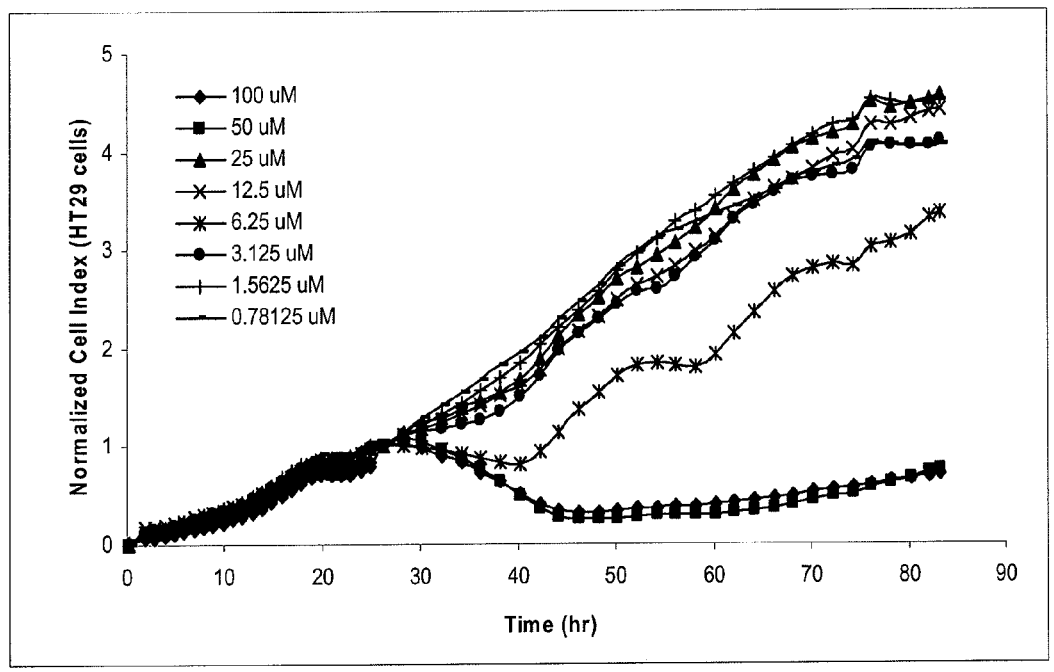
FIG. 9 shows responses of HT-29 cells (colon cancer cell line) to different concentrations of dibenzyl trisulfide (DBTS), as determined on RT-CES system.

HT-29 cells (human colon cancer cells) were seeded into wells of 16× or 96× microtiter plate devices (electronic plates, i.e., the plates comprise microelectrode sensor arrays in the wells of the plate) with an initial seeding density of 10,000 cells per well and were pre-incubated in incubator under standard cell culture conditions for about 25 hrs. Dibenzyl trisulfide solution in DMSO was added into wells following the incubation period. The cell status was monitored prior to and after the compound addition using RT-CES system. The cell indexes of different wells were between 0.95 and 1.13 just before the compound addition. FIG. 9 shows the normalized cell index as a function of time prior to and after the compound addition (about 26 hrs after cell seeding). The cell index was normalized against the cell index values at a time point just prior to compound addition.

EXAMPLE 16

Inhibition of Cell Proliferation by DBTS in HC-2998 Cells

Figure 10:
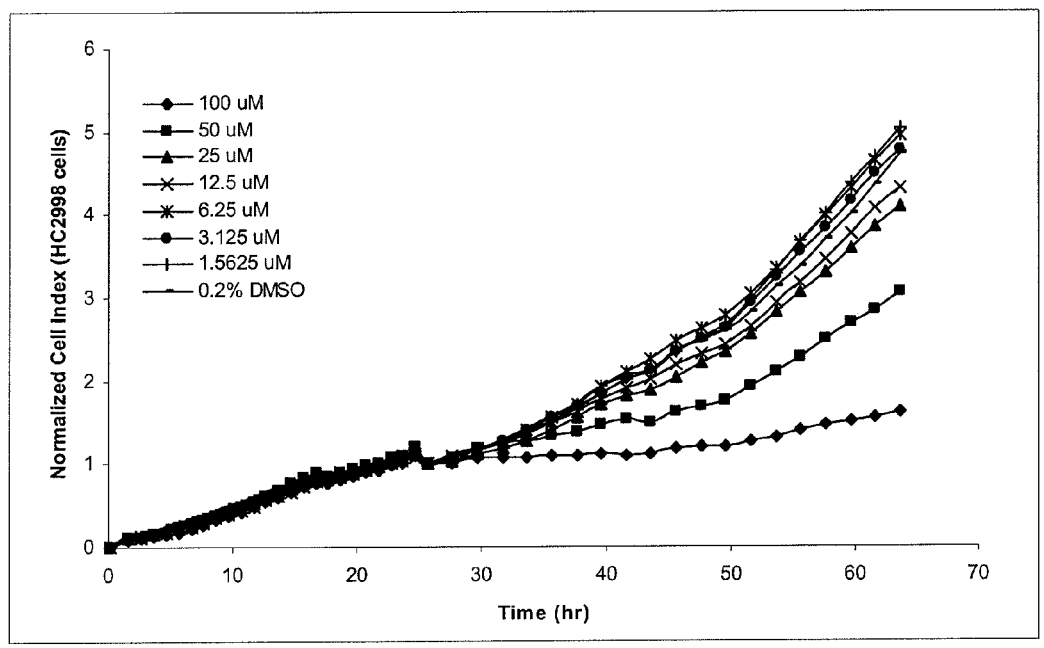
FIG. 10 shows responses of HC-2998 cells (colon cancer cell line) to different concentrations of dibenzyl trisulfide (DBTS), as determined on RT-CES system.

HC-2998 cells (human colon cancer cells) were seeded into wells of 16× or 96× microtiter plate devices (electronic plates, i.e., the plates comprise microelectrode sensor arrays in the wells of the plate) with an initial seeding density of 10,000 cells per well and were pre-incubated in incubator under standard cell culture conditions for about 24.7 hrs. Dibenzyl trisulfide solution in DMSO was added into wells following the incubation period. The cell status was monitored prior to and after the compound addition using RT-CES system. The cell indexes of different wells were between 0.33 and 0.68 just before the compound addition. FIG. 10 shows the normalized cell index as a function of time prior to and after the compound addition. The cell index was normalized against the cell index values at a time point just after compound addition (about 25.7 hrs after cell seeding).

EXAMPLE 17

Inhibition of Cell Proliferation by DBTS in OVCAR4 Cells

Figure 11:
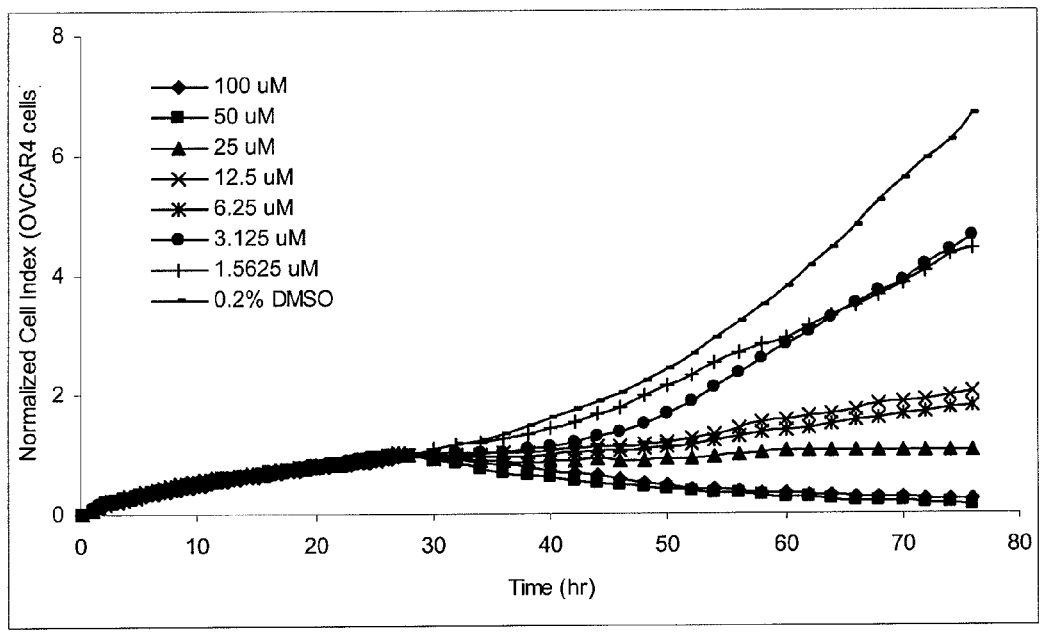
FIG. 11 shows responses of OVCAR4 cells (ovarian cancer cell line) to different concentrations of dibenzyl trisulfide (DBTS), as determined on RT-CES system.

OVCAR4 cells (human ovarian cancer cells) were seeded into wells of 16× or 96× microtiter plate devices (electronic plates, i.e., the plates comprise microelectrode sensor arrays in the wells of the plate) with an initial seeding density of 10,000 cells per well and were pre-incubated in incubator under standard cell culture conditions for about 27 hrs. Dibenzyl trisulfide solution in DMSO was added into wells following the incubation period. The cell status was monitored prior to and after the compound addition using RT-CES system. The cell indexes of different wells were between 1.4 and 1.7 just before the compound addition. FIG. 11 shows the normalized cell index as a function of time prior to and after the compound addition. The cell index was normalized against the cell index values at a time point just after compound addition (about 28 hrs after cell seeding).

EXAMPLE 18

Inhibition of Cell Proliferation by DBTS in A2780 Cells

Figure 12:
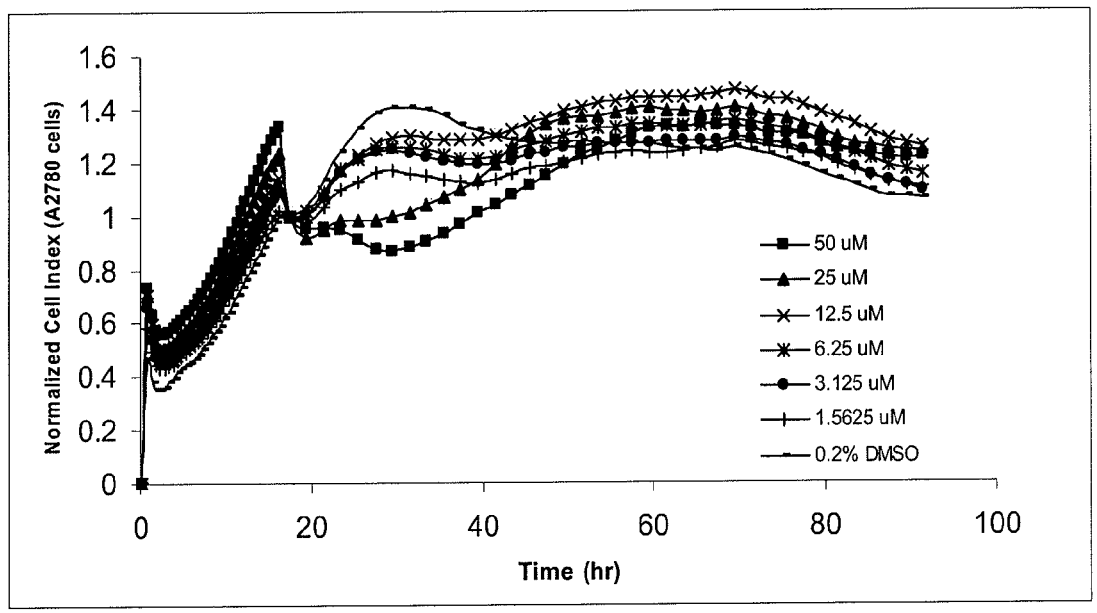
FIG. 12 shows responses of A2780 cells (colon cancer line) to different concentrations of dibenzyl trisulfide (DBTS), as determined on RT-CES system.

A2780 cells (human colon cancer cells) were seeded into wells of 16× or 96× microtiter plate devices (electronic plates, i.e., the plates comprise microelectrode sensor arrays in the wells of the plate) with an initial seeding density of 20,000 cells per well and were pre-incubated in incubator under standard cell culture conditions for about 16.4 hrs. Dibenzyl trisulfide solution in DMSO was added into wells following the incubation period. The cell status was monitored prior to and after the compound addition using RT-CES system. The cell indexes of different wells were between 2.2 and 3.7 just before the compound addition. FIG. 12 shows the normalized cell index as a function of time prior to and after the compound addition. The cell index was normalized against the cell index values at a time point just after compound addition (about 17.5 hrs after cell seeding).

EXAMPLE 19

Response of HepG2 Cells to DBTS

HepG2 cells (human hepatosarcoma cells) were seeded into wells of 16× or 96× microtiter plate devices (electronic plates, i.e., the plates comprise microelectrode sensor arrays in the wells of the plate) with an initial seeding density of 15,000 cells per well and were pre-incubated in incubator under standard cell culture conditions for about 22 hrs. Dibenzyl trisulfide solution in DMSO was added into wells following the incubation period. The cell status was monitored prior to and after the compound addition using RT-CES system. The cell index was between 0.7 and 0.97 just before the compound addition. FIG. 13 shows the normalized cell index as a function of time prior to and after the compound addition. The cell index was normalized against the cell index values at a time point just after compound addition (about 22.7 hrs after cell seeding). From the cell index data shown here, it appears that dibenzyl trisulfide exhibits no inhibition effect on HepG2 cell proliferation and no cytotoxic effect on the HepG2 cells within the exposing dose range.

EXAMPLE 20

Inhibition of Cancer Cell Proliferation by DBTS and Its Derivatives

The anticancer potency of DBTS and its derivatives were tested in 8 different types of human cancer cell lines using the RT-CES system and MTT assay. The 8 cancer cell lines were HT1080 (the human fibrosarcoma cell line), H460 (human non small cell lung cancer cell line), OVCAR4 (the human ovarian cancer cell line), MCF7 (human breast cancer cell line) MDA-MB231 (M231, the human breast cancer cell line) A2780 (the human colon cancer cell line) Jurkat (the human T cell leukemia cell line). The test DBTS derivatives include ACEA100107, ACEA100108, ACEA100109, ACEA100111, ACEA100115, ACEA100116, ACEA100117, ACEA100118, ACEA100119, and ACEA100120. ACEA100129 was also tested in HT1080, HELA and MCF7 cells, having an $IC_{50}$ value of 0.82 µM, 0.42 µM and 2.3 µM, respectively. The chemical structures of the derivatives are shown in Tables 33 and 34.

For the assay performed on the RT-CES system, the cells were seeded into the 16× or 96× microtiter plate devices (electronic plates, i.e., the plates comprise microelectrode sensor arrays in the wells of the plate) at the seeding density ranging from 5000 cells/well to 15,000 cells/well. The cells were incubated at 5% $CO_2$ and 37° C. for overnight till the cell indices reached the growth phase where the cell index was between 0.8 and 1.2. Serially diluted compounds were then added to the cells followed by dynamic monitoring of the effect of the compounds on the cell proliferation and cytotoxicity. The time-dependent $IC_{50}$ values for each derivative were calculated based the dose responses of cell index value at different time points after compound treatment. The $IC_{50}$ values shown in Table 35 corresponds to the time points at which compound showed the maximum inhibition after the treatment.

For the MTT assay, the cells were seeded into the regular 96× well plates at the cell seeding density ranging from 5000 cells/well to 15,000 cells/well. The cells were incubated at 5% $CO_2$ and 37° C. for overnight. The derivatives were serially diluted and added to the cells. The treatment was terminated after 48 hours of incubation by adding MTT staining reagent. After 4 hours, the staining was stopped by the stop buffer and then the calorimetric measurement was carried out on a microtiter plate reader at dual wave length, 650 nm and 550 nm. The $IC_{50}$ values for tested derivatives were calculated using the calorimetric readouts and listed in Table 36.

TABLE 33

| DBTS Derivative | R |
|---|---|
| DBTS (ACEA100101) | H |
| ACEA100108 | p-F |
| ACEA100118 | p-Cl |
| ACEA100115 | o-Cl |
| ACEA100116 | m-Me |
| ACEA100117 | m-CF$_3$ |
| ACEA100129 | p-Me |

TABLE 34

| DBTS Derivative Name | Ar |
|---|---|
| ACEA100111 | thiophene-ethyl |
| ACEA100107 | benzothiophene-ethyl |
| ACEA100109 | phenyl-ethyl |
| ACEA100120 | pyridin-4-yl-ethyl |
| ACEA100119 | pyrazin-2-yl-ethyl |

TABLE 35

$IC_{50}$ values (uM) of DBTS and its derivatives in 7 cancer cell lines using the RT-CES system.

| Cell line | ACEA100107 | ACEA100108 | ACEA100109 | ACEA100111 | ACEA100115 |
|---|---|---|---|---|---|
| HT1080 | 5.3 | 1.3 | 9.4 | 3.6 | 2.2 |
| OVCAR4 | 5.1 | 2 | 10.5 | 12.2 | 0.5 |
| M231 | 4.8 | 3.05 | 19.1 | 17.5 | 1.06 |
| A2780 | 2.65 | 0.5 | 6.25 | 1.3 | 0.75 |
| H460 | 20 | 9.2 | 42.2 | 33.5 | 23.2 |
| MCF7 | 5.6 | 2.15 | 8.8 | 6.25 | 7.8 |
| HepG2 | >50 | >50 | >50 | >50 | >50 |

| Cell line | ACEA100116 | ACEA100117 | ACEA100118 | AECA100119 | ACEA100120 | DBTS |
|---|---|---|---|---|---|---|
| HT1080 | 1.9 | 27.5 | 1.2 | 36 | 9 | 2.2 |
| OVCAR4 | 0.6 | 33.5 | 2.25 | 34.8 | 11.5 | 1.75 |
| M231 | 1.06 | 41 | 2.3 | >50 | 16 | 2.4 |
| A2780 | 0.75 | 11.8 | 0.7 | 17.4 | 4.4 | 0.4 |
| H460 | 12.5 | >50 | 9.6 | 31.5 | 18.2 | 11.1 |
| MCF7 | 2.75 | 48.8 | 4.4 | 31.6 | 11.9 | 6.6 |
| HepG2 | >50 | >50 | >50 | >50 | >50 | >50 |

TABLE 36

$IC_{50}$ values (uM) of DBTS and its derivatives in 8 cell lines using the MTT assay.

| | ACEA100107 | ACEA100108 | ACEA100109 | ACEA100111 | ACEA100115 |
|---|---|---|---|---|---|
| Jurkat | 1.2 | 0.35 | 4.7 | 2.6 | 0.51 |
| M231 | 6.6 | 4.4 | >50 | 1.6 | 3.1 |
| HT1080 | 5.3 | 19 | 20.8 | 34 | 12.4 |
| A2780 | 1.05 | 4.7 | 6.3 | 5.35 | 1.5 |
| MCF-7 | >50 | >50 | >50 | >50 | >50 |
| OVCAR4 | >50 | >50 | >50 | >50 | >50 |
| H460 | 27 | 10.25 | 27.4 | 12.5 | 11.75 |
| HepG2 | >50 | >50 | >50 | >50 | >50 |

| | ACEA100116 | ACEA100117 | ACEA100118 | ACEA100119 | ACEA100120 | ACEA100101 |
|---|---|---|---|---|---|---|
| Jurkat | 0.3 | 8 | 0.5 | >25 | 7.3 | 0.35 |
| M231 | 0.65 | 14.9 | 1.2 | >50 | 9.7 | 2.4 |
| HT1080 | 2.2 | 47.5 | 1.15 | 39.3 | 9 | 2.55 |
| A2780 | 0.8 | 11.7 | 0.8 | >50 | 15.2 | 1.2 |
| MCF-7 | >50 | >50 | >50 | >50 | >50 | >50 |
| OVCAR4 | >50 | >50 | >50 | >50 | >50 | >50 |
| H460 | 5.4 | >50 | 7.95 | >50 | 20.8 | 14.2 |
| HepG2 | >50 | >50 | >50 | >50 | >50 | >50 |

EXAMPLE 21

Kinetic Inhibition of Cancer Cell Proliferation by ACEA100108

Figure 26:
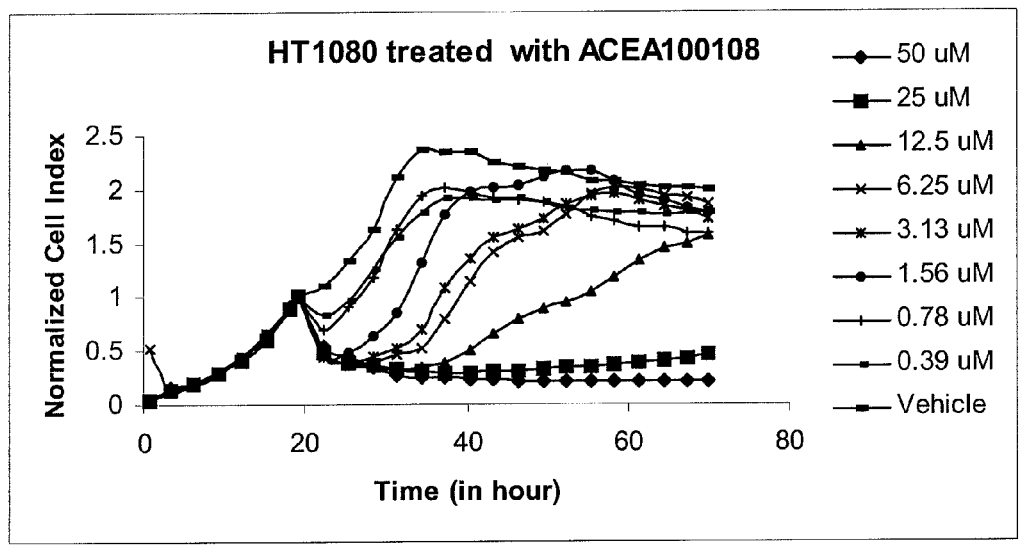
FIG. 26 shows the responses of various cell lines to ACEA100108, as determined on RT-CES system.
Figure 1:
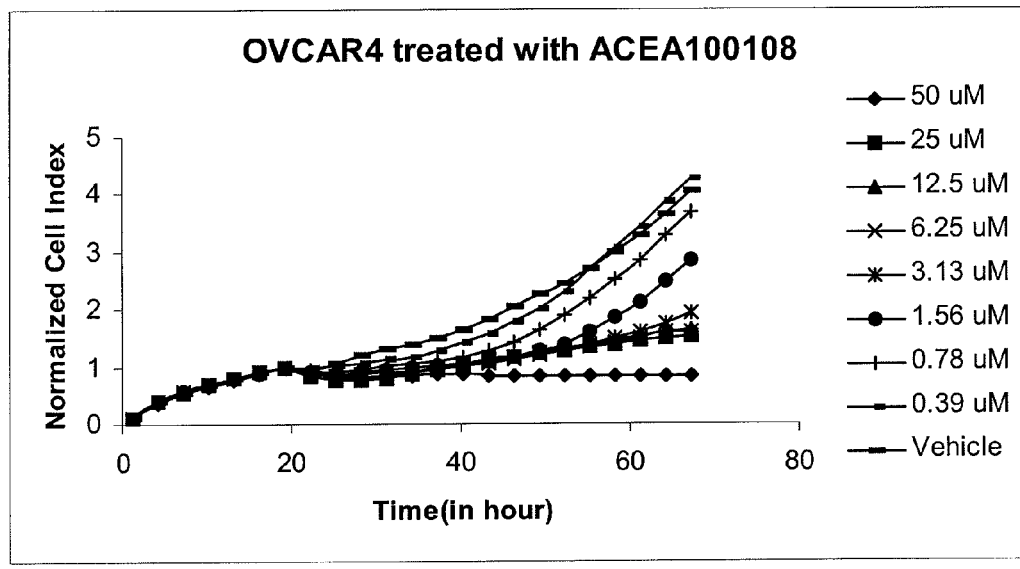
Figure 26:
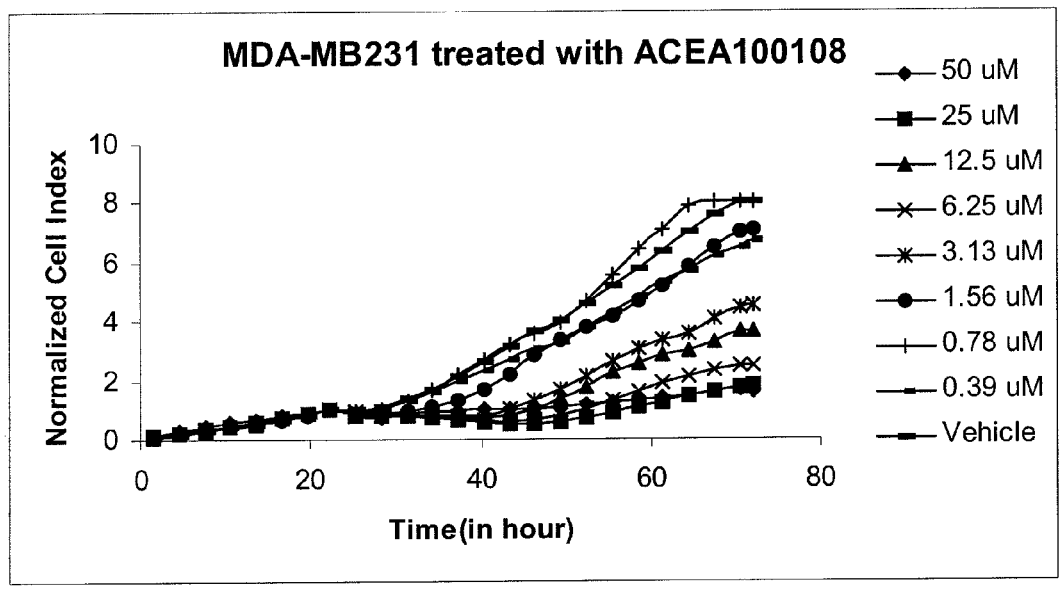
Figure 2:
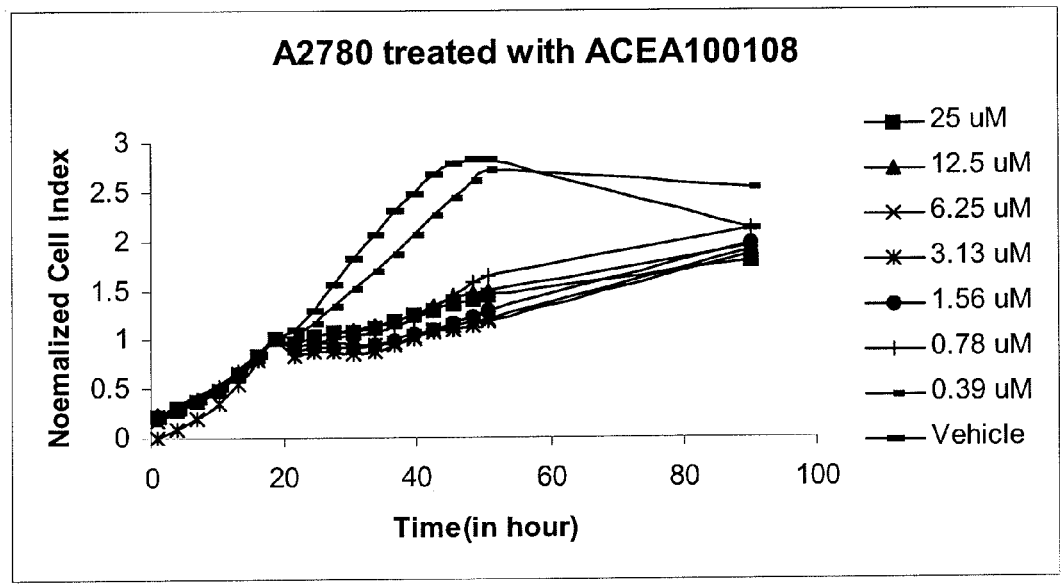
Figure 26:
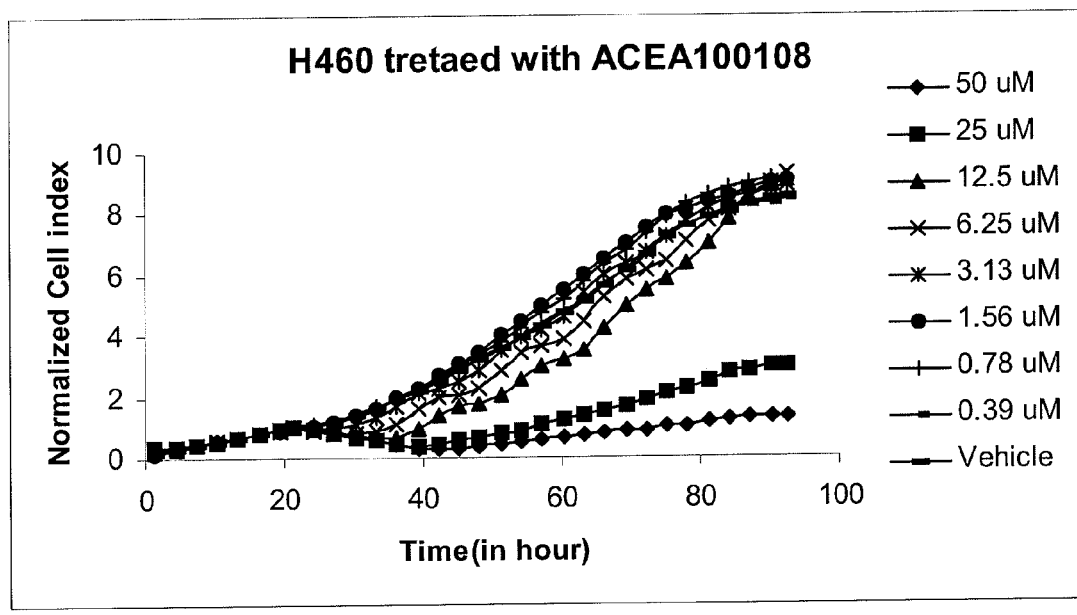
Figure 3:
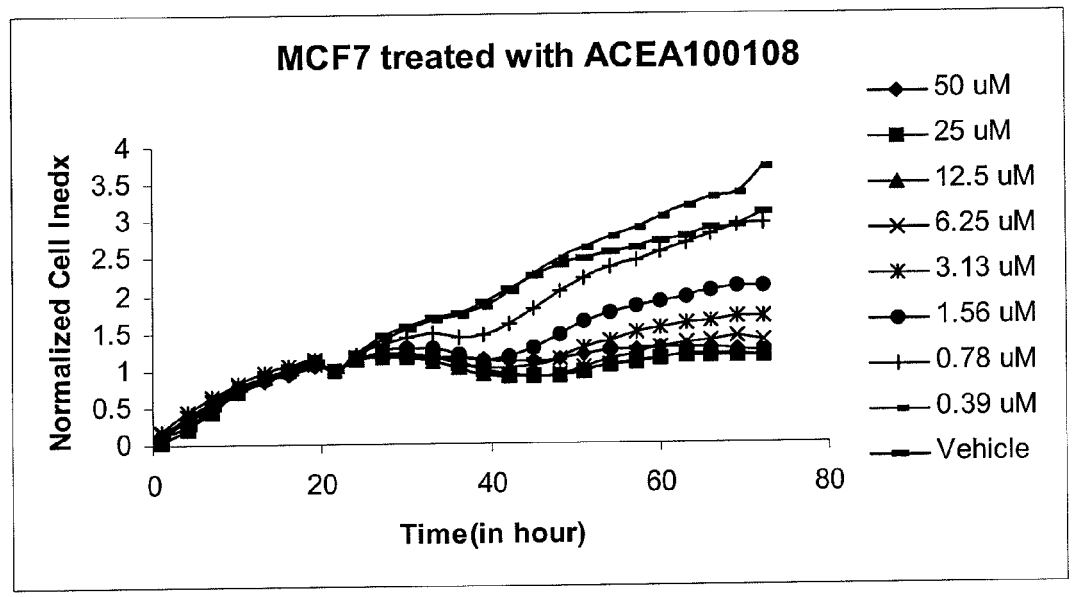
Figures 4, 26:
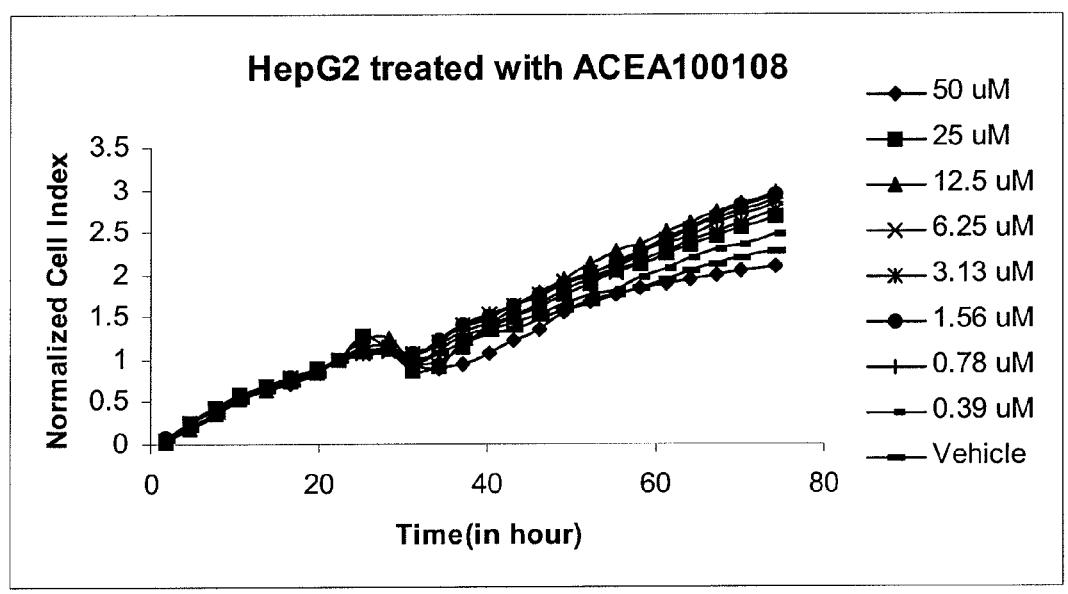

The anticancer potency of a DBTS derivative, ACEA100108 was tested in 7 cancer cell lines on the RT-CEA system. The cell lines were HT1080, H460, OVCAR4, MCF7, MDA-MB231, HepG2, and A2780. The cancer cells were seeded into 16x or 96x microtiter plate devices (i.e. electronic plates) containing wells at cell seeding density ranging from 5000 cells/well to 15000 cells/well, and the seeded cells were then incubated at 37° C., 5% $CO_2$. The cancer cell growth was monitored in real time on the RT-CES system till the cells reached the growth phase, which takes approximately 20 hours. Cells were then treated with ACEA100108 which were serially diluted at the concentrations ranging from 50 uM to 0.38 uM. The inhibition of the cancer proliferation of ACEA100108 and cytotoxicity responses of various cell lines to ACEA100108 were monitored on the RT-CES system in real time. The kinetic curves of the cell-compound interaction was then recorded and shown in the FIG. 26. The cell index curves were normalized against the cell index values at a time point just after compound addition (approximately 18-24 hrs after cell seeding).

EXAMPLE 22

Kinetic Inhibition of Cancer Cell Proliferation by the DBTS Derivatives

Figure 27:
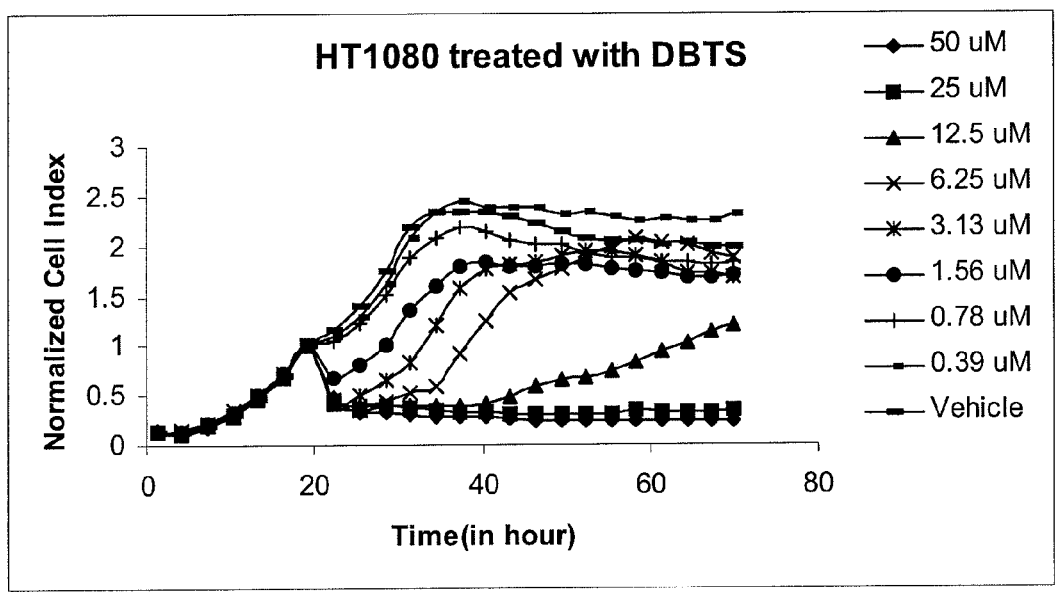
FIG. 27 shows the responses of HT1080 cell to different derivatives of DBTS, as determined on RT-CES system.
Figure 1:
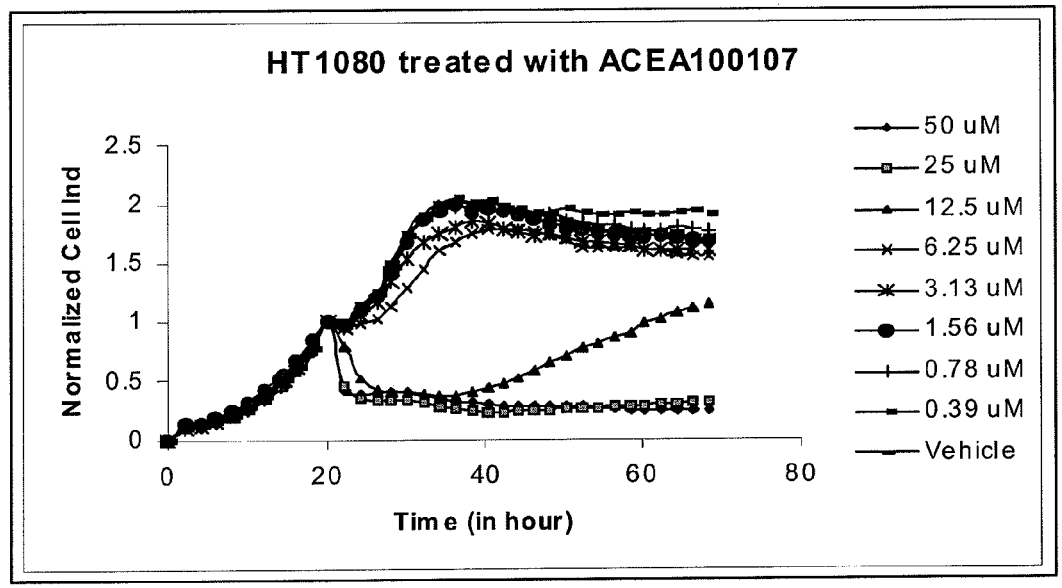
Figure 27:
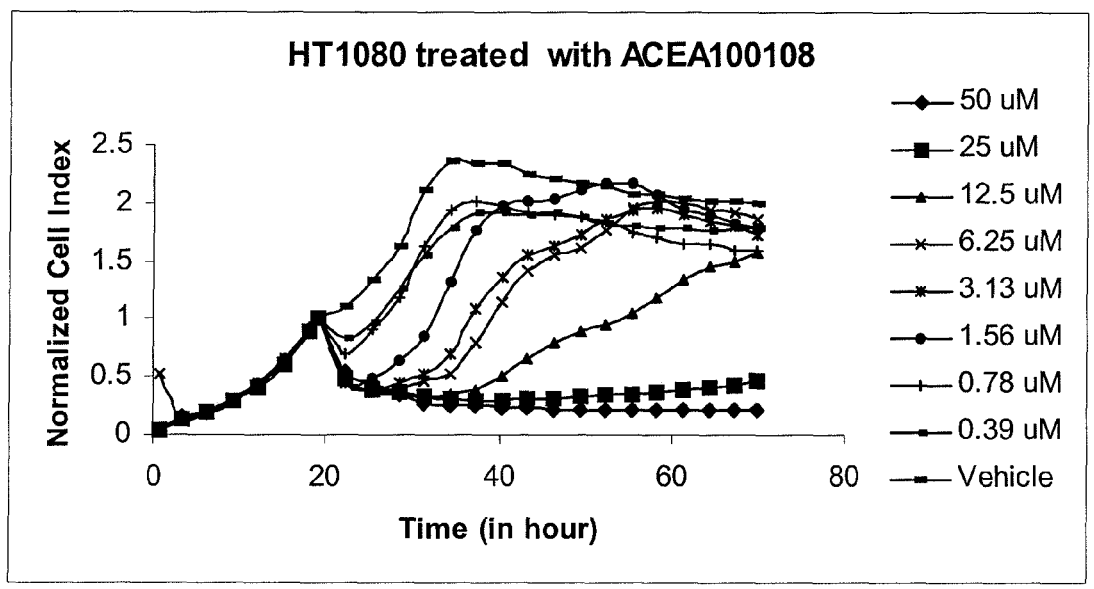
Figure 2:
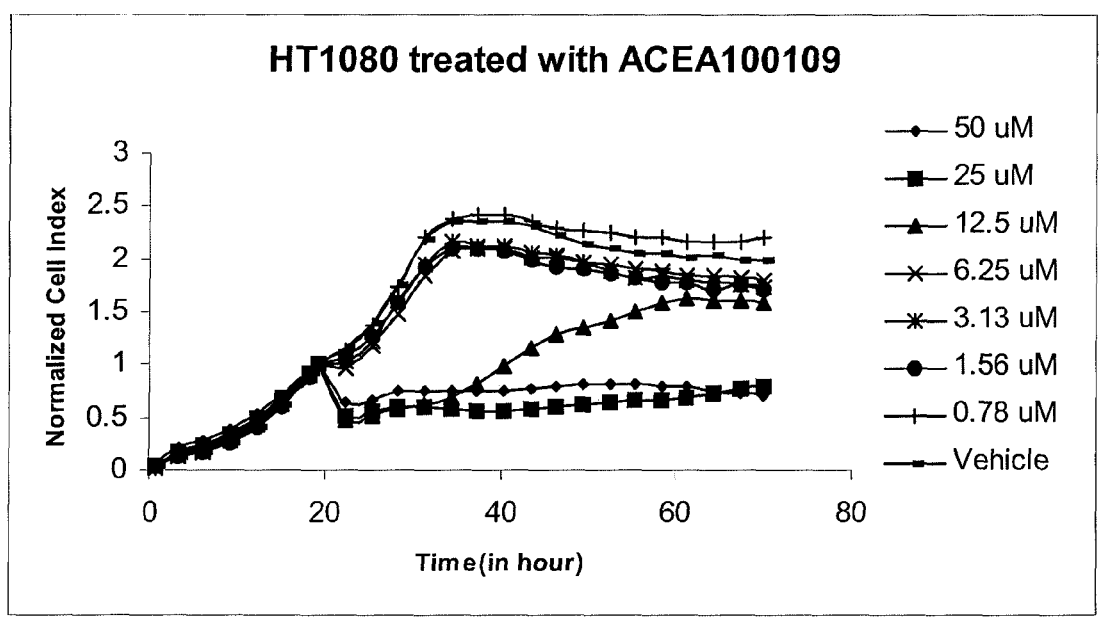
Figure 27:
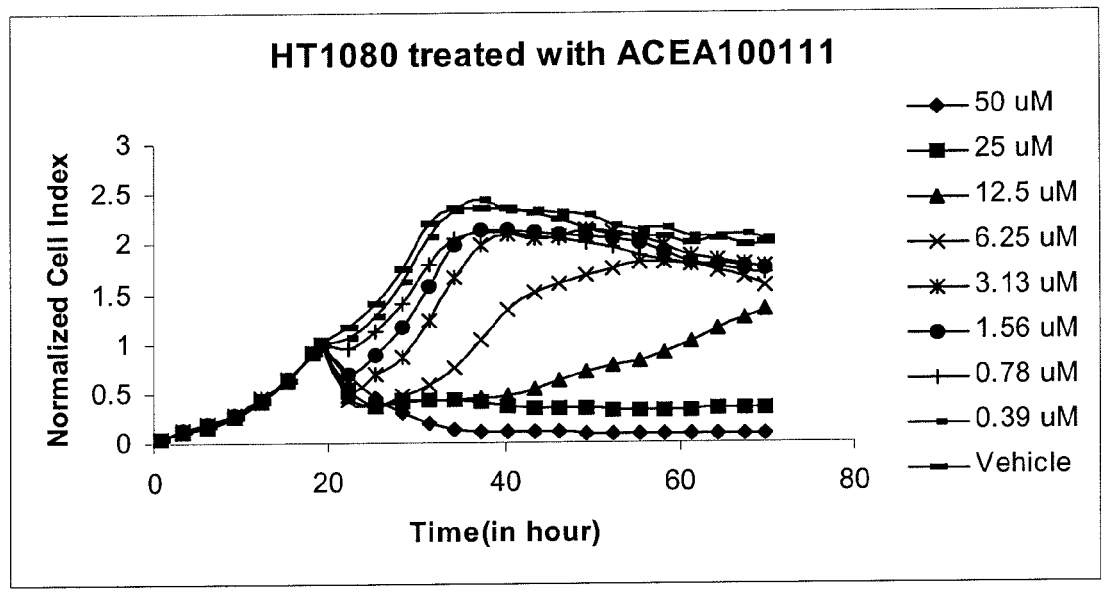
Figure 3:
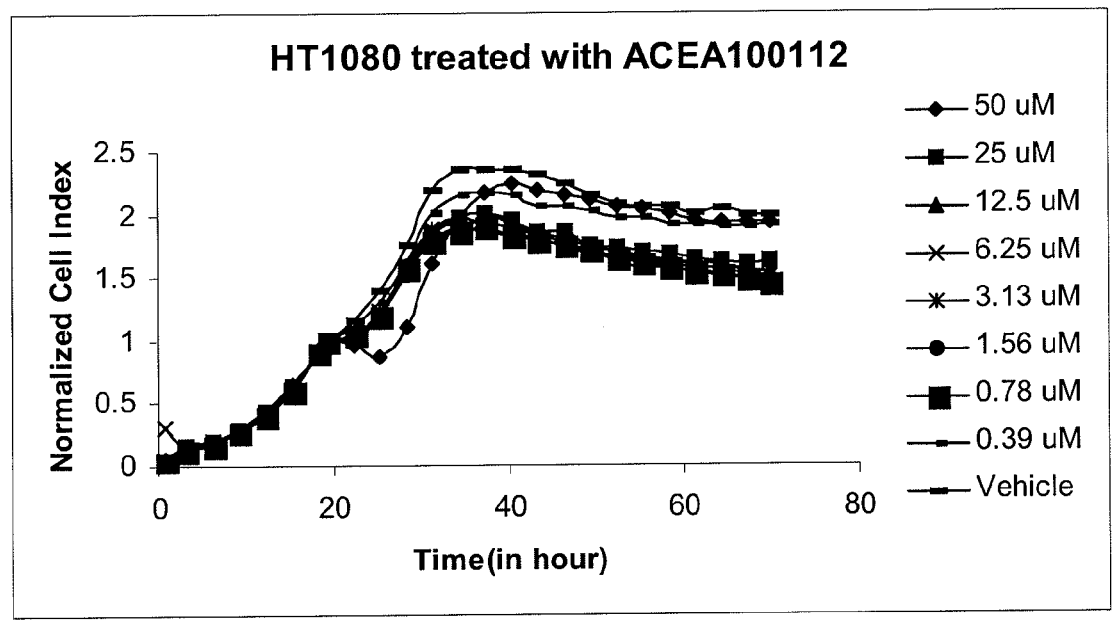
Figure 27:
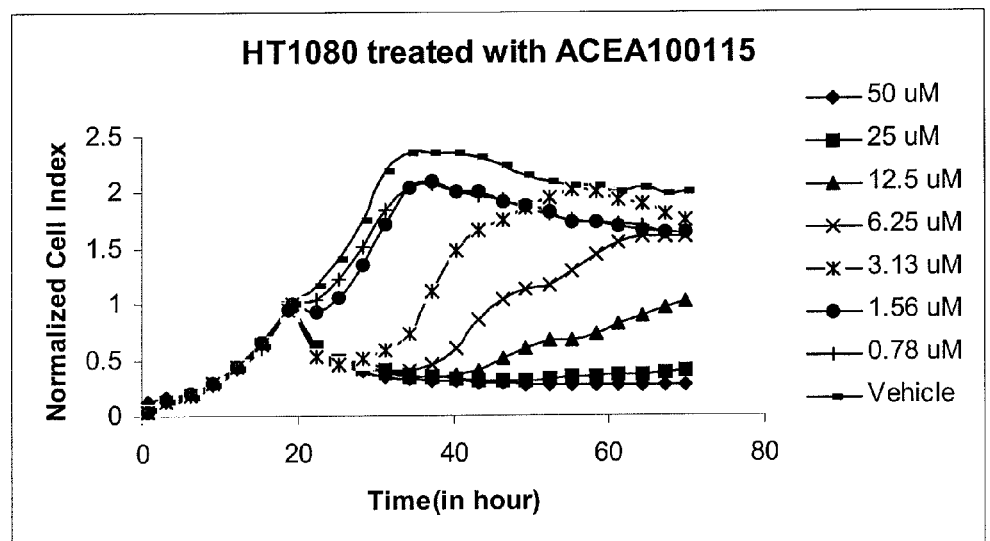
Figure 4:
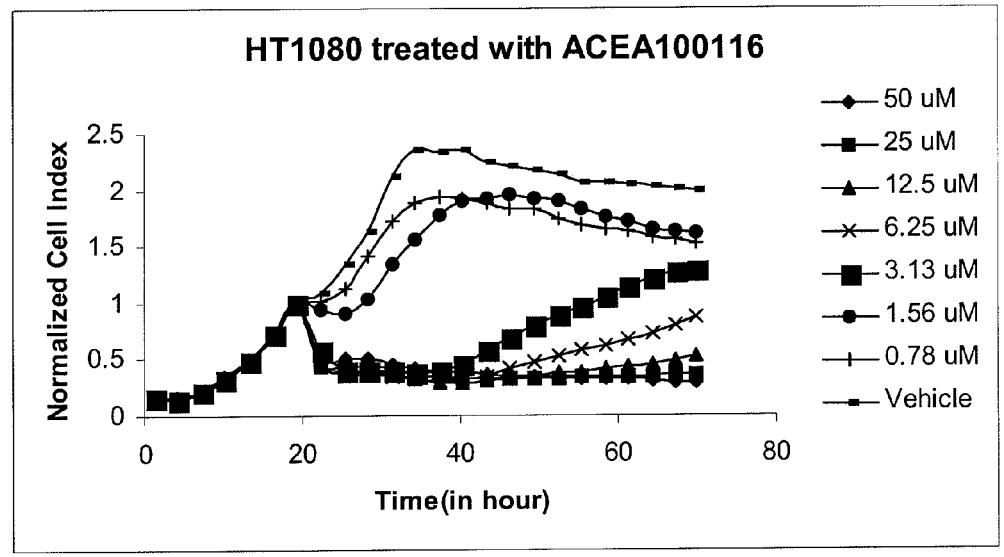
Figure 27:
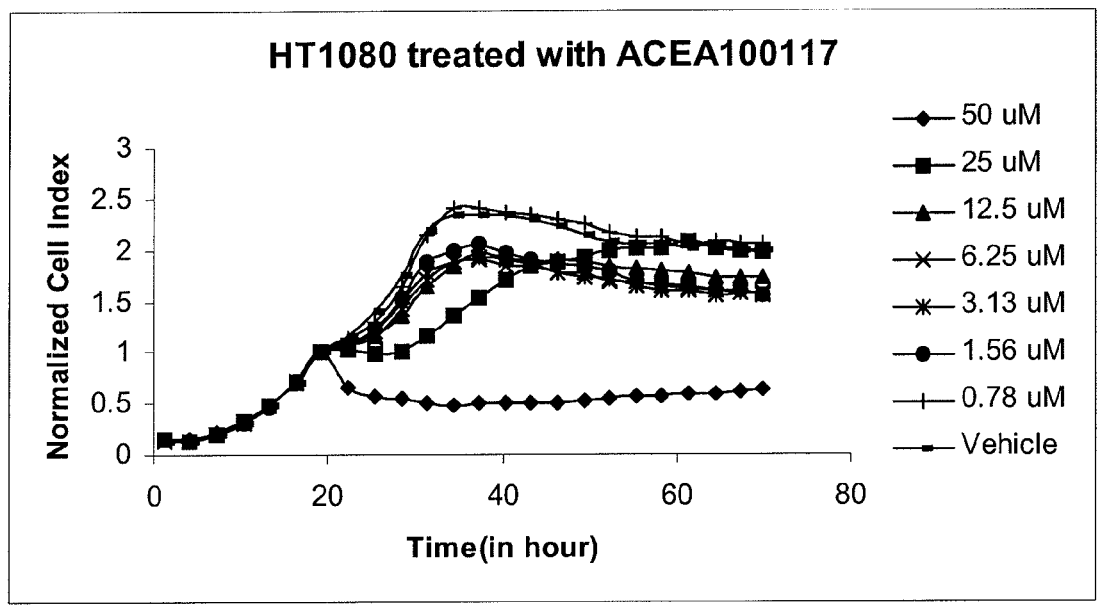
Figure 5:
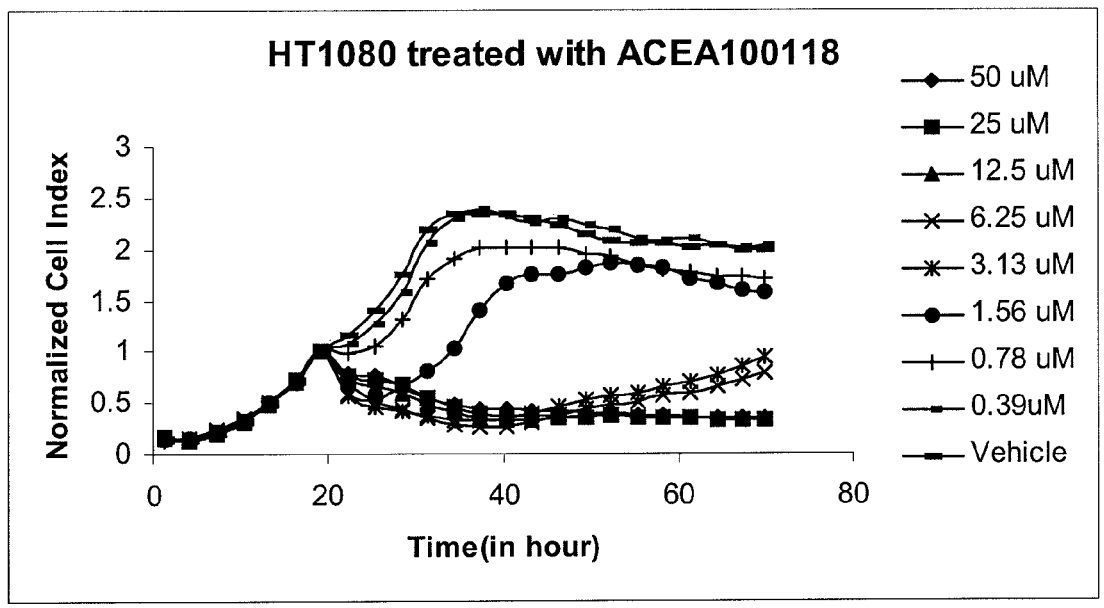
Figure 27:
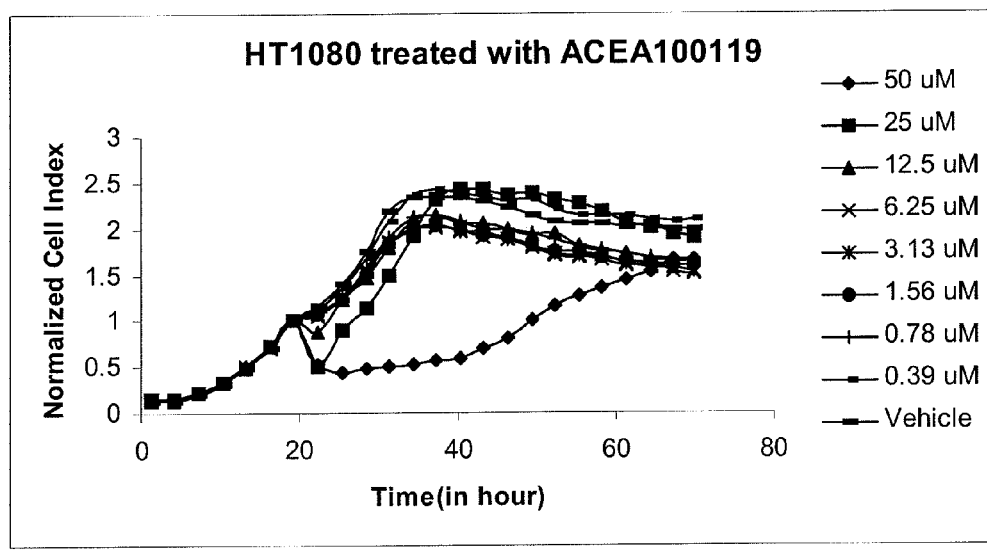
Figure 6:
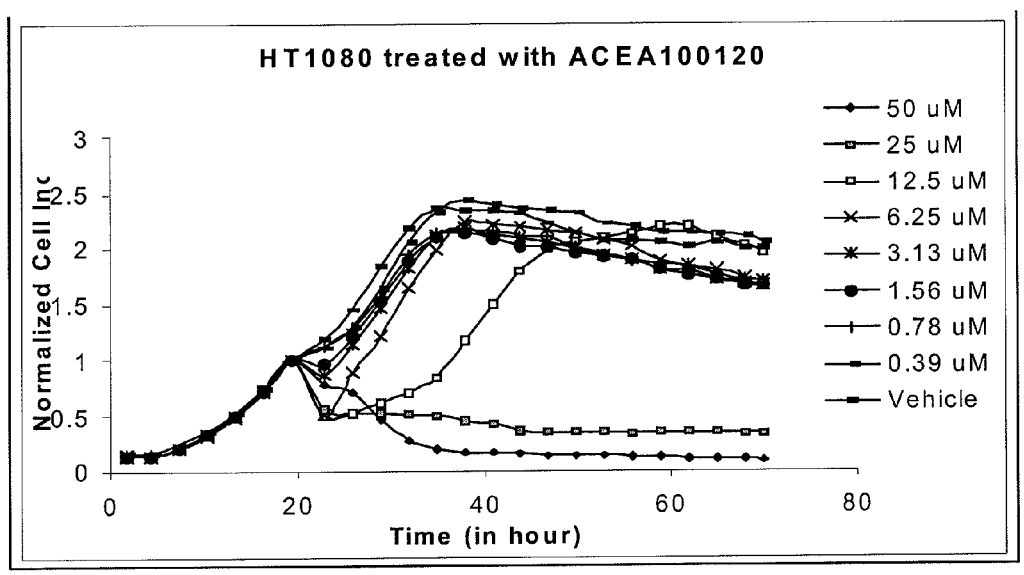

The kinetic inhibition of proliferation of HT1080 cancer cells and cytotoxicity effects of the DBTS derivatives on HT1080 cancer cells were measured on the RT-CES system. The DBTS derivatives are ACEA100107, ACEA100109, ACEA100111, ACEA100114, ACEA100115, ACEA100116, ACEA100117, ACEA100118, ACEA100119, and ACEA100120. The HT1080 cells (human fibrosarcoma) were seeded into the wells of 16x or 96x microtiter plate devices (electronic plates) at the seeding density of 5000 cells/well. After 20 hour incubation at 5% $CO_2$ and 37° C. till the cells reached the growth phase, the serially diluted DBTS-derivatives at the concentration ranging from 50 uM to 0.38 uM were added to the cells, and the cell response to the DBTS derivatives was monitored and recorded in real time for 48 hours on the RT-CES system. FIG. 27 shows the kinetic curves of interactions between cells and DBTS-derivatives at different concentrations. The cell index curves were normalized against the cell index values at a time point just after compound addition (approximately 18-24 hrs after cell seeding).

EXAMPLE 23

Suppression of Microtubule Dynamics by DBTS and its Derivative Compounds ACEA100108 and ACEA100116 Overview Microtubules are important in numerous cellular processes, including mitosis when the duplicated chromosomes are separated into two identical sets before cleavage of the cell into two daughter cells. The key role of microtubules and their dynamics in mitosis and cell division make microtubules an important target for anticancer drugs. In cells during interphase, microtubules exchange their tubulin with soluble tubulin in the cytoplasmic pool with half times of ~3 minutes to several hours. With the onset of mitosis, the interphase microtubule network disassembles and is replaced by a population of highly dynamic microtubules which forms the mitotic spindle and moves the chromosomes. Mitotic spindle microtubules are 20-50 times more dynamic than microtubules in interphase cells, and some spindle microtubules exchange their tubulin with tubulin in the soluble pool with half-times as rapid as 15 seconds.

The dynamics of mitotic spindle microtubules are exquisitely sensitive to modulation by regulators and to disruption by microtubule-active drugs. Microtubule-targeted drugs can alter microtubule polymerization and dynamics in a wide variety of ways. The mechanisms of action of three ACEA compounds designated as DBTS, ACEA100108, and ACEA100116 with respect to (1) the ability to influence the microtubule network in cultured cells, (2) the ability to influence microtubule assembly in vitro and (3) the ability to influence microtubule dynamics in vitro, are described below.
Methods
Cell Culture and Immunocytochemistry. COS cells were grown in DMEM media supplemented with non-essential amino acids, 10% FBS, antibiotic-antimycotic (Gibco BRL) at 37° C. and 5.5% $CO_2$. For immunofluorescence microscopy, cells were plated on polylysine coated coverslips and treated with various concentrations of the three ACEA compounds, paclitaxel or vinblastine for either 4 or 24 hours (see individual figures for concentrations used in any given experiment). Cells were then rinsed once with warm PBS, fixed with cold methanol, rinsed again in PBS and blocked overnight at 4° C. in PBT (PBS, 1% BSA, 0.5% Triton X-100). All subsequent stains and washes were done in PBT at room temperature unless stated otherwise. Cells were stained with the anti-tubulin mouse antibody DM-1 at 1:1000 for 1 hour, washed four times for 15 minutes each and then treated with Cy-3 conjugated goat anti mouse antibody at 1:100 for 1 hour in the dark. Next, samples were washed four times for 15 minutes each in PBT in the dark followed by a final 15 minute wash in PBS in the dark. Samples were then viewed by laser scanning confocal microscopy.

Microtubule Assembly Assays. Microtubule seeds were synthesized by incubating purified bovine brain tubulin with 1 mM GTP, 10% glycerol and 10% DMSO at 35° C. for 30 minutes, followed by shearing by passing the assembled microtubules 6 times through a 27 gauge needle. Microtubule assembly was assayed by adding 27.5 ul of microtubule seeds to spectrophotometer cuvettes (maintained at 35° C.) containing 247.5 ul purified bovine brain tubulin in a PEM-100 buffer (100 mM Pipes pH=6.8, 1 mM EDTA, 1 mM $MgSO_4$) supplemented with 1 mM GTP (and drug where applicable) and monitoring the $OD_{400}$ for 2 hours. Since the compounds are dissolved in DMSO and DMSO can have a significant effect on microtubule assembly, DMSO was added to all cuvettes so as to equal the largest volume of drug added to reactions. It should be noted that the initial velocity of the microtubule assembly reactions is so fast that one can not always catch the initial rise on the light scattering profile because it is occurring while samples are being prepared. However, all samples start at the same optical density, since they are identical with the exception of the drug being introduced.

Tubulin Purification and Microtubule Dynamics Assays. Tubulin was purified, as described in the literature ("Kinetic stabilization of microtubule dynamic instability in vitro by vinblastine", Toso, R. J., Jordan, M. A., Farrell, K. W., Matsumoto, B. and Wilson, L., *Biochemistry*, 1993, 32, 1285-1293). Briefly, microtubule-associated protein-rich bovine brain microtubule protein was prepared by three cycles of assembly and disassembly. Tubulin was purified from other microtubule proteins by elution through a Whatman P-11 phosphocellulose column equilibrated in PEM50 (50 mM Pipes, 1 mM $MgSO_4$, 1 mM EGTA, 0.1 mM GTP). Purified tubulin (>99% pure) was drop-frozen in liquid nitrogen and stored at −70° C. Purified tubulin (15 µM tubulin dimer) was polymerized at the ends of sea urchin (*Strongylocentrotus purpuratus*) axonemal seeds at 37° C. in the presence or absence of ACEA 01, 08 or 16 in PMEM buffer (87 mM Pipes, 36 mM MES, 1.4 mM $MgCl_2$, 1 mM EDTA, pH 6.8) and 2 mM GTP. The dynamics of individual microtubules were recorded at 37° C. using differential interference contrast enhanced video microscopy. The ends were designated as plus or minus on the basis of the growth rate, the number of microtubules that grew at opposite ends of the seeds, and the relative lengths of the microtubules (Panda, D., Goode, B. L., Feinstein, S. C. and Wilson, L., Kinetic stabilization of microtubule dynamics at steady state by tau and microtubule-binding domains of tau, *Biochemistry*, 1995, 34, 11117-11127; Walker, R. A., O'Brien, E. T., Pryer, N. K., Soboeiro, M. F., Voter, W. A., Erickson, H. P. and Salmon, E. D., Dynamic instability of individual microtubules analyzed by video light microscopy: rate constants and transition frequencies, *J. Cell Biol.* 1988, 107, 1437-1448). Plus ends were analyzed for 10 minutes per slide during the steady-state phase of polymerization (~45 min after initiation of polymerization). Life histories of individual microtubules were collected as described by Panda et al. 1995 (Panda, D., Goode, B. L., Feinstein, S. C. and Wilson, L., Kinetic stabilization of microtubule dynamics at steady state by tau and microtubule-binding domains of tau, *Biochemistry*, 1995, 34 11117-11127) with modifications. Data points were collected at 1-3 s intervals.

A microtubule was considered to be growing or shortening if it increased or decreased in length at a rate >0.5 µm/min. microtubules exhibiting growth rates of <0.5 µm/min over a period greater than 30 s were considered to be in an attenuated state. Average rates, lengths and durations are the averages of independent events. The catastrophe frequency was calculated by dividing the number of shortening events by the total time of growth and attenuation tracked, and rescue frequency was calculated by dividing the number of rescue events by the total time of shortening tracked. To control for experimental error, each condition was filmed over multiple days using at least two distinct tubulin/GTP mixtures (2-3 slides each). No gross variation in microtubule dynamics was observed between mixtures or slides of a given condition. The concentration of drug used in dynamic instability assays was chosen by initially observing microtubules stabilized with half the concentration used in microtubule assembly assays. If most microtubules on a slide were stable, the concentration of drug would be reduced until any given microtubule tracked would have at least two growth or shortening events in the span of 10 minutes.

Figure 28:
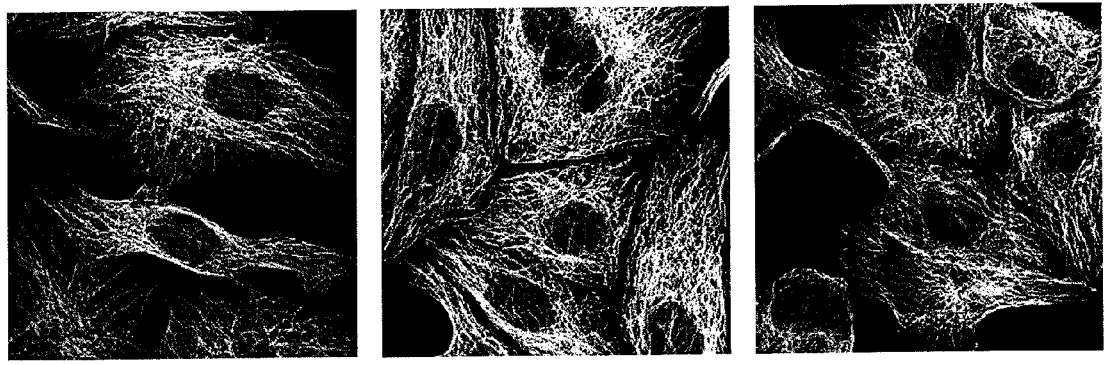
FIG. 28 shows the images of microtubules in control COS cells that were not treated with any drugs.
Figure 29:
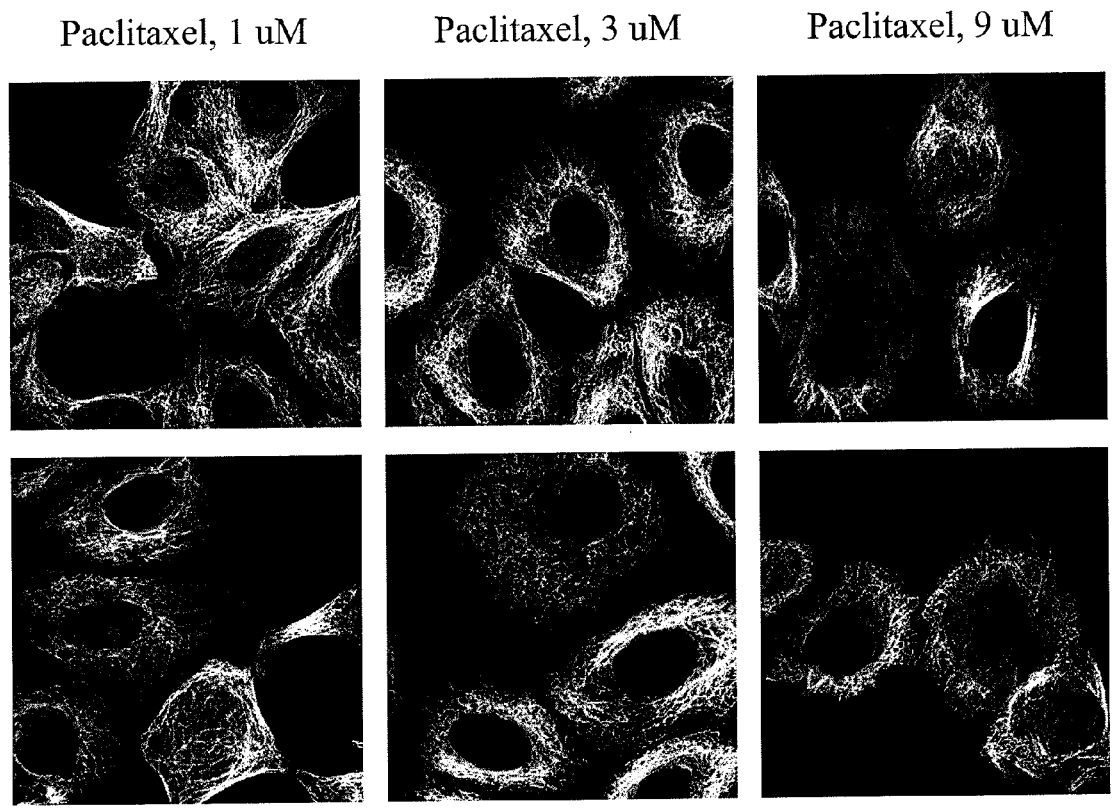
FIG. 29 shows the images of microtubules in COS cells treated with different concentrations of paclitaxel for 4 hours.
Figure 30:
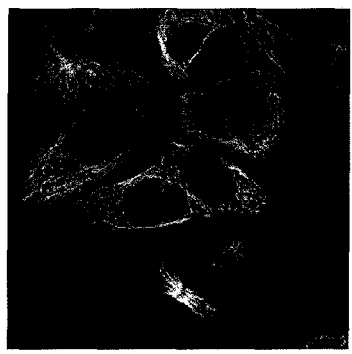
FIG. 30 shows the images of microtubules in COS cells treated with different concentrations of paclitaxel for 24 hours.
Figure 30:
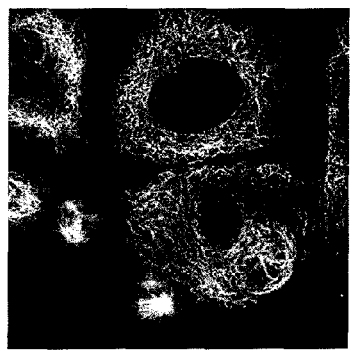
Figure 30:
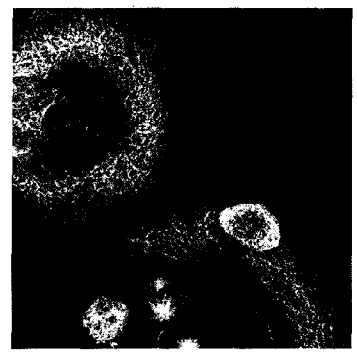
Figure 30:
Figure 30:
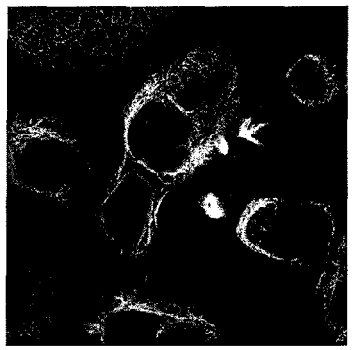
Figure 30:
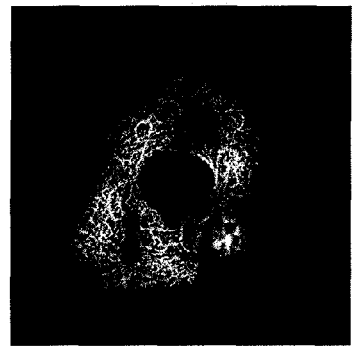

FIGS. 28-38 show the effect of DBTS and organosulfur compounds ACEA 100108 and ACEA100116 on microtubule network in cultured cells. FIG. 28 shows images of microtubules in control cells exposed to no drugs. The microtubule networks appear as expected. FIG. 29 shows images of microtubules in cells exposed to taxol for 4 hours. Microtubules appear bundled in some locations; with increasing concentration, bundling appears more extensive but the microtubules often appear shorter than in the control cells. FIG. 30 shows images of microtubules in cells exposed to taxol for 24 hours. With increasing dosage, microtubule abnormalities increase. As this figure shows, there is increased bundling and the short microtubules persist. Additionally, major cellular abnormalities become apparent.

Figure 31:
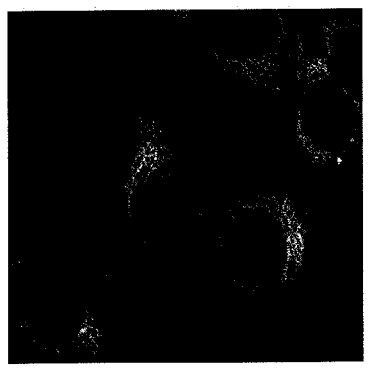
FIG. 31 shows the images of microtubules in COS cells treated with different concentrations of vinblastine for 4 hours.
Figure 31:
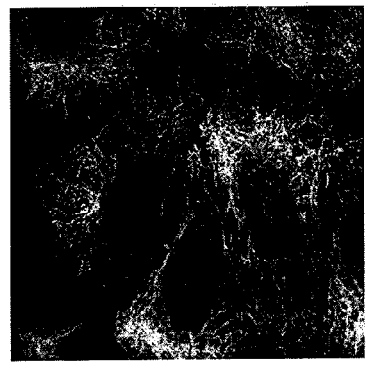
Figure 31:
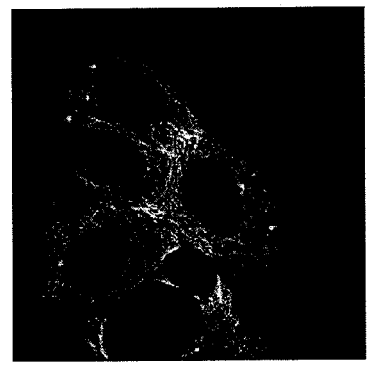
Figure 31:
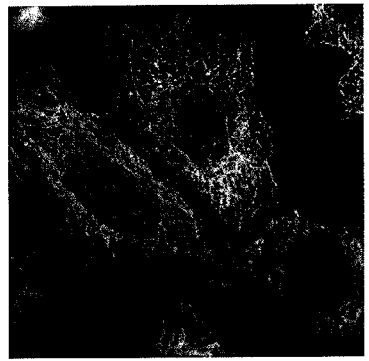
Figure 31:
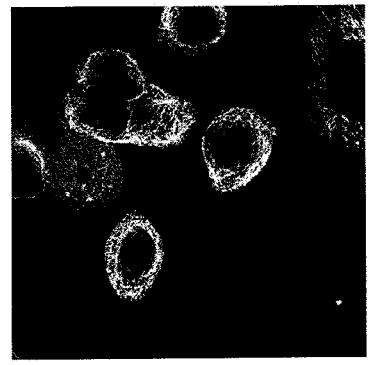
Figure 31:
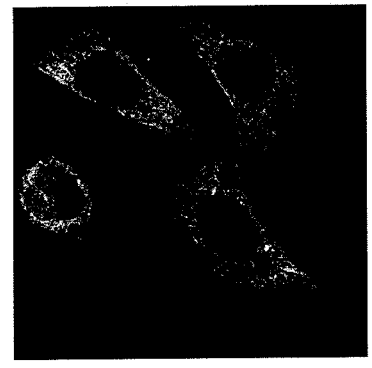
Figure 32:
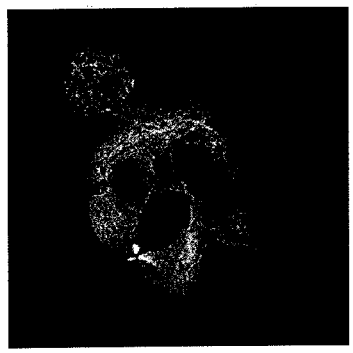
FIG. 32 shows the images of microtubules in COS cells treated with different concentrations of vinblastine for 24 hours.
Figure 32:
Figure 32:
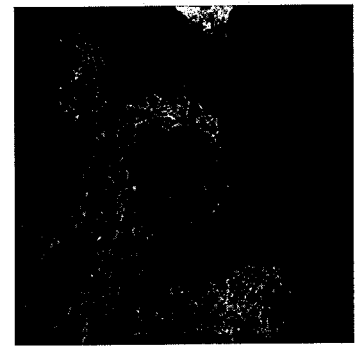
Figure 32:
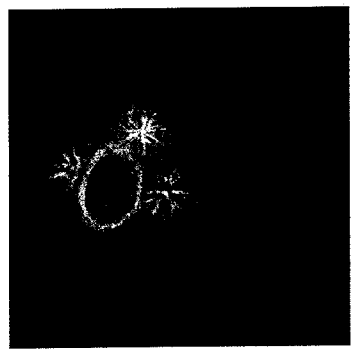
Figure 32:
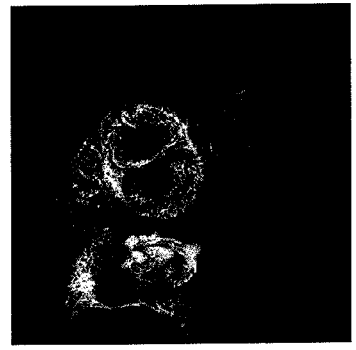
Figure 32:
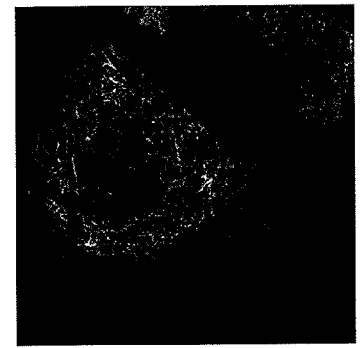

FIG. 31 shows images of microtubules in cells exposed to vinblastine for 4 hours. With increasing dosage, the microtubule network begins to fall apart and the microtubules become much shorter. FIG. 32 shows images of microtubules in cells exposed to vinblastine for 24 hours. As this figure shows, major cell abnormalities are widespread in the microtubule network.

Figure 33:
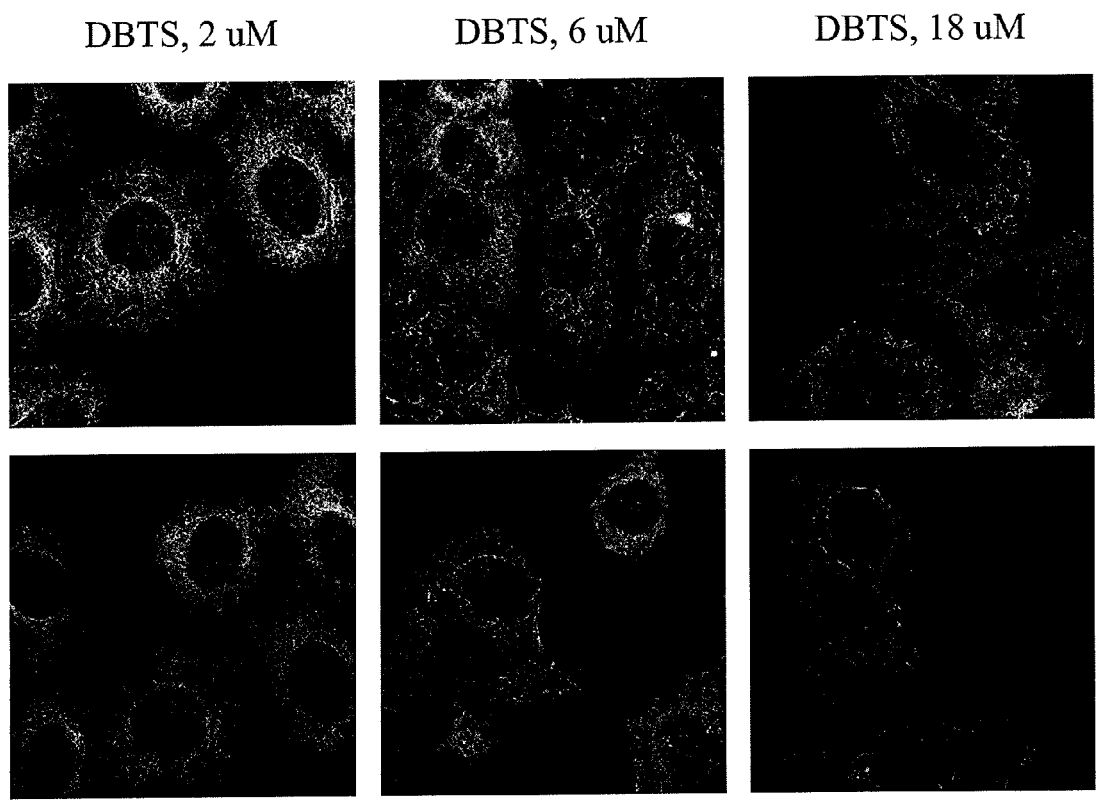
FIG. 33 shows the images of microtubules in COS cells treated with different concentrations of DBTS for 4 hours.
Figure 34:
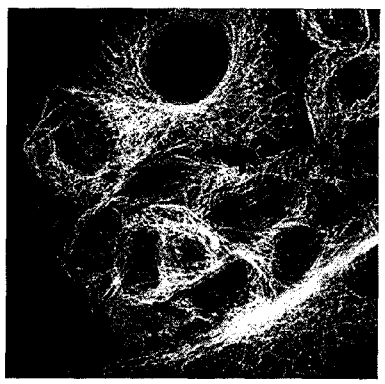
FIG. 34 shows the images of microtubules in COS cells treated with different concentrations of DBTS for 24 hours.
Figure 34:
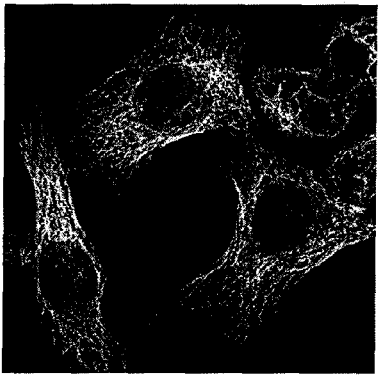

FIG. 33 shows images of microtubules in cells exposed to DBTS for 4 hours. The microtubule network is completely disrupted; only very short microtubules exist and the overall level of tubulin in microtubules appears to be significantly reduced. This effect could be quantitated biochemically by non-ionic detergent extraction and immunoblotting. FIG. 34 shows images of microtubules in cells exposed to DBTS for 24 hours. At the lowest dosage, there are some microtubules present and the cells appear to have partially recovered when compared to cells exposed to the drug for only 4 hours; no cells are viable after treatment for 24 hours with either 6 uM or 18 uM of DBTS.

Figure 35:
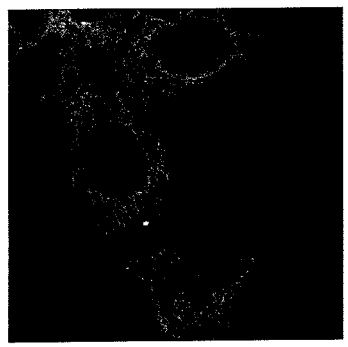
FIG. 35 shows the images of microtubules in COS cells treated with different concentrations of ACEA100108 for 4 hours.
Figure 35:
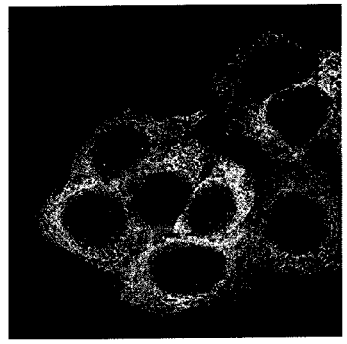
Figure 35:
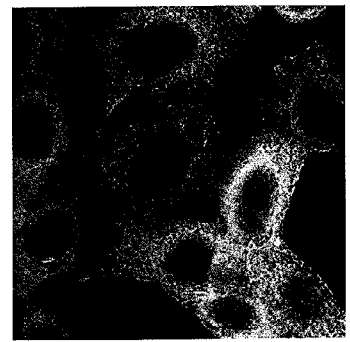
Figure 35:
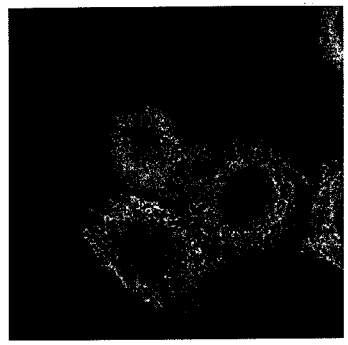
Figure 35:
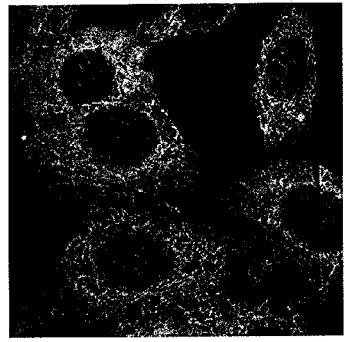
Figure 35:
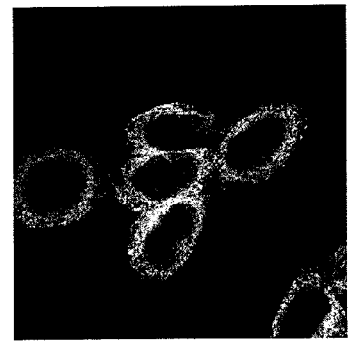
Figure 36:
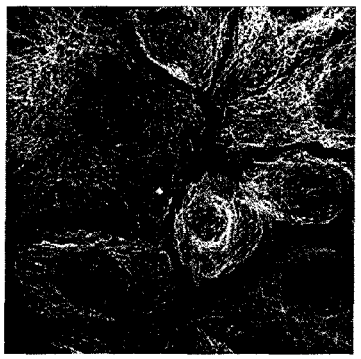
FIG. 36 shows the images of microtubules in COS cells treated with different concentrations of ACEA100108 for 24 hours.
Figure 36:
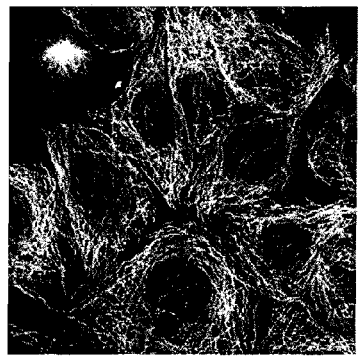
Figure 36:
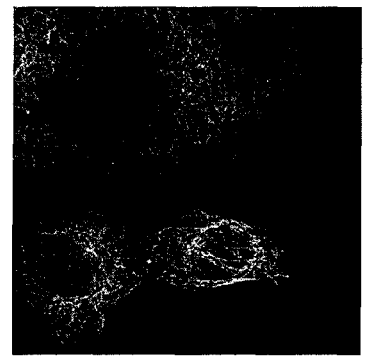
Figure 36:
Figure 36:
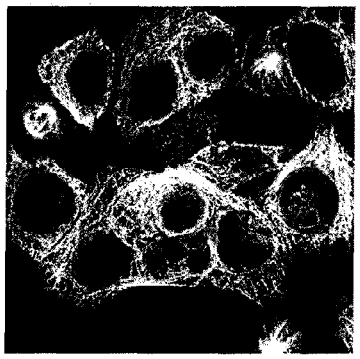
Figure 36:
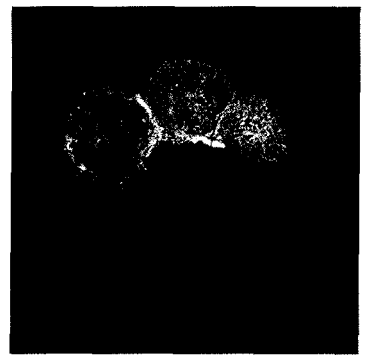

FIG. 35 shows images of microtubules in cells exposed to ACEA100108 for 4 hours. Similar to DBTS, the microtubule network is markedly altered at all concentrations tested. Microtubules are very short and the overall level of microtubule content appears to be reduced. At the highest concentration, cells often round up. FIG. 36 shows images of microtubules in cells exposed to ACEA100108 for 24 hours. At both 1 uM and 3 uM, the cells seem to have made somewhat of a recovery between 4 and 24 hours. The microtubule networks in both cases appear relatively normal. However, at 9 uM, the microtubules appear short and the network is abnormal.

Figure 37:
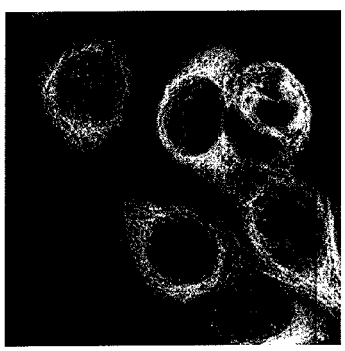
FIG. 37 shows the images of microtubules in COS cells treated with different concentrations of ACEA100116 for 4 hours.
Figure 37:
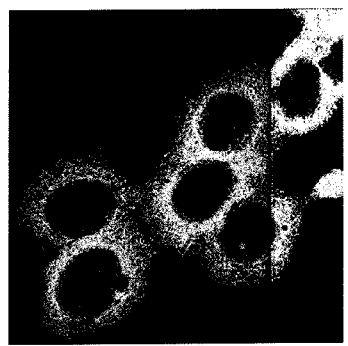
Figure 37:
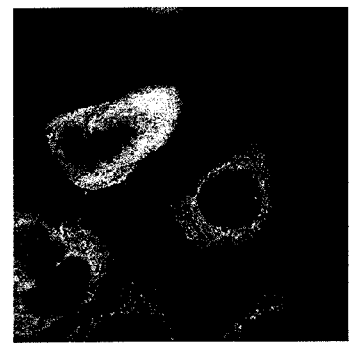
Figure 37:
Figure 37:
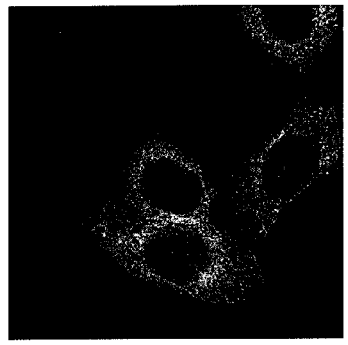
Figure 37:
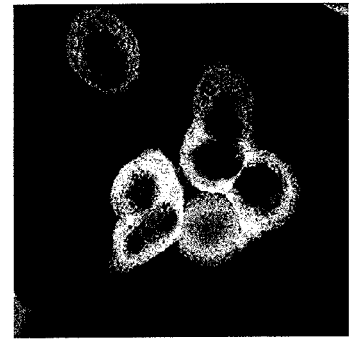
Figure 38:
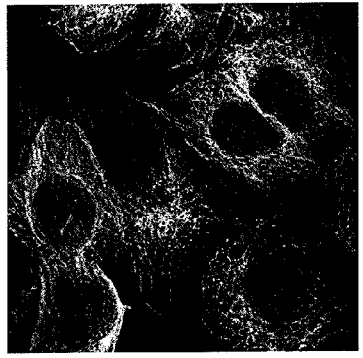
FIG. 38 shows the images of microtubules in COS cells treated with different concentrations of ACEA100116 for 24 hours.
Figure 38:
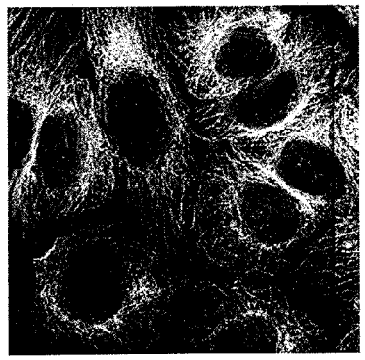
Figure 39A:
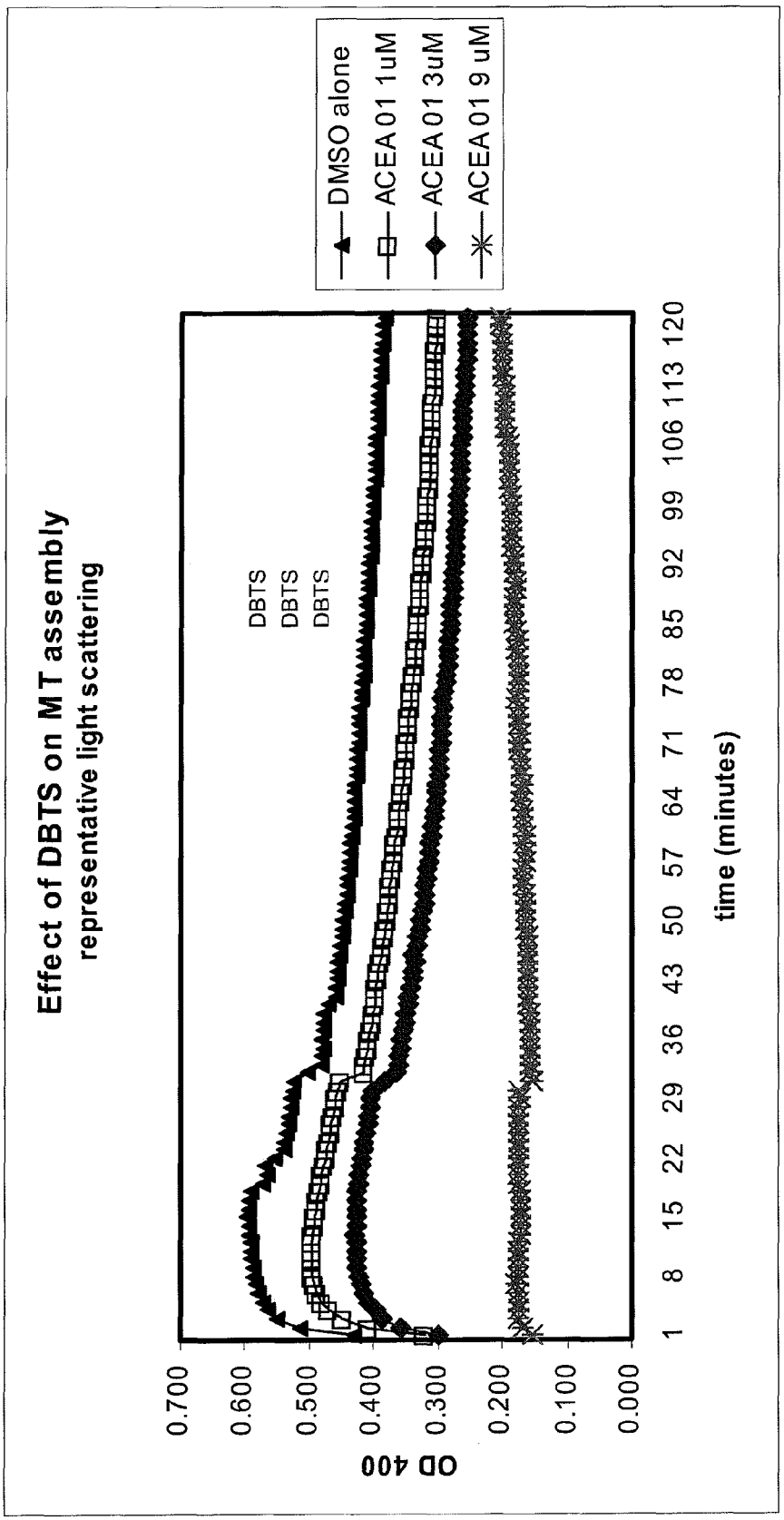
FIG. 39a shows the result of the in vitro microtubule assembly assays using pure tubulin (MAP-free) and DBTS.
Figures 1, 39B:
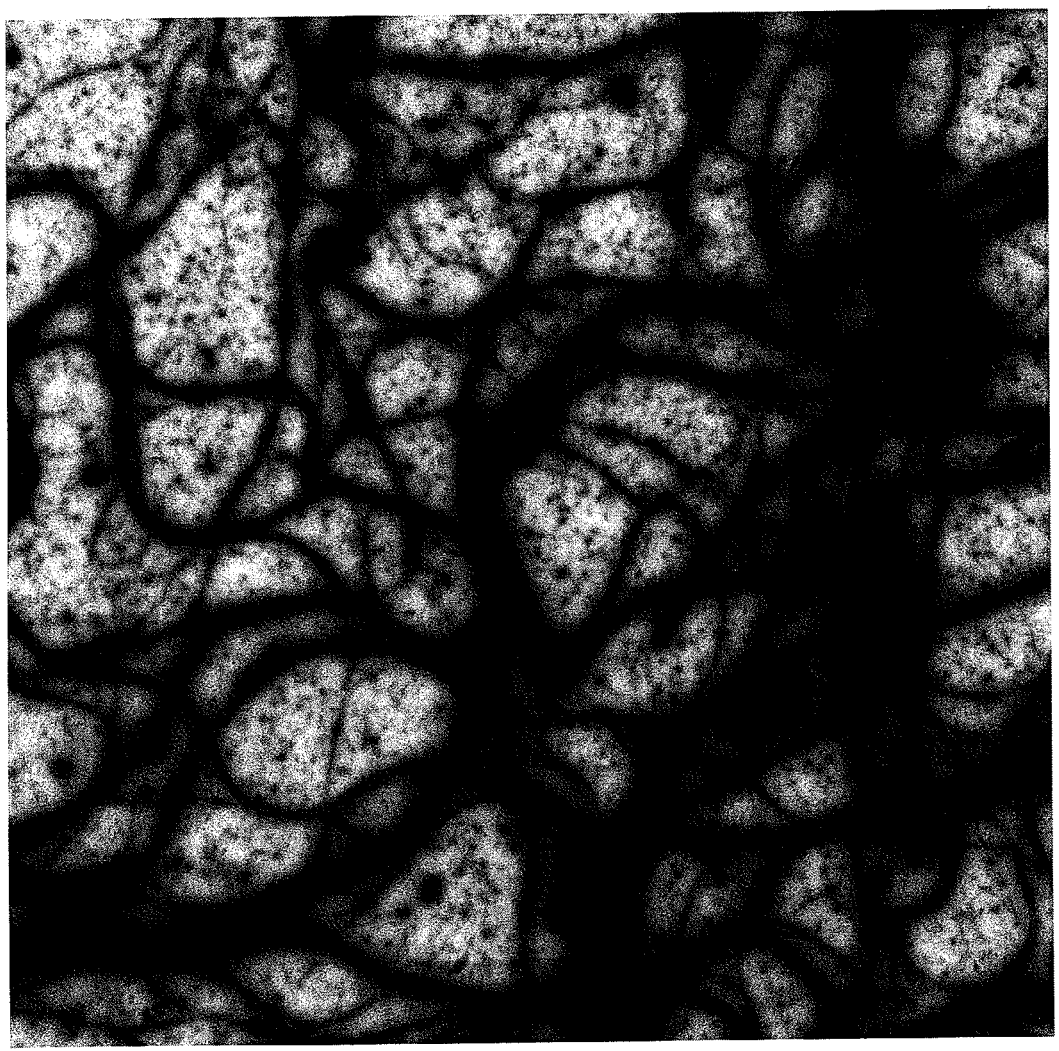
FIG. 39b shows the electron microscopic images of microtubules assembled in vitro in the absence of any drug.
Figures 2, 39B:
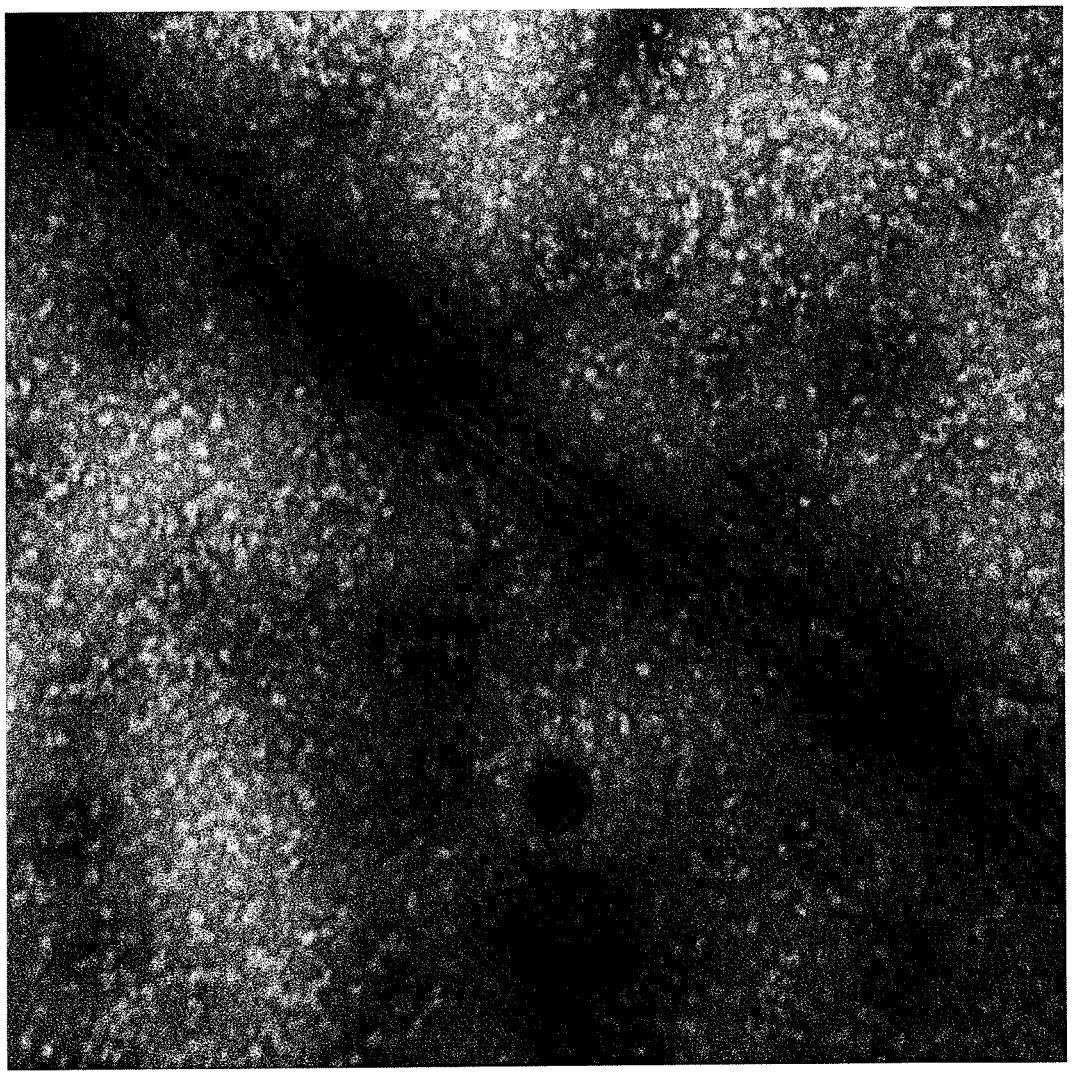
Figures 3, 39B:
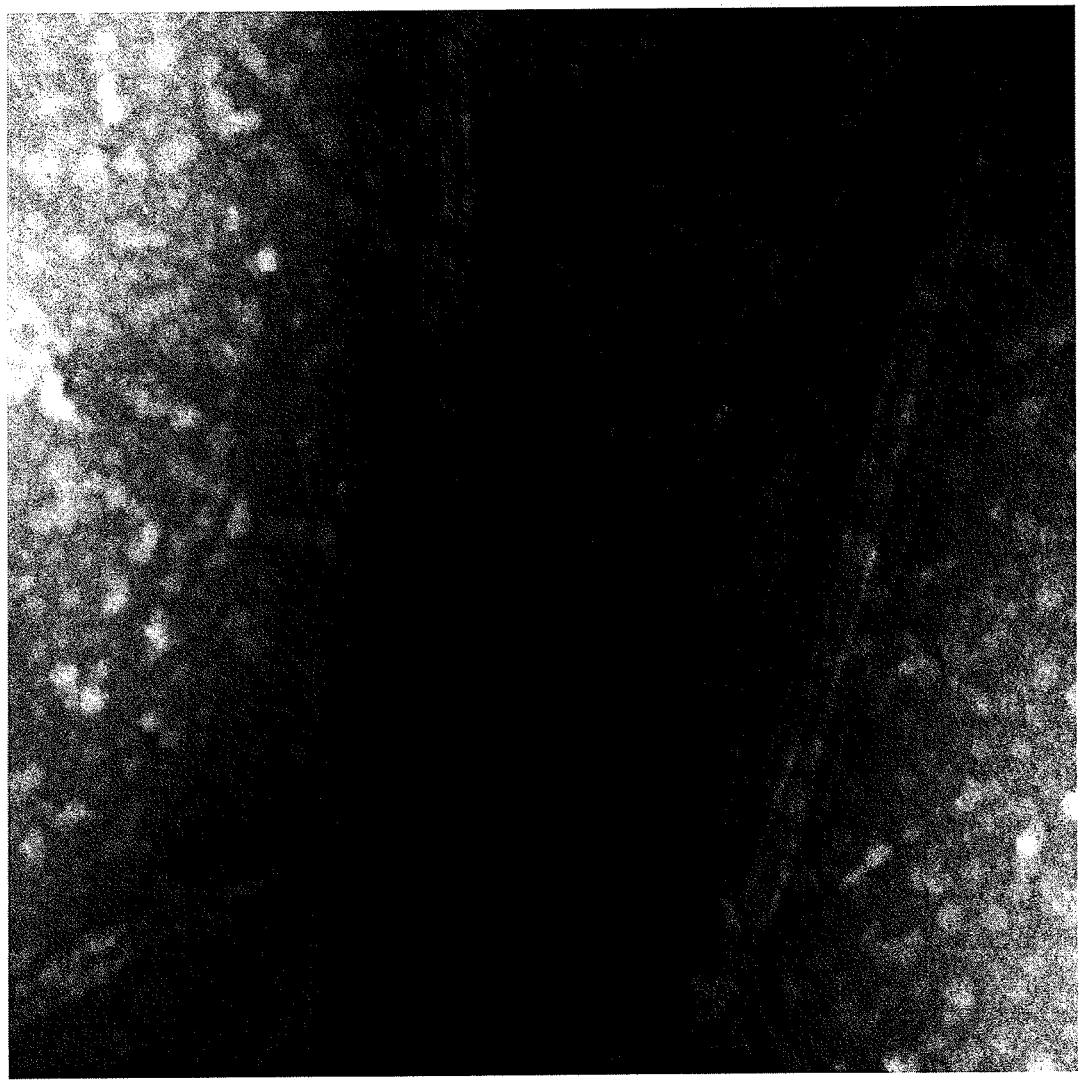
Figures 1, 39C:
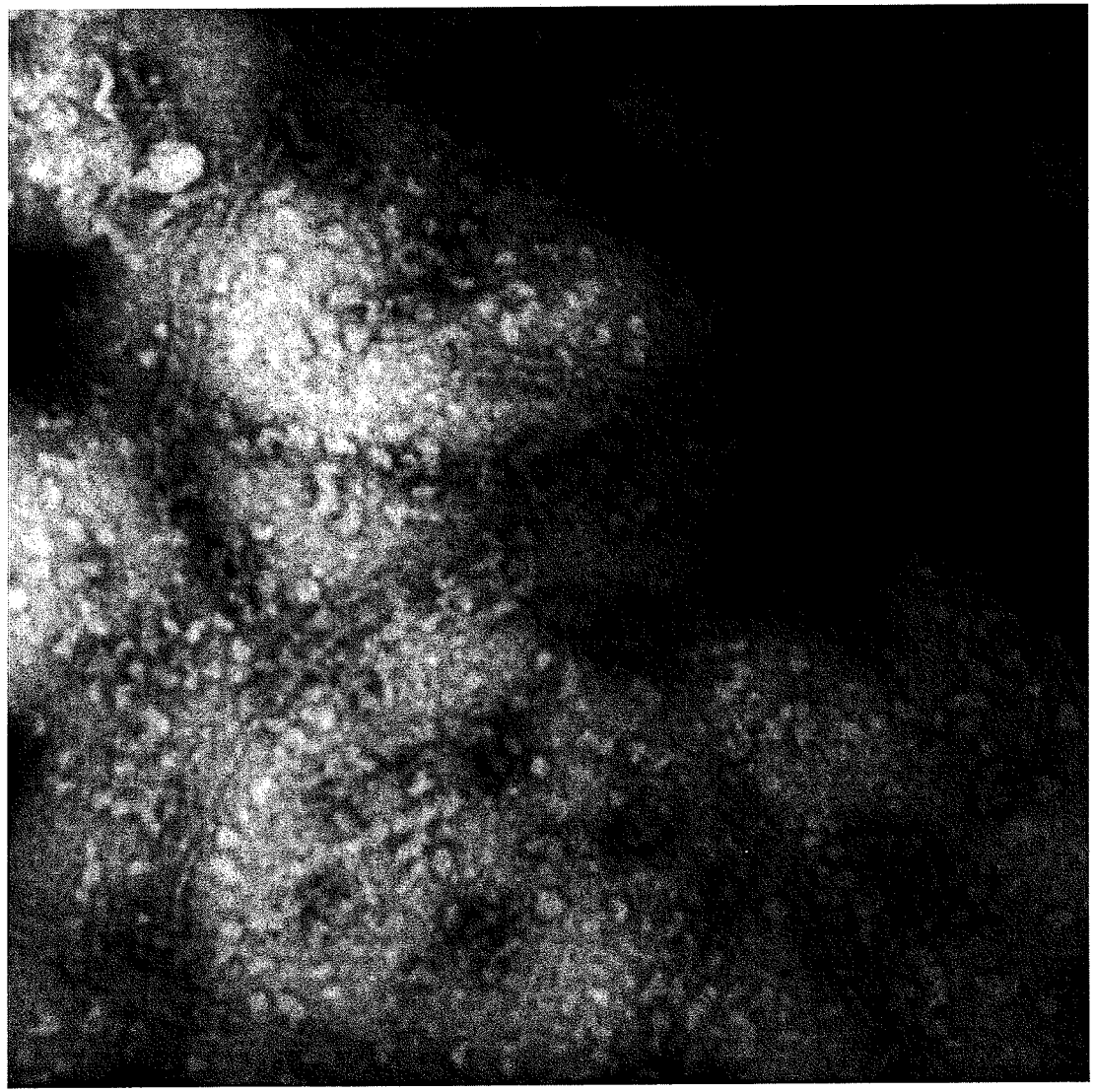
FIG. 39c shows the electron microscopic images of microtubules assembled in vitro in the presence of 3 uM DBTS.
Figures 2, 39C:
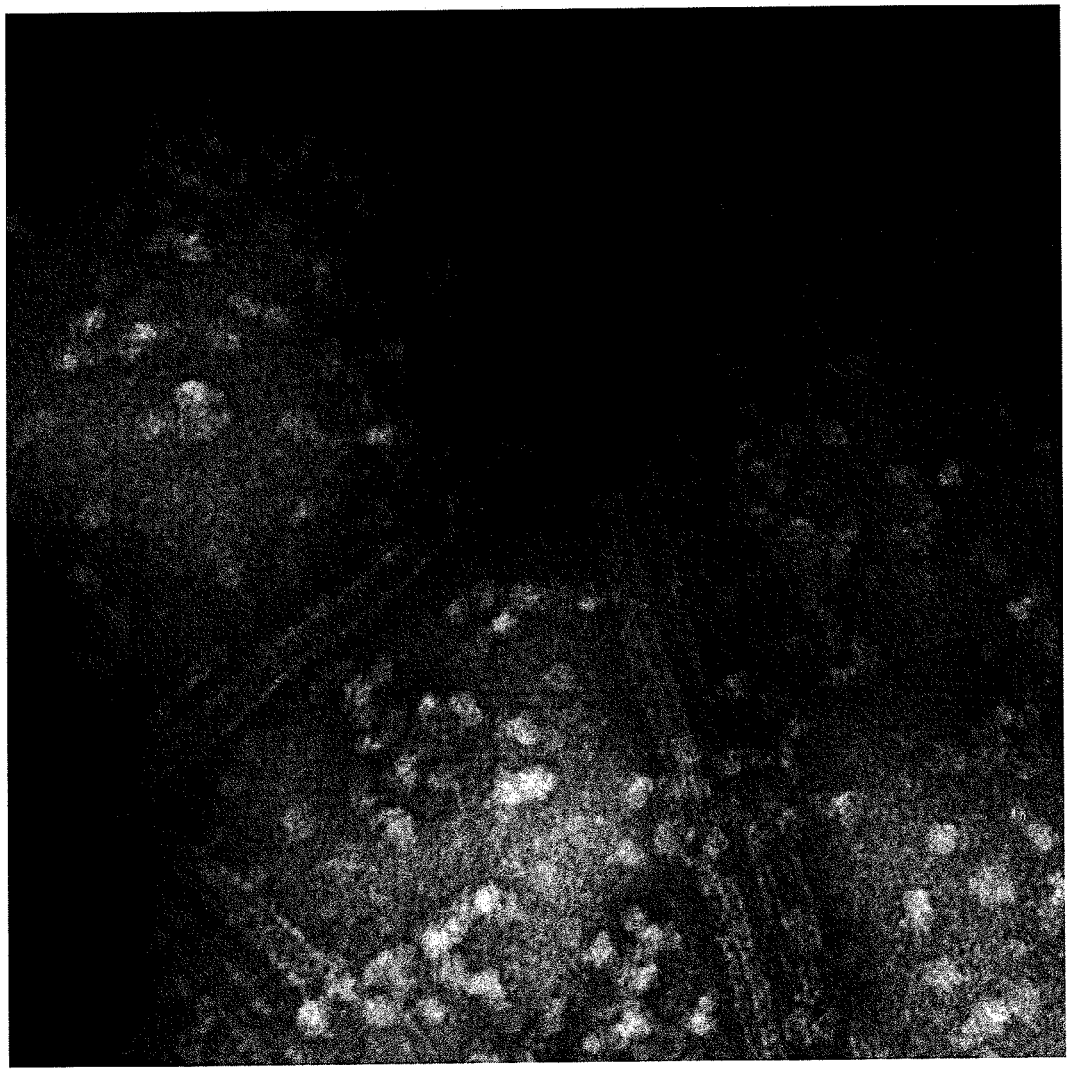

FIG. 37 shows images of microtubules in cells exposed to ACEA100116 for 4 hours. Remnants of the microtubule network remain at 1 uM, but at the two higher concentrations, microtubules appear very short and abnormal. Cells are not elongated but rather appear to round up in a dose-dependent manner. FIG. 38 shows images of microtubules in cells exposed to ACEA100116 for 24 hours. Cells treated with only 1 uM ACEA100116 appear relatively normal; essentially all cells treated with 3 uM or 9 uM were dead after 24 hours of exposure to ACEA100116.

Figure 40:
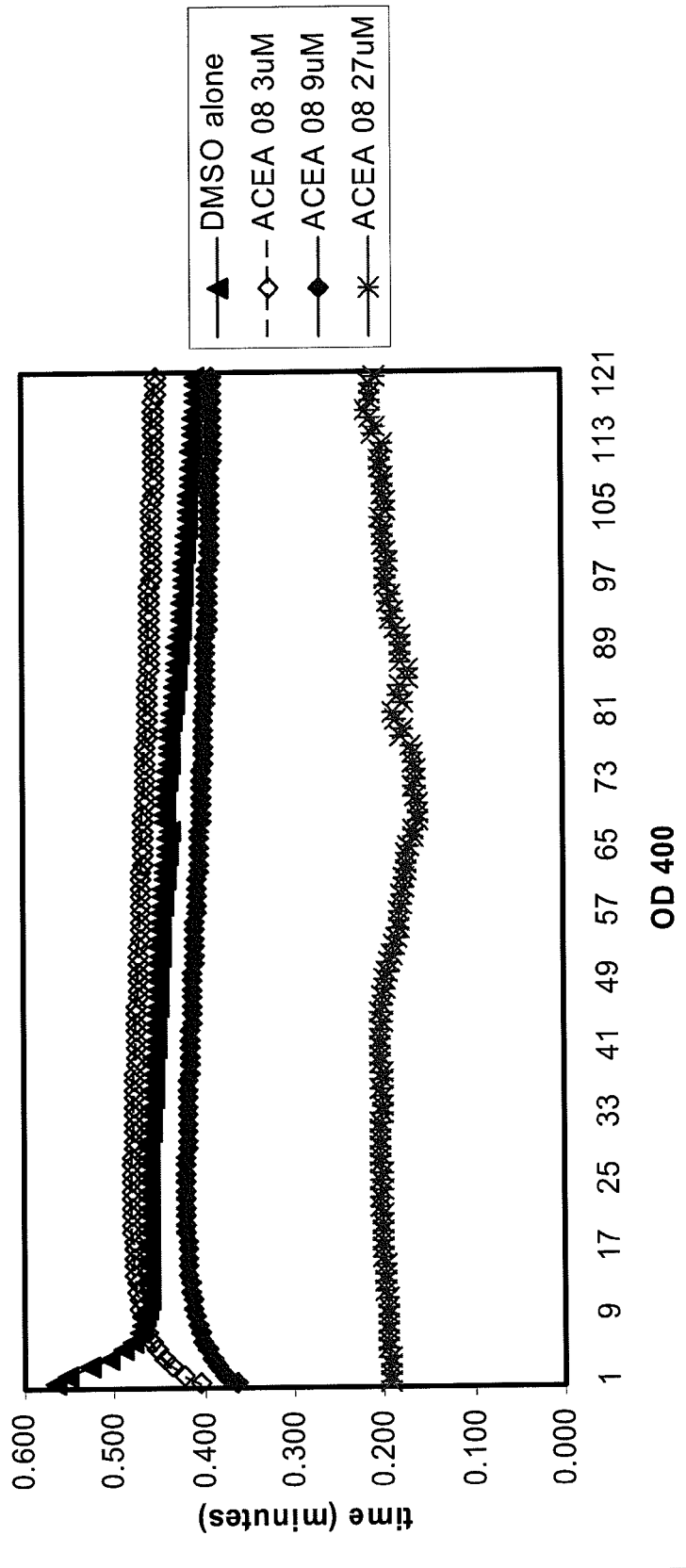
FIG. 40 shows the result of the in vitro microtubule assembly assays using pure tubulin (MAP-free) and ACEA100108.
Figure 41:
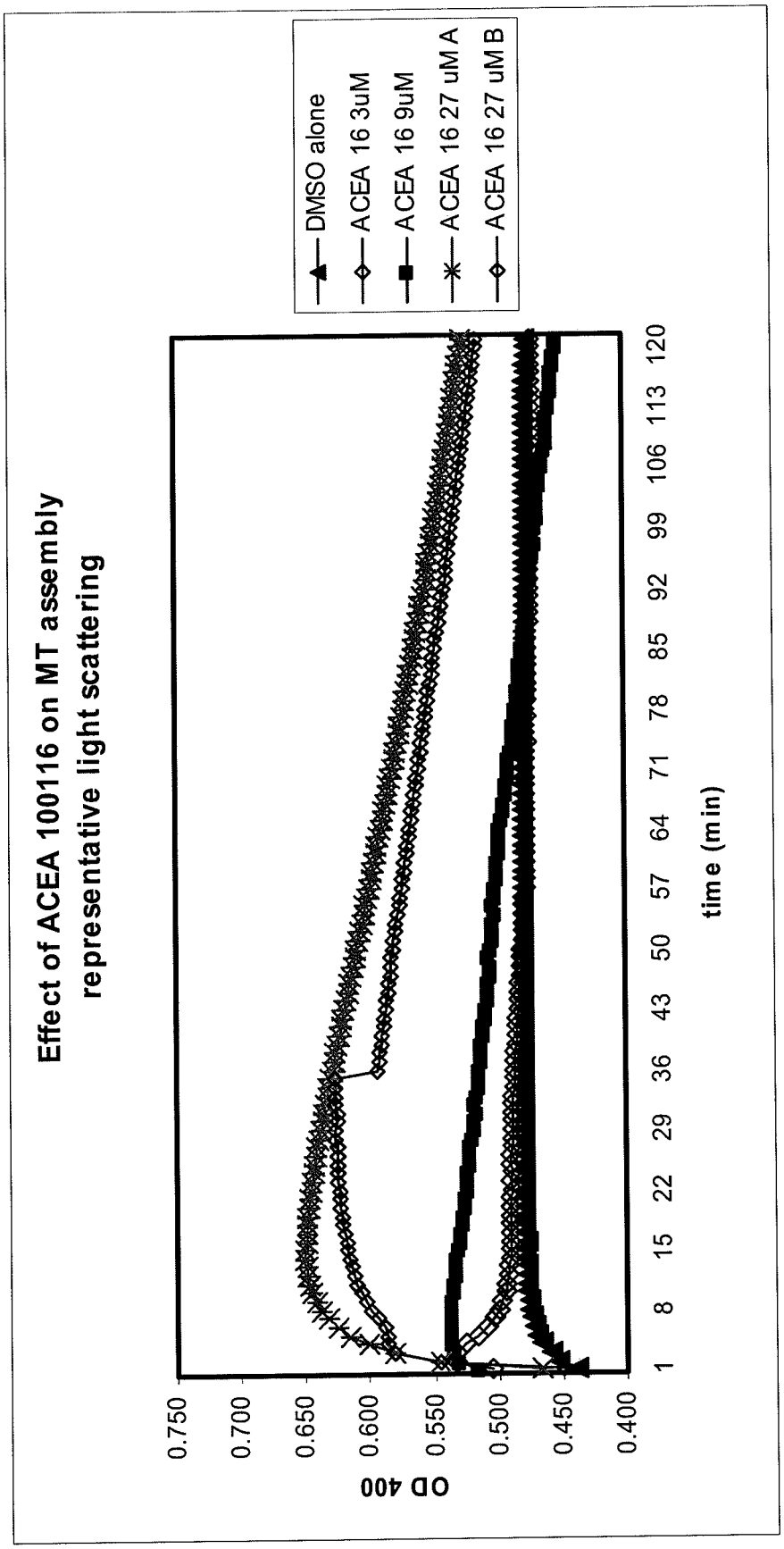
FIG. 41 shows the result of the in vitro microtubule assembly assays using pure tubulin (MAP-free) and ACEA100116.

FIGS. 39-41 show the effect of DBTS and organosulfur compounds ACEA 100108 and ACEA100116 on microtubule assembly in vitro. As shown in FIG. 39a, all doses of DBTS inhibit the extent of microtubule assembly significantly. The effect is especially prominent at 9 uM. Microtubule structure of both the control (FIG. 39b) and drug treated (FIG. 39c) samples were visualized by electron microscopy. As shown in FIG. 40, lower dosages of ACEA100108 had minimal effects upon microtubule assembly. In contrast, 27 uM ACEA100108 had a marked inhibitory effect upon the extent of microtubule assembly.

As shown in FIG. 41, ACEA100116 is very different that DBTS and ACEA100108. Whereas the other two drugs inhibit microtubule assembly, ACEA100116 promotes microtubule assembly. This is apparent at both 9 uM and 27 uM. This plot also exhibits a common, but not well understood, phenomena known as "overshooting" in which the light scattering pattern does not plateau but rather steadily declines. Nonetheless, it is clear that ACEA100116 promotes rather than inhibits microtubule assembly in vitro.

Furthermore, DBTS, ACEA100108 and ACEA100116 were shown to influence microtubule behavior in vitro. As seen in Table 37, all three drugs altered the pattern of microtubule dynamics. DBTS did not affect the microtubule growth rate but did increase the average duration of growth events and consequently the average length grown in a growth event. It also increased the percentage of time spent growing. The average length of shortening events was also reduced.

ACEA100108 also increased the duration of growth events and the average length of growth events; it also had a strong effect upon the length of shortening events; this effect was even more pronounced than that of DBTS and ACEA100116 exhibited significantly different effects than either of the other two drugs. ACEA100116 increased the growth rate but had little effect upon the length of growing events. It had no effect upon the rate of shortening, but had a strong effect upon the length of shortening events. While the cell imaging data can not distinguish between the drugs binding to tubulin or microtubule associated proteins, the in vitro microtubule assembly and in vitro microtubule dynamics assays both used only purified, MAP-free tubulin. These observations demonstrate that all three drugs interact directly with tubulin.

TABLE 37

DBTS and its derivative compounds ACEA100108 and ACEA100116 suppress microtubule dynamics.

|  | Tubulin alone control | DBTS .1uM | ACEA100108 .2uM | ACEA 100116 .07uM |
| --- | --- | --- | --- | --- |
| Growth Rate ± SEM (um/min) | 1.44 ± 0.1 | 1.55 ± 0.1 | 1.59 ± 0.1 | 1.79* ± 0.1 |
| Length of Excursion (um) | 2.34 ± 0.2 | 3.34 ± 0.3* | 3.24 ± 0.3* | 2.15 ± 0.2 |
| Duration of Event (min) | 1.63 ± 0.2 | 2.21 ± 0.3 | 2.04 ± 0.3 | 1.2 ± 0.2 |
| % time spent in growth phase | 31 | 45 | 30 | 25 |
| Shortening Rate ± SEM (um/min) | 44.90 ± 12.6 | 35.40 ± 6.0 | 35.8 ± 4.3 | 42.0 ± 8.3 |
| Length of Excursion (um) | 10.54 ± 0.5 | 6.02 ± 0.3* | 3.79 ± 0.3* | 4.55 ± 0.2* |
| Duration of Event (min) | 0.23 ± 0.06 | 0.17 ± 0.04 | 0.11 ± 0.02 | 0.11 ± 0.02 |
| % time spent in shortening phase | 3 | 3 | 1 | 2 |

TABLE 37-continued

DBTS and its derivative compounds ACEA100108 and ACEA100116 suppress microtubule dynamics.

|  | Tubulin alone control | DBTS .1uM | ACEA100108 .2uM | ACEA 100116 .07uM |
|---|---|---|---|---|
| % time spent in attenuation phase | 66 | 52 | 69 | 73 |
| Mean duration of attenuation ± SEM | 2.63 ± 0.3 | 2.15 ± 0.3 | 3.74 ± 0.7 | 2.22 ± 0.2 |
| Frequency of transitions ± SD (events/min) | | | | |
| Catastrophes | 0.12 ± 0.03 | 0.17 ± 0.04 | 0.09 ± 0.03 | 0.18 ± 0.04 |
| Rescues | 4.3 ± 1.1 | 5.3 ± 1.3 | 9.4 ± 3.0 | 8.7 ± 2.1 |
| Total | 0.46 ± 0.06 | 0.50 ± 0.07 | 0.32 ± 0.06 | 0.61 ± 0.08 |
| Dynamicity (um/min) | 1.73 | 1.72 | 0.83 | 1.25 |

As of Mar. 31, 2005
*= p < 0.05 or less

EXAMPLE 24

ACEA100108 Induces Apoptosis in Cancer Cells

To test if ACEA100108 compound induces apoptosis in cancer cells, the A549 human lung cancer cells were treated with 1 uM ACEA100108 and 50 nM paclitaxel or 10 nM vinblastine. Paclitaxel and vinblastine, the two suppressors of microtubule dynamics were used as the positive control. A549 cells were seeded in chamber slides at a density of 10,000 cells/well and 18 hours later were treated with the indicated concentrations of the anti-mitotic compounds ACEA100108, paclitaxel and vinblastine. The cells were incubated with the drugs for 24 hours and then washed 2× with PBS and 3× with binding buffer (10 mM HEPES, pH 7.5, 140 mM NaCl, 2.5 mM $CaCl_2$). The Cells were stained with 1 ug/mL Annexin V-Cy3 conjugate (Red, staining the cells that are starting apoptotic process) and 500 uM 6-CFDA (Green, staining the viable cells) in 1× binding buffer for 20 minutes. The cells were gently washed 3× in 1× binding buffer, mounted, viewed under immunofluorescent microscope and imaged using an attached CCD camera. Note that live cells show staining only with 6-CFDA (green), while necrotic cells will stain only with Annexin V-Cy3 (red). Cells starting the apoptotic process will stain both with AnnexinV-Cy3 and 6-CFDA.

Figure 42:
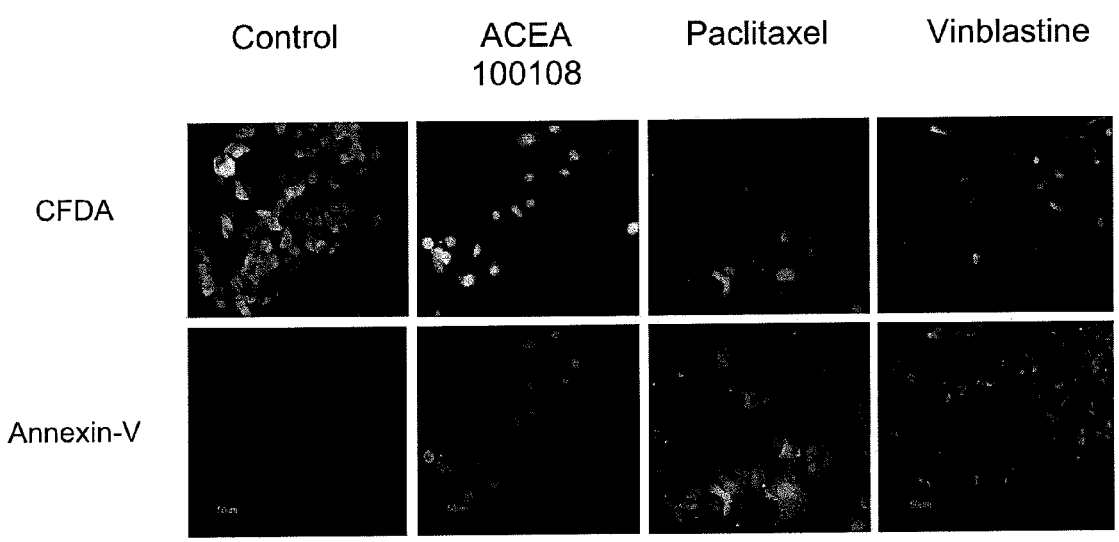
FIG. 42 shows the fluorescent microscope images of 6-CFDA (top panel) and Annexin V (bottom panel) staining of A549 human lung cancer cells treated with treated with 1 uM ACEA100108, 50 nM paclitaxel, 10 nM vinblastine or DMSO for 24 hrs.

As shown in FIG. 42, the cells treated with ACEA100108, paclitaxel, and vinblastine showed strong staining of Annexin V, while the control cells which were only treated with DMSO showed no Annexin V staining. This indicates that ACEA100108 induces apoptosis in A549 human lung cancer cells.

EXAMPLE 25

ACEA100108 Induces G2/M Cell-Cycle Arrest in Cancer Cells

Microtubules are extremely important in the process of mitosis, during which the duplicated chromosomes of a cell are separated into two identical sets before cleavage of the cell into two daughter cells. Compounds which target microtubules such as paclitaxel, and vinblastine suppress the microtubule dynamics and block the process of mitosis. As consequence, cells will be arrested at G2/M phase. To test if ACEA100108 influences the process of mitosis in cancer cell dividing, A549 human lung cancer cells were treated with 25 uM ACEA100108 and 7.8 nM paclitaxel, and the cell-cycle effects of the compounds were detected by flow cytometry.

Figure 43:
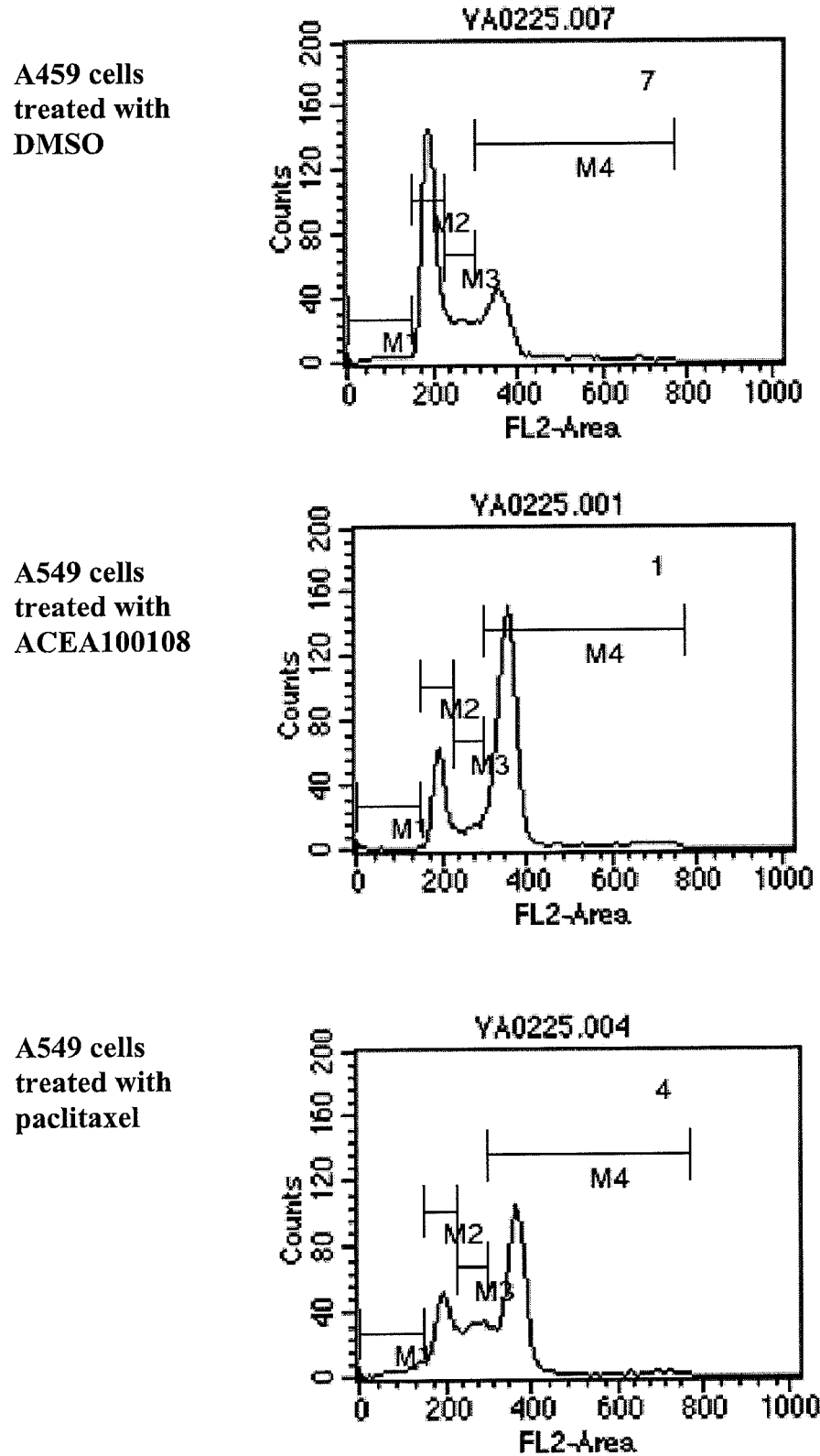
FIG. 43 show the cell cycle distribution of A549 human lung cancer cells after they were treated with 25 uM ACEA100108, 7.8 nM paclitaxel, or DMSO for 24 hrs, as analyzed on a flow cytometry.

In briefly, A549 cells were seeded at a density of 500,000 cells in 60 mm tissue culture dishes. Approximately 18 hours later the cells were treated with the indicated concentrations of anti-mitotic compounds and allowed to further incubate for 24 hours. The cells were washed in PBS, trypsinized, counted and fixed in ice-cold 70% methanol and stored at 4° C. The cells were washed with PBS, stained with propidium iodide and kept on ice until flow cytometry analysis. As shown in FIG. 43, the cell population at G2/M phase increased significantly in cells treated with both ACEA100108 and paclitaxel, compared with the cells treated with DMSO only.

EXAMPLE 26

Large scale synthesis of Di(p-chlorobenzyl)trisulfide (9)

N-Trimethylsilylimidazole (10.67 mL, 97%, d=0.956, actual weight=9.89 g, 70.54 mmol) was dissolved in 70 mL of anhydrous hexanes in a dry 250-mL round-bottom flask. To this stirred solution was added slowly (40-50 min) sulfur dichloride solution in dichloromethane (35.3 mL, 1.0 M, 35.3 mmol) at room temperature under a nitrogen atmosphere. The white precipitate was formed. The reaction mixture was stirred for 50 min, and then cooled to 0° C. under a nitrogen atmosphere. A solution of 4-chlorobenzyl mercaptan (9.5 mL, 96%, actual weight=11.19 g, 70.53 mmol) in 50 mL of anhydrous hexanes was added dropwise under stirring and nitrogen atmosphere for 40-50 min. The resulting reaction mixture was stirred at 0° C. for 1 hour, and then at room temperature for 3 hours. The white to pale yellow solid was filtered off through a pad of Celite and washed with small amount of hexanes. The filtrate was washed with water (200 mL, 100 mL) and then saturated aqueous sodium chloride solution (200 mL). The organic phase was dried over anhydrous sodium sulfate. The drying agent was filtered off, and the filtrate was concentrated under reduced pressure.

The white solid residue was purified by flash chromatography on a silica gel column using hexanes-ethyl acetate (60:1) as an eluent. The fractions were monitored with silica gel TLC using hexanes-ethyl acetate (40:1) as a developing solvent ($R_f$=0.45). The desired fractions were collected, and the solvent was evaporated. The resulting white solid product was re-crystallized from hexanes to give 11.06 g (90%) desired product 9 as white needle crystalline. $^1$H NMR (499.1 MHz, $CDCl_3$) δ 3.98 (s, 4H), 7.23 (d, 4H, J=8.4 Hz), 7.30 (d, 4H, J=8.4 Hz); ES MS m/z 345 (M-1)⁻.

EXAMPLE 27

Large scale synthesis of Di(p-fluorobenzyl)trisulfide (8)

N-Trimethylsilylimidazole (21.42 mL, 97%, d=0.956, actual weight=19.86 g, 141.6 mmol) was dissolved in 140 mL of anhydrous hexanes in a dry 500-mL round-bottom flask. To this stirred solution was added slowly (40-50 min) sulfur dichloride solution in dichloromethane (70.8 mL, 1.0 M, 70.8 mmol) at room temperature under a nitrogen atmosphere. The white precipitate was formed. The reaction mixture was stirred for 50 min, and then cooled to 0° C. under a nitrogen atmosphere. A solution of 4-fluorobenzyl mercaptan (18.04 mL, 20.86 g, 96%, actual weight=20.0 g, 140.8 mmol) in 100 mL of anhydrous hexanes was added dropwise under stirring and nitrogen atmosphere for 40-50 min. The resulting reaction mixture was stirred at 0° C. for 1 hour, and then at room temperature for 3 hours. The white to pale yellow solid was filtered off through a pad of Celite and washed with small amount of hexanes. The filtrate was washed with water (400 mL, 300 mL) and then saturated aqueous sodium chloride solution (400 mL). The organic phase was dried over anhydrous sodium sulfate. The drying agent was filtered off, and the filtrate was concentrated under reduced pressure.

The white solid residue was purified by flash chromatography on a silica gel column using hexanes-ethyl acetate (60:1) as an eluent. The fractions were monitored with silica gel TLC using hexanes-ethyl acetate (40:1) as a developing solvent ($R_f$=0.46). The desired fractions were collected, and the solvent was evaporated. The resulting white solid product was re-crystallized from hexanes to give 14.7 g (67%) desired product as white needle crystalline. The mother liquor was concentrated. Further re-crystallization provided 10-15% more crystalline product. m. p. 61.5-62.1° C.; UV-VIS λ=218 nm (ω, 63700), λ=283 nm (ω, 12000); $^1$H NMR (499.1 MHz, CDCl$_3$) δ 4.00 (s, 4H), 7.01 (t, 4H, J=8.8 Hz), 7.27 (dd, 4H, J=8.8, 5.4 Hz); $^{13}$C NMR (125.7 MHz, CDCl$_3$) δ 42.4, 115.6, 115.8, 131.2, 131.3, 132.4, 162.5 (C—F, J=250 Hz); $^{19}$F NMR (376.5 MHz, CDCl$_3$) δ −114.2; ES MS m/z 337/338 (M+Na)$^+$; Anal. Calcd. for C$_{14}$H$_{12}$F$_2$S$_3$: C, 53.48; H, 3.85; S, 30.59. Found: C, 53.16; H, 4.22; S, 30.24.

EXAMPLE 28

Large scale synthesis of di(p-fluorobenzyl)trisulfide (8) Using Pure Sulfur Dichloride N-Trimethylsilylimidazole (226.6 mL, 97%, d=0.956, actual weight=205.7 g, 1467 mmol) was dissolved in 1200 mL of anhydrous hexane and 560 mL of anhydrous dichloromethane (dried with molecular sieves type 3A) in a dry 3000-mL three-necked flask. To this stirred solution was added slowly (40-50 min) pure sulfur dichloride (55.9 mL, 90.63 g, 880 mmol, 0.6 eq) at room temperature under a nitrogen atmosphere. The reaction took place immediately with precipitate. The reaction mixture was stirred for 50 min, and then cooled to 0° C. under a nitrogen atmosphere. A solution of 4-fluorobenzyl mercaptan (176 mL, 96%, actual weight=200.17 g, 1408 mmol) in 250 mL of anhydrous dichloromethane and 100 mL of anhydrous hexane was added dropwise under stirring and nitrogen atmosphere for 40-50 min. The resulting reaction mixture was stirred at 0° C. for 1 hour, and then at room temperature for 3 hours. The reaction was monitored with TLC using hexane-ethyl acetate (40:1) as a development solvent, and the result indicated that the reaction was normal and completed. The white to pale yellow solid was filtered off through a pad of Celite and washed with small amount of hexane. The filtrate was washed twice with water (1000 mL×2) and then once with saturated aqueous sodium chloride solution (1000 mL). The organic phase was dried over anhydrous sodium sulfate. The drying agent was filtered off, and the filtrate was concentrated under reduced pressure. The crude product was purified by flash chromatography on a silica gel column (8×36 cm) using petroleum ether (60-90° C. fraction)-ethyl acetate (80:1, 60:1, 40:1 and then 20:1) as gradient eluents. The fractions were monitored with silica gel TLC using n-hexane-ethyl acetate (40:1) as a developing solvent ($R_f$=0.46). The desired fractions were collected, and the solvent was evaporated. The resulting white solid product was re-crystallized from 1000 mL of hexane to give 131.0 g of the desired product 8 as white needle crystalline in 59.2% yield (T yield 221.16 g). m. p. 61.5-62.1° C.; UV-VIS λ=218 nm (ω, 63700), λ=283 nm (ω, 12000); $^1$H NMR (499.1 MHz, CDCl$_3$) δ 4.00 (s, 4H), 7.01 (t, 4H, J=8.8 Hz), 7.27 (dd, 4H, J=8.8, 5.4 Hz); $^{13}$C NMR (125.7 MHz, CDCl$_3$) δ42.4, 115.6, 115.8, 131.2, 131.3, 132.4, 162.5 (C—F, J=250 Hz); $^{19}$F NMR (376.5 MHz, CDCl$_3$) δ −114.2; ES MS m/z 337/338 (M+Na)$^+$; Anal. Calcd. for C$_{14}$H$_{12}$F$_2$S$_3$: C, 53.48; H, 3.85; S, 30.59. Found: C, 53.16; H, 4.22; S, 30.24.

The asymmetric trisulfides 41-68 (Scheme 3) can be synthesized by Method B similar to the reported procedure (Derbesy, G.; Harpp, D. N. *Tetrahedron Letters*, 1994, 35, 5381-5384). For example, a solution of phenylthiol (C$_6$H$_5$CH$_2$SH) (10 mmol) and anhydrous pyridine (10 mmol) in 25 mL of diethyl ether is added dropwise over a period of 30 minutes to a cold (−78° C.) stirred solution of sulfur dichloride (10 mmol) in 50 mL of anhydrous diethyl ether. The reaction mixture is stirred for 30 minutes. The corresponding second thiol (10 mmol) and anhydrous pyridine (10 mmol) in 25 mL of diethyl ether is added dropwise over a period of 30 minutes at −78° C., and the reaction mixture is further stirred for an additional 30 minutes. The reaction mixture is washed with water (2 times), 1 N sodium hydroxide solution (2 times), and then water (2 times) until pH is neutral. The organic phase is dried over CaCl$_2$, or anhydrous sodium sulfate, filtered and concentrated. The residue is passed through a short pad of silica gel using hexanes-ethyl acetate as eluent to provide high purity products 41-68 in 40-100% yields.

It is understood that the foregoing detailed description and accompanying examples are merely illustrative, and are not to be taken as limitations upon the scope of the invention. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof. U.S. patents and publications referenced herein are incorporated by reference.

The invention claimed is:
1. A compound having the formula:

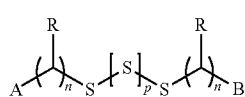

wherein A and B are the same,
A is pyridine, pyridazine, pyrimidine, pyrazine, triazine, isoxazole, isothiazole, oxadiazole, triazole, thiadiazole, pyrazole, imidazole, thiazole, oxazole, pyrrole, thiophene indolizine, indole, isoindole, indoline, benzofuran, benzothiophene, indazole, benzimidazole, benzthiazole, purine, quinoxaline, quinoline, isoquinoline, cinnoline, phthalazine, quinazoline, quinoxaline, naphthyridine, pteridine, acridine, phenazine, phenothiazine, indene, or naphthalene, each of which is optionally substituted with one or more heteroatoms selected from O, N and S; halo; or $C_{1-10}$ alkyl, $C_{3-10}$ cyclic alkyl, $C_{2-10}$ alkenyl or alkynyl, aryl, or heterocycle, each optionally containing one or more heteroatoms;

B is selected from pyridine, pyridazine, pyrimidine, pyrazine, triazine, isoxazole, isothiazole, oxadiazole, triazole, thiadiazole, pyrazole, imidazole, thiazole, oxazole, pyrrole, thiophene indolizine, indole, isoindole, indoline, benzofuran, benzothiophene, indazole, benzimidazole, benzthiazole, purine, quinoxaline, quinoline, isoquinoline, cinnoline, phthalazine, quinazoline, quinoxaline, naphthyridine, pteridine, acridine, phenazine, phenothiazine, and indene, each of which is optionally substituted with one or more heteroatoms selected from O, N and S; halo; or $C_{1-10}$ alkyl, $C_{3-10}$ cyclic alkyl, $C_{2-10}$ alkenyl or alkynyl, aryl, or heterocycle, each optionally containing one or more heteroatoms;

each S is optionally in the form of an oxide;

each R is H, halogen, carboxyl, cyano, amino, amido, an inorganic substituent, $SR^1$, $OR^1$ or $R^1$, wherein each $R^1$ is alkyl, alkenyl, alkynyl, aryl, heteroaryl, a carbocyclic ring or a heterocyclic ring, each of which is optionally substituted and may contain a heteroatom;

n is 1;
p is 1;
or a pharmaceutically acceptable salt thereof.

2. The compound of claim 1, wherein R is independently H, halo, $OR^1$, $SR^1$, $CO_2R^1$, $CONR^1_2$, C=O, CN, $CF_3$, $OCF_3$, $NO_2$, $NR_1R_1$, $OCOR_1$; or R is $C_{1-10}$ alkyl, $C_{3-10}$ cyclic alkyl, $C_{2-10}$ alkenyl, $C_{2-10}$ alkynyl, an aryl, heteroaryl, a carbocyclic ring or a heterocyclic ring, each of which may contain a heteroatom.

3. The compound of claim 1, wherein A and B are independently selected from pyridine, pyridazine, pyrimidine, pyrazine, triazine, isoxazole, isothiazole, oxadiazole, [1,2,4]oxadiazole, triazole, thiadiazole, pyrazole, imidazole, thiazole, oxazole, benzoxazole, pyrrole, thiophene, indolizine, indole, isoindole, indoline, benzofuran, benzothiophene, indazole, benzimidazole, benzthiazole, purine, quinoxaline, quinoline, isoquinoline, cinnoline, phthalazine, quinazoline, quinoxaline, naphthyridine, pteridine, acridine, phenazine, phenothiazine, indene, benzoxadiazol, and benzo[1,2,5]-oxadiazole.

4. The compound of claim 1, wherein A and B are independently selected from pyridine, pyridazine, pyrimidine, pyrazine, isoxazole, isothiazole, oxadiazole, thiazole, oxazole, benzoxazole, thiophene, indolizine, benzofuran, benzothiophene, and benzo[1,2,5]-oxadiazole.

5. The compound of claim 1, wherein said compound has the formula (7)

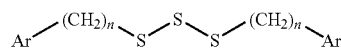

(7)

wherein Ar is an optionally substituted thiophene, benzothiophene, pyridine or pyrazine.

6. The compound of claim 1, wherein each R is H.

7. A method for ameliorating or treating neuroblastoma, comprising administering to a subject in need thereof an effective amount of a compound in claim 1 or a pharmaceutical composition thereof and optionally with an antiproliferative agent, whereby said neuroblastoma is ameliorated or treated.

8. A method for treating or ameliorating a cancer selected from the group consisting of leukemia, lymphoma, lung cancer, colon cancer, CNS cancer, melanoma, ovarian cancer, renal cancer, prostate cancer, breast cancer, head-neck cancer, pancreatic cancer, and renal cancer, comprising administering to a subject in need thereof an effective amount of the compound of claim 1, or a pharmaceutical composition thereof, and optionally with an antiproliferative agent;

whereby said cancer in said subject is ameliorated or treated.

9. The method of claim 8, wherein said subject is a human.

10. The method of claim 8, wherein said compound is a compound according to claim 2.

11. The method of claim 10, wherein said compound is a compound according to claim 3.

12. The method of claim 8, wherein said compound is a compound according to claim 5.

13. A method for ameliorating or treating restenosis, comprising administering to a subject in need thereof an effective amount of a compound of claim 1, or a pharmaceutical composition thereof, whereby restenosis in said subject is ameliorated or treated.

14. The method of claim 13, wherein said restenosis is associated with neointimal hyperplasia.

15. The method of claim 13, wherein said administering step is oral or parental administration, or administration via a stent.

16. A pharmaceutical composition comprising a compound of claim 1, and a pharmaceutically acceptable excipient.

17. A method for preparing a compound of claim 1, comprising:

a) contacting N-trimethylsilyl imidazole with sulfur dichloride in a halogenated solvent to provide diimidazolylsulfide; and b) contacting said diimidazolylsulfide with mercaptan.

18. A method for preparing a composition comprising a compound of claim 1, comprising:

a) dissolving a compound of claim 1 in a water-soluble organic solvent, a non-ionic solvent, a water-soluble lipid, a cyclodextrin, a vitamin, a fatty acid, a fatty acid ester, a phospholipid, or a combination thereof, to provide a solution; and b) adding saline or a buffer containing 1-10% carbohydrate solution.

19. The method of claim 7, wherein the subject is a human.

20. The method of claim 13, wherein the subject is a human.

* * * * *